US006962971B2

(12) United States Patent
Martins-Green et al.

(10) Patent No.: US 6,962,971 B2
(45) Date of Patent: Nov. 8, 2005

(54) CHEMOKINES AND METHODS FOR INDUCING THE DIFFERENTIATION OF FIBROBLASTS TO MYOFIBROBLASTS

(75) Inventors: Manuela Martins-Green, Riverside, CA (US); Jo Ellen Feugate, Riverside, CA (US); QiJing Li, Riverside, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 09/811,162

(22) Filed: Mar. 16, 2001

(65) Prior Publication Data

US 2003/0040109 A1 Feb. 27, 2003

(51) Int. Cl.[7] ........................ A61K 38/00; A61K 38/08; C07K 7/06

(52) U.S. Cl. .......................... 530/329; 530/327; 514/2; 514/15; 514/17

(58) Field of Search ................................ 530/329, 327; 530/350, 399; 514/2, 15, 17

(56) References Cited

U.S. PATENT DOCUMENTS

| 5,194,596 | A | * | 3/1993 | Tischer et al. ............... 530/399 |
| 5,350,836 | A | * | 9/1994 | Kopchick et al. ........... 530/399 |
| 5,401,651 | A |   | 3/1995 | Walz |
| 5,641,867 | A | * | 6/1997 | Stern et al. ............ 530/388.23 |
| 5,900,235 | A | * | 5/1999 | Gosselin et al. ........... 424/85.2 |
| 6,103,234 | A |   | 8/2000 | Wolpe et al. |

FOREIGN PATENT DOCUMENTS

| JP | 11-21296 A | 1/1999 |
| JP | 11-43445 A | 2/1999 |

OTHER PUBLICATIONS

Ngo et al., The Protein Folding Problem and Tertiary Structure Prediction, pp. 433–440 and 492–495 (1994).*
Wells, Additivity of Mutational Effects in Proteins. Biochemistry 29:8509–8517 (1990).*
Herbert et al. Scanning Mutagenesis of Interleukin-8 Identifies a Cluster of Residues Required for Receptor Binding. The Journal of Biological Chemistry, vol. 266/28 pp. 18989–18994 (1991).*
Oppenheim, J Overview of Chemokines. Adv. Exp. Med. Biol. vol. 351 pp. 183–186 (1993).*
Baggiolini, M Chemotactic and Inflammatory Cytokines–CXC and CC Proteins Adv. Exp. Med. Biol. vol. 351 pp. 1–11 (1993).*
Murdoch et al. Chemokine receptors and their role in inflammation and infectious disease Blood vol. 95/10 May 15, 2000.*
Well, JA Additivity of Mutational Effects in Proteins. Biochemistry 29:8509–8517 (1990).*
Yan et al. Two–Amino Acid Molecular Switch in an Epithelial Morphogen That Regulates Binding to Two Distinct Receptors. Science 90:523–527 (2000).*
Ngo et al. Computational Complexity, Protein Structure Prediction, and the Levinthal Paradox. The Protein Folding Problem and Tertiary Structure Prediction. Merz and Le Grand, Editors, Birkhauser, Boston, 1994.*
Baggiolini, M., Dewald, B., and B. Moser. 1997. Human chemokines: an update. Annu. Rev. Immunol. 15:675–705.
Bazan, J.F., Bacon, K.B., Hardiman, G., Wang, W., Soo, K., Rossi, D., Greaves, D.R., Zlotnik, A., and T.J. Schall. 1997. A new class of membrane–bound chemokine with a CX3C motif. Nature(Lond.) 385: 640–644.
Belperio, J.A., Keane, M., Arenberg, D., Addison, C., Ehlert, J., Burdick, M.D., and R. Strieter. 2000. CXC chemokines in angiogenesis. J. Leukoc. Biol. 68–:1–8.
Brown, L., Dubin, D., Lavigne, L., Logan, B., Dvorak, H., and L. Van de Water.1993. Macrophages and fibroblasts express embryonic fibronectins during cutaneous wound healing. Am. J. Pathol. 142:793–801.
Carmeliet, P. 2000. Mechanisms of angiogenesis and arteriogenesis. Nature Med. 6:389–95.
Clark, R. 1993. Basics of cutaneous wound repair. J. Dermatol. Surg. Oncol. 19:693–706.
Clark–Lewis, I., Kim K., Rajarathnam, K., Gong, J., Dewald, B., Moser, B., et al. 1995. Structure–activity relationships of chemokines. J Leukoc. Biol. 57:703–711.
Coffin, C., Dehner, L., and J. Meis–Kindblom. 1998 Inflammatory myofibroblastic tumor, inflammatory fibrosarcoma, and related lesions: an historical review with differential diagnostic considerations. Seminars in Diagnostic Pathology 15:102–110.
Desmouliere, A., Geinoz, A., Gabbiani, F., and G. Gabbiani. 1993. Transforming growth factor–beta 1 induces alpha–smooth muscle actin expression in granulation tissue myofibroblasts and in quiescent and growing cultured fibroblasts. J. Cell Biol. 122:103–111.

(Continued)

Primary Examiner—Elizabeth Kemmerer
Assistant Examiner—Regina M. DeBerry
(74) Attorney, Agent, or Firm—Emily M. Haliday; Quine Intellectual Property Law Group P.C.

(57) ABSTRACT

This invention is based on the discovery that chemokines induce fibroblasts to differentiate to myofibroblasts, which play a critical role in wound healing and are implicated in a number of fibrotic diseases. This activity has been localized to a peptide in the N-terminus of several chemokines. Accordingly, the invention provides polypeptides that induce the differentiation of fibroblasts to myofibroblasts in vitro and in vivo, nucleic acids encoding such polypeptides and related vectors, host cells, and composition containing these components. The invention also encompasses methods for inducing or inhibiting differentiation of fibroblasts to myofibroblasts, in vivo as well as in vitro, and screening methods for identifying other agents that modulate myofibroblast differentiation.

3 Claims, 11 Drawing Sheets

OTHER PUBLICATIONS

Devalaraja, R., Nanney, L., Qian, Q., Du, J., Yu, Y., Devalaraja, M.N., and A. Richmond. 2000. Delayed wound healing in CXCR2 knockout mice. J. Investig. Dermatol. 115:234–44.

Dimitrijevic–Bussod, M., Balzaretti–Maggi, V., and D. Gadbois. 1999. Extracellular matrix and radiation G1 cell cycle arrest in human fibroblasts. Cancer Res. 59:4843–4847.

Doucet, J., and J. Trifaro. 1988. A discontinous and highly porous sodium dodecyl sulfate–polyacrylamide slab gel system of high resolution. Anal. Biochem. 168:265–271.

Dunleavy, J., and J. Couchman. 1995. Interleukin–8 induces motile behavior and loss of focal adhesions in primary fibroblasts. J. Cell Sci. 108:311–321.

Engelhardt, E., Toksoy, A., Goebeler, M., Debus, S., Bröcker, E., and R. Gillitzer. 1998. Chemokines IL–8, GROalpha, MCP–1, IP–10, and Mig are sequentially and differentially expressed during phase–specific infiltration of leukocyte subsets in human wound healing. Amer. J. Pathol. 153:1849–1860.

Feugate, J, Li, Q., and Martins–Green, M. 2002. The cxc chemokine cCAF stimulates differentiation of fibroblasts into myofibroblasts and accelerates wound closure. J. of Cell Biology. 156:161–172.

Gabbiani, G. 1996. The cellular derivation and the life span of the myofibroblast. Pathol. Res. Pract. 192:708–711.

Germain, L., Jean, A., Auger, F., and D. Garrel. 1994. Human wound healing fibroblasts have greater contractile properties than dermal fibroblasts. J. Surg. Res. 57:268–273.

Gharaee–Kermani, M., Denholm, E., and S. Phan. 1996. Costimulation of fibroblast collagen and transforming growth factor b1 gene expression by monocyte chemoattractant protein–1 via specific receptors. J. Biol. Chem. 271:17779–17784.

Gupta, S. and J. Singh. 1994. Inhibition of endothelial cell proliferation by platelet factor–4 involves a unique action on S phase progression. J. Cell Biol. 127:1121–1127.

Hasegawa, M., Sato, S., and K. Takehara. 1999. Augmented production of chemokines (monocyte chemotactic protein–1 (MCP–1), macrophage inflammatory protein–1 alpha (MIP–1alpha) and MIP–1beta) in patients with systemic sclerosis: MCP–1 and MIP–1alpha may be involved in the development of pulmonary fibrosis. Clin. Exp. Immunol. 117:159–165.

Jester, J., Huang, J., Barry–Lane, P., Kao, W., Petroll, W., and H. Cavanagh. 1999. Transforming growth factor(beta)–mediated corneal myofibroblast differentiation requires actin and fibronectin assembly. Invest. Ophthalmol. Vis. Sci. 40:1959–1967.

Kadono, T., Kikuchi, K., Ihn, H., Takehara, K., and K. Tamaki. 1998. Increased production of interleukin 6 and interleukin 8 in scleroderma fibroblasts. J. Rheumatol. 25:296–301.

Keane, M., Arenberg, D., Lynch, J., Whyte, R., Iannettoni, M., Burdick, M., Wilke, C., Morris, S., Glass, M., DiGiovine, B., Kunkel, S., and R. Strieter. 1997. The CXC chemokines, IL–8 and IP–10, regulate angiogenic activity in idiopathic pulmonary fibrosis. J. Immunol. 159:1437–1443.

Khouw, I., van Wachem, P., Plantinga, J., Vujaskovic, Z., Wissink, M., de Leij, L., and M. van Luyn. 1999. TGF–beta and bFGF affect the differentiation of proliferating porcine fibroblasts into myofibroblasts in vitro. Biomaterials 20:1815–1822.

Lanning, D., Diegelmann, R., Yager, D., Wallace, M., Bagwell, C., and J. Haynes. 2000. Myofibroblast induction with transforming growth factor–beta1 and –beta3 in cutaneous fetal excisional wounds. J. Pediatr. Surg. 35:183–187.

Luo, Y., D,Amore, P., and M. Dorf. 1996. b–chemokine TCA3 binds to and activates rat vascular smooth muscle cells. J. Immunol. 157:2143–2148.

Luster, A., Cardiff, R., MacLean, J., Crowe, K., and R. Granstein. 1998. Delayed wound healing and disorganized neovascularization in transgenic mice expressing the IP–10 chemokine. Proceedings of the Association of American Physicians 110:183–196.

Mackie, E., Halfter, W., and D. Liverani. 1988. Induction of tenascin in healing wounds. J. Cell Biol. 107:2757–2767.

Martins–Green, M., and M. Bissell. 1990. Localization of 9E3/CEF–4 in avian tissues: expression is absent in Rous sarcoma virus–induced tumors but is stimulated by injury. J. Cell. Biol. 110:581–595.

Martins–Green, M., Tilley, C., Schwarz, R., Hatier, C., and M. Bissell. 1991. Wound–factor–induced and cell cycle phase–dependent expression of 9E3/CEF4, the avian gro gene. Cell Regul. 2:739–52.

Martins–Green, M., Aotaki–Keen, A., Hjelmeland, L., and M. Bissell. 1992. The 9E3 protein: immunolocalization in vivo and evidence for multiple forms in culture. J. Cell Sci. 101:701–707.

Martins–Green, M., Stoeckle, M., Hampe, A., Wimberly, S., and H. Hanafusa. 1996. The 9E3/CEF4 cytokine: kinetics of secretion, processing by plasmin, and interaction with extracellular matrix. Cytokine 8:448–459.

Martins–Green, M., and H. Hanafusa. 1997. The 9E3/CEF4 gene and its product the chicken chemotactic and angiogenic factor (cCAF): potential roles in wound healing and tumor development. Cytokine Growth Factor Rev. 8:221–232.

Martins–Green, M., and J.E. Feugate.1998. The 9E3/CEF4 gene product is a chemotactic and angiogenic factor that can initiate the wound healing cascade in vivo. Cytokine 10:522–535.

Martins–Green, M., and T. Kelly. 1998. The chicken chemotactic and angiogenic factor (9E3 gene product): Its angiogenic properties residue in the C–terminus of the molecule. Cytokine 10:819–830.

Masur, S., Dewal, H., Dinh, T. Erenburg, I., and S. Petridou. 1996. Myofibroblasts differentiate from fibroblasts when plated at low density. Proc. Natl. Acad. Sci. USA 93:4219–4223.

Nanney, L., Muellaer, S., Bueno, R., Pieper, S., and A. Richmond. 1995. Distribution of melanoma growth stimulatory activity or growth–regulated gene and the interleukin–8 receptor in human wound repair. Am. J. Pathol. 147:1248–1260.

Nedelec, B., Dodd, C., Scott, P., Ghahary, A., and E. Tredget. 1998. Effect of interferon–a2b on guinea pig wound closure and the expression of cytoskeletal proteins in vivo. Wound Repair. Reg. 6:202–212.

Nirodi, C., Devalaraja, R., Nanney, L., Arrindell, S., Russell, S., Trupin, J., and A. Richmond. 2000. Chemokine and chemokine receptor expression in keloid and normal fibroblasts. Wound Repair Regen. 8:371–382.

Powell, D., Mifflin, R., Valentich, J., Crowe, S., Saada, J., and A. West. 1999. Myofibroblasts. I. Paracrine cells important in health and disease. Am. J Physiol. 277:C1–C19.

Prieschl, E.E., Kulmburg, P.A., and T. Baumruker. 1995. The nomenclature of chemokines. Int. Arch. Allergy Immunol. 107: 475–483.

Rennekampff, H., Hansbrough, J., Woods, V., Dore, C., Kiessig, V., and J. Schroder. 1997. Role of melanoma growth stimulatory activity (MGSA/gro) on keratinocyte function in wound healing. Arch. Dermatol. Res. 289:204–212.

Serini, G., and G. Gabbiani. 1999. Mechanisms of myofibroblast activity and phenotypic modulation. Exp. Cell Res. 250:273–283.

Stoeckle, M., and K. Barker. 1990. Two burgeoning families of platelet factor 4–related proteins: mediators of the inflammatory response. New Biol. 2:313–323.

Strieter, R., Polverini, P., Arenberg, D., and S. Kunkel. 1995. Role of CXC chemokines as regulators of angiogenesis. Shock 4:155–160.

Weber, M., Uguccioni, M., Baggiolini, M., Clark–Lewis, I., and C. Dahinden. 1996. Deletion of the NH2–terminal residue converts monocyte chemotactic protein 1 from an activator of basophil release to an eosinophil chemoattractant. J. Exp. Med. 183:681–685.

Youngs, S., Ali, S., Taub, D., and R. Rees. 1997. Chemokines induce migrational responses in human breast carcinoma cell lines. Int. J. Cancer 71:257–266.

Zhang, Y., Zhang, Y., Ogata, M., Chen, P. Harada, A., Hashimoto S., and K. Matsushima. 1999. Transforming growth factor–b1 polarizes murine hematopoietic progenitor cells to generate Langerhans cell–like dendritic cells through a monocyte/macrophage differentiation pathway. Blood 93:1208–1220.

Zlotnik, A., Morales, J., and J. Hedrick. 1999. Recent advances in chemokines and chemokine receptors. Crit. Rev. Immol. 19:1–47.

* cited by examiner

SEQUENCE LISTING

<160> NUMBER OF SEQ ID NOS: 13

<210> SEQ ID NO 1
<211> LENGTH: 1182
<212> TYPE: DNA
<213> ORGANISM: Gallusgallus
<220> FEATURE:
<221> NAME/KEY: Unsure
<222> LOCATION: (1)..(2)
<223> OTHER INFORMATION: "n" is unsure

<400> SEQUENCE: 1

```
nntcagcaat cctctgacag gagagatcac agctccacaa aacctcagct cagaaaacaa      60
gccaaacact cctaaccatg aacggcaagc ttggagctgt cctggccctc ctcctggttt     120
cagctgctct gtcgcaaggt aggacgctgg taaagatggg gaatgagctg cggtgccagt     180
gcattagcac tcattctaag ttcatccacc ctaaatccat tcaagatgtg aagctgacgc     240
caagcggccc ccactgcaag aatgttgaaa tcatagctac tctaaaggat ggaagagagg     300
tgtgcttgga ccccactgct ccctgggtac agctgatcgt aaaggcactt atggccaagg     360
ctcagctcaa ttctgatgca ccactgtgag aaaattccag acaggaaaaa tcctcagaac     420
tgctcctgat ttctactggg agaaacatcc gaagaaggca tcatgaagca ttccatcttc     480
caccttccac atcggtgcct catgttaatt gcagatcctt gtatctattt atttatttat     540
ttaactgcat gtatttaaaa aagtctttca taatggtcag tgctgtggga ttcactgtcc     600
agtgaaactg aagacactga atagcaaaag ggcttgctag gggaaatgaa gatcccttgg     660
aagccacttc agtcagacac aatcagttaa gtgcaatgca cttacagcac agcttgtttg     720
tattaagccc tactgtgttg ctattacagc agcaaactgg taattcctcc tgctcccctg     780
gagtgctcta gtatgttgtg tcaacaacag tttcctagtc agagtcagct catgccgact     840
gcagactgtg tttaaaactt cagaaatcta acctgcagaa tctgtaagac tgtgggtttg     900
gtatttatta tgatttccat ggtatttata aatatattta tttactagtt tctatacaag     960
atggaaggag atgataactt gtgtaatttc tactggattt tctgttctta atgatgaata    1020
cttaagaaac attcacatac ccattactct gcataaggac ttggttctat gtctaatacg    1080
tgagttattc agctaatgga aaaaaaacta cagcatgcat acacagaatt tgcttgtgag    1140
aatgtaatta cctcttacaa tatattaata aatattttat tt                       1182
```

<210> SEQ ID NO 2
<211> LENGTH: 86
<212> TYPE: PRT
<213> ORGANISM: Gallusgallus

<400> SEQUENCE: 2

-continued

| Leu | Ser | Gln | Gly | Arg | Thr | Leu | Val | Lys | Met | Gly | Asn | Glu | Leu | Arg | Cys |
|---|---|---|---|---|---|---|---|---|---|---|---|---|---|---|---|
| 1 | | | | 5 | | | | | 10 | | | | | 15 | |

| Gln | Cys | Ile | Ser | Thr | His | Ser | Lys | Phe | Ile | His | Pro | Lys | Ser | Ile | Gln |
|---|---|---|---|---|---|---|---|---|---|---|---|---|---|---|---|
| | | | 20 | | | | | 25 | | | | | 30 | | |

| Asp | Val | Lys | Leu | Thr | Pro | Ser | Gly | Pro | His | Cys | Lys | Asn | Val | Glu | Ile |
|---|---|---|---|---|---|---|---|---|---|---|---|---|---|---|---|
| | | | 35 | | | | | 40 | | | | | 45 | | |

| Ile | Ala | Thr | Leu | Lys | Asp | Gly | Arg | Glu | Val | Cys | Leu | Asp | Pro | Thr | Ala |
|---|---|---|---|---|---|---|---|---|---|---|---|---|---|---|---|
| | 50 | | | | | 55 | | | | | 60 | | | | |

| Pro | Trp | Val | Gln | Leu | Ile | Val | Lys | Ala | Leu | Met | Ala | Lys | Ala | Gln | Leu |
|---|---|---|---|---|---|---|---|---|---|---|---|---|---|---|---|
| 65 | | | | | 70 | | | | | 75 | | | | | 80 |

| Asn | Ser | Asp | Ala | Pro | Leu |
|---|---|---|---|---|---|
| | | | | | 85 |

<210> SEQ ID NO 3
<211> LENGTH: 1633
<212> TYPE: DNA
<213> ORGANISM: Homosapiens

<400> SEQUENCE: 3

| agcagagcac acaagcttct aggacaagag ccaggaagaa accaccggaa ggaaccatct | 60 |
| cactgtgtgt aaacatgact tccaagctgg ccgtggctct cttggcagcc ttcctgattt | 120 |
| ctgcagctct gtgtgaaggt gcagttttgc aaggagtgc taaagaactt agatgtcagt | 180 |
| gcataaagac atactccaaa cctttccacc ccaaatttat caagaactg agagtgattg | 240 |
| agagtggacc acactgcgcc aacacagaaa ttattgtaaa gctttctgat ggaagagagc | 300 |
| tctgtctgga ccccaaggaa actgggtgc agagggttgt ggagaagttt ttgaagaggg | 360 |
| ctgagaattc ataaaaaaat tcattctctg tggtatccaa gaatcagtga agatgccagt | 420 |
| gaaacttcaa gcaaatctac ttcaacactt catgtattgt gtgggtctgt tgtagggttg | 480 |
| ccagatgcaa tacaagattc ctggttaaat ttgaatttca gtaaacaatg aatagttttt | 540 |
| cattgtacca tgaaatatcc agaacatact tatatgtaaa gtattattta tttgaatcta | 600 |
| caaaaaacaa caataatttt ttaaatataa ggattttcct agatattgca cgggagaata | 660 |
| tacaaatagc aaaattgagg ccaagggcca agagaatatc cgaactttaa tttcaggaat | 720 |
| tgaatgggtt tgctagaatg tgatatttga agcatcacat aaaaatgatg ggacaataaa | 780 |
| ttttgccata aagtcaaatt tagctggaaa tcctggattt ttttctgtta aatctggcaa | 840 |
| ccctagtctg ctagccagga tccacaagtc cttgttccac tgtgccttgg tttctccttt | 900 |
| atttctaagt ggaaaagta ttagccacca tcttacctca cagtgatgtt gtgaggacat | 960 |
| gtggaagcac tttaagtttt ttcatcataa cataaattat tttcaagtgt aacttattaa | 1020 |
| cctatttatt atttatgtat ttatttaagc atcaaatatt tgtgcaagaa tttggaaaaa | 1080 |
| tagaagatga atcattgatt gaatagttat aaagatgtta tagtaaattt attttatttt | 1140 |
| agatattaaa tgatgtttta ttagataaat ttcaatcagg gttttagat taaacaaaca | 1200 |
| aacaattggg tacccagtta aattttcatt tcagataaac aacaaataat tttttagtat | 1260 |
| aagtacatta ttgtttatct gaaattttaa ttgaactaac aatcctagtt tgatactccc | 1320 |
| agtcttgtca ttgccagctg tgttggtagt gctgtgttga attacggaat aatgagttag | 1380 |
| aactattaaa acagccaaaa ctccacagtc aatattagta atttcttgct ggttgaaact | 1440 |
| tgtttattat gtacaaatag attcttataa tattatttaa atgactgcat ttttaaatac | 1500 |
| aaggctttat attttaact ttaagatgtt tttatgtgct ctccaaattt tttttactgt | 1560 |
| ttctgattgt atggaaatat aaaagtaaat atgaaacatt taaaatataa tttgttgtca | 1620 |

```
-continued aagtaatcaa gtg                                                          1633

<210> SEQ ID NO 4
<211> LENGTH: 77
<212> TYPE: PRT
<213> ORGANISM: Homosapiens

<400> SEQUENCE: 4

Ala Val Leu Pro Arg Ser Ala Lys Glu Leu Arg Cys Gln Cys Ile Lys
1               5                   10                  15

Thr Tyr Ser Lys Pro Phe His Pro Lys Phe Ile Lys Glu Leu Arg Val
            20                  25                  30

Ile Glu Ser Gly Pro His Cys Ala Asn Thr Glu Ile Ile Val Lys Leu
        35                  40                  45

Ser Asp Gly Arg Glu Leu Cys Leu Asp Pro Lys Glu Asn Trp Val Gln
    50                  55                  60

Arg Val Val Glu Lys Phe Leu Lys Arg Ala Glu Asn Ser
65                  70                  75

<210> SEQ ID NO 5
<211> LENGTH: 72
<212> TYPE: PRT
<213> ORGANISM: Homosapiens

<400> SEQUENCE: 5

Ser Ala Lys Glu Leu Arg Cys Gln Cys Ile Lys Thr Tyr Ser Lys Pro
1               5                   10                  15

Phe His Pro Lys Phe Ile Lys Glu Leu Arg Val Ile Glu Ser Gly Pro
            20                  25                  30

His Cys Ala Asn Thr Glu Ile Ile Val Lys Leu Ser Asp Gly Arg Glu
        35                  40                  45

Leu Cys Leu Asp Pro Lys Glu Asn Trp Val Gln Arg Val Val Glu Lys
    50                  55                  60

Phe Leu Lys Arg Ala Glu Asn Ser
65                  70

<210> SEQ ID NO 6
<211> LENGTH: 1102
<212> TYPE: DNA
<213> ORGANISM: Homosapiens

<400> SEQUENCE: 6
acagagcccg ggccgcaggc acctcctcgc cagctcttcc gctcctctca cagccgccag     60
acccgcctgc tgagccccat ggcccgcgct gctctctccg ccgccccag caatccccgg    120 ctcctgcgag tggcgctgct gctcctgctc ctggtagccg ctggccggcg cgcagcagga    180
gcgtccgtgg ccactgaact cgcgctgcca gtgcttgcaga ccctgcaggg aattcacccc    240
aagaacatcc aaagtgtgaa cgtgaagtcc cccggacccc actgcgccca aaccgaagtc    300
atagccacac tcaagaatgg gcggaaagct tgcctcaatc ctgcatcccc catagttaag    360
aaaatcatcg aaaagatgct gaacagtgac aaatccaact gaccagaagg gaggaggaag    420
ctcactggtg gctgttcctg aaggaggccc tgcccttata ggaacagaag ggaaagaga     480 gacacagctg cagaggccac ctggattgtg cctaatgtgt ttgagcatcg cttaggagaa    540
gtcttctatt tatttattta ttcattagtt ttgaagattc tatgttaata ttttaggtgt    600
aaaataatta agggtatgat taactctacc tgcacactgt cctattatat tcattctttt    660
```

| | | |
|---|---|---|
| tgaaatgtca accccaagtt agttcaatct ggattcatat ttaatttgaa ggtagaatgt | 720 |
| tttcaaatgt tctccagtca ttatgttaat atttctgagg agcctgcaac atgccagcca | 780 |
| ctgtgataga ggctggcgga tccaagcaaa tggccaatga gatcattgtg aaggcagggg | 840 |
| aatgtatgtg cacatctgtt ttgtaactgt ttagatgaat gtcagttgtt atttattgaa | 900 |
| atgatttcac agtgtgtggt caacatttct catgttgaaa ctttaagaac taaaatgttc | 960 |
| taaatatccc ttggacattt tatgtctttc ttgtaaggca tactgccttg tttaatggta | 1020 |
| gttttacagt gtttctggct tagaacaaag gggcttaatt attgatgttt tcatagagaa | 1080 |
| tataaaaata aagcacttat ag | 1102 |

<210> SEQ ID NO 7
<211> LENGTH: 73
<212> TYPE: PRT
<213> ORGANISM: Homosapiens

<400> SEQUENCE: 7

```
Ala Ser Val Ala Thr Glu Leu Arg Cys Gln Cys Leu Gln Thr Leu Gln
1               5                   10                  15
Gly Ile His Pro Lys Asn Ile Gln Ser Val Asn Val Lys Ser Pro Gly
                20                  25                  30
Pro His Cys Ala Gln Thr Glu Val Ile Ala Thr Leu Lys Asn Gly Arg
            35                  40                  45
Lys Ala Cys Leu Asn Pro Ala Ser Pro Ile Val Lys Lys Ile Ile Glu
        50                  55                  60
Lys Met Leu Asn Ser Asp Lys Ser Asn
65                  70
```

<210> SEQ ID NO 8
<211> LENGTH: 6
<212> TYPE: PRT
<213> ORGANISM: Homosapiens

<400> SEQUENCE: 8

```
Ser Ala Lys Glu Leu Arg
1               5
```

<210> SEQ ID NO 9
<211> LENGTH: 11
<212> TYPE: PRT
<213> ORGANISM: Homosapiens

<400> SEQUENCE: 9

```
Ala Val Leu Pro Arg Ser Ala Lys Glu Leu Arg
1               5                   10
```

<210> SEQ ID NO 10
<211> LENGTH: 15
<212> TYPE: PRT
<213> ORGANISM: Gallusgallus

<400> SEQUENCE: 10

```
Leu Ser Gln Gly Arg Thr Leu Val Lys Met Gly Asn Glu Leu Arg
1               5                   10                  15
```

<210> SEQ ID NO 11
<211> LENGTH: 8
<212> TYPE: PRT
<213> ORGANISM: Homosapiens

<400> SEQUENCE: 11

```
Ala Ser Val Ala Thr Glu Leu Arg
1               5
```

<210> SEQ ID NO 12
<211> LENGTH: 21
<212> TYPE: DNA
<213> ORGANISM: Gallusgallus

<400> SEQUENCE: 12
ggagcacctg aggacattga c        21

<210> SEQ ID NO 13
<211> LENGTH: 21
<212> TYPE: DNA
<213> ORGANISM: Gallusgallus

<400> SEQUENCE: 13
gcttcagtca gcagagttgg g        21

CHEMOKINES AND METHODS FOR INDUCING THE DIFFERENTIATION OF FIBROBLASTS TO MYOFIBROBLASTS

STATEMENT AS TO RIGHTS TO INVENTIONS MADE UNDER FEDERALLY SPONSORED RESEARCH AND DEVELOPMENT

This work was supported, in part, by grant no. GM48436 from the National Institutes of Health. The Government of the United States of America may have certain rights in this invention.

FIELD OF THE INVENTION

This invention relates to chemokines and chemokine fragments that induce fibroblasts to differentiate to myofibroblasts and related methods.

BACKGROUND OF THE INVENTION

Chemokines are primarily known for their roles in inflammatory and immune responses. However, these small cytokines have also been shown to be upregulated during development of the granulation tissue of wounds and to act on endothelial cells and keratinocytes, cells that perform important functions in the development of the healing tissue (Martins-Green and Bissell, 1990; Nanney et al., 1995; Martins-Green and Feugate, 1998; Luster et al., 1998). In addition to these cell types, fibroblasts are also critical players during formation of the granulation tissue. These cells are activated by cytokines and growth factors that are released from platelets and produced by macrophages. The activated fibroblasts proliferate and migrate across the provisional matrix formed by the fibrin-plasma fibronectin clot. As the clot is digested by plasmin, fibroblasts replace it with cellular fibronectin, tenascin and collagen III (Mackie et al., 1988; Clark, 1993), molecules that are critical for migration of endothelial cells and keratinocytes into the wound and for proper scar formation. Some of the fibroblasts infiltrating the wound differentiate to become myofibroblasts (Gabbiani, 1996; Powell et al., 1999), cells that have bundles of α-smooth muscle actin (α-SMA) and can contract, contributing to closure of the wound (Germain et al., 1994; Lanning et al., 2000).

Chemokines are small, positively charged, secreted proteins that consist of an N-terminal region of variable conformation, followed by a loop, three antiparallel beta strands and a C-terminal alpha helix (Clark-Lewis et al., 1995). They can be divided into four families based on the position of the first two cysteines. The two major families are the CXC family in which the two cysteines are separated by any single amino acid [e.g. cCAF, IL-8, gro-α/MGSA, SDF-1, PF4, IP-10] and the CC family in which the two cysteines are adjacent [MCPs, RANTES, Eotaxin, MIPs] (Prieschl et al., 1995; Bazan et al., 1997; Zlotnik et al., 1999). These proteins have no modifications other than two disulfide bonds and are multifunctional. Chemokines function in a very tightly regulated dose- and time-dependent manner, strongly suggesting that their actions are affected by the microenvironmental conditions (Dunleavy and Couchman, 1995; Gharaee-Kermani et al., 1996; Rennekampf et al., 1997; Youngs et al., 1997).

The first evidence that chemokines are associated with healing was reported in 1990 when it was shown that the chemokine cCAF (chicken Chemotactic and Angiogenic Factor) is overexpressed during wound healing (Martins-Green and Bissell, 1990). This chemokine is highly expressed in the first 24–48 hours after injury and remains elevated for at least 16 days after wounding (Martins-Green and Bissell, 1990; Martins-Green at el., 1992; Martins-Green and Hanafusa, 1997). It is primarily expressed by the fibroblasts of the granulation tissue, especially where interstitial collagen is abundant and by the endothelial cells of microvessels of the granulation tissue (Martins-Green and Bissell 1990; Martins-Green at al., 1992).

In the chicken chorioallantoic membrane (CAM) assay, at low doses, cCAF is chemotactic for monocyte/macrophages and lymphocytes and after several days of exposure to this chemokine, the ectoderm of the CAM becomes thickened and a granulation-like tissue develops beneath the cCAF-containing pellet. In this granulation-like tissue, there is an increase in the amount of interstitial collagen, and the fibroblasts in the mesoderm are consistently aligned with the collagen fibers and appear to cause tissue contraction (Martins-Green and Feugate, 1998). At high concentrations, however, cCAF stimulates blood vessel sprouting from the preexisting vessels of the CAM (angiogenesis) in the absence of leukocyte chemotaxis (Martins-Green and Feugate, 1998).

Other CXC chemokines have also been associated with wound healing events. For example, in bum wounds, gro-α/MGSA is expressed by keratinocytes as they differentiate after re-epithelialization of the wound. Furthermore, CXCR2, the receptor for MGSA, is present in migrating and proliferating keratinocytes (Nanney et al., 1995; Rennekampff et al., 1997). In the granulation tissue, MGSA expression is associated with fibroblasts, smooth muscle cells/myofibroblasts and a subpopulation of macrophages (Nanney et al., 1995). This pattern of expression strongly suggests a role of this chemokine in healing of burn wounds. It also has been shown that in transgenic mice expressing IP-10, a CXC chemokine that inhibits angiogenesis, wounds heal poorly and exhibit defects in development of the granulation tissue (Luster et al., 1998).

It is becoming increasingly more evident that chemokines are expressed at the sites of injury and that they affect processes involving proper development of the granulation tissue. Fibroblasts are critical participants in the development of this healing tissue and they also express high levels of chemokines upon stimulation by stress-inducing agents such as those released upon wounding. Despite this correlative evidence, little is known about how these small cytokines affect wound fibroblast function.

SUMMARY OF THE INVENTION

The invention provides a polypeptide including a chemokine fragment that stimulates the differentiation of fibroblasts to myofibroblasts, wherein the polypeptide is other than the full-length, wild-type chemokine, and is preferably not angiogenic. In preferred embodiments, the chemokine fragment is a fragment of a CXC chemokine, more preferably an N-terminal CXC chemokine fragment, and most preferably, one including an ELR motif. In specific, preferred embodiments, the chemokine fragment of the polypeptide includes an amino acid sequence that is at least about 70%, and more preferably at least about 90%, identical to an N-terminal amino acid sequence of chicken chemotactic and angiogenic factor (cCAF), interleukin-8 (IL-8), or melanoma growth stimulatory activity (MGSA). For example, the CXC chemokine fragment can include an amino acid sequence selected from the group consisting of SEQ ID NO:8, SEQ ID NO:9, SEQ ID NO:10, and SEQ ID NO:11.

Other aspects of the invention include a nucleic acid molecule encoding a polypeptide of the invention, a vector including this nucleic acid molecule, and a host cell including this vector.

The invention also provides compositions including a polypeptide or a nucleic acid molecule of the invention and a pharmaceutically acceptable carrier. In another embodiment, the invention provides a pharmaceutical composition including a nucleic acid molecule encoding a differentiation-inducing CXC chemokine, or a fragment thereof, wherein administration of the composition to cells including fibroblasts results in the expression of the differentiation-inducing CXC chemokine, or fragment thereof, in an amount sufficient to induce differentiation of fibroblasts to myofibroblasts. This composition additionally contains a pharmaceutically acceptable carrier.

Other aspects of the invention are methods of inducing or inhibiting differentiation of fibroblasts to myofibroblasts. The method of inducing differentiation entails contacting fibroblasts with an effective amount of a polypeptide of the invention to induce differentiation of the fibroblasts to myofibroblasts. The polypeptide can be administered to the fibroblasts directly, i.e., by contacting fibroblasts with a composition including the polypeptide. Alternatively, the polypeptide can be administered indirectly by administering a composition including a nucleic acid molecule encoding the polypeptide to cells including fibroblasts, whereby this administration results in the expression of the polypeptide, in an amount sufficient to induce differentiation of fibroblasts to myofibroblasts. Either embodiment can be carried out in vitro or in vivo. In another embodiment, the method is carried out in vitro and entails contacting fibroblasts with an effective amount of a differentiation-inducing CXC chemokine, or fragment thereof, thereby inducing the differentiation of the fibroblasts to myofibroblasts. In yet another embodiment, the method is performed in vivo and involves administering a composition including a nucleic acid molecule encoding a differentiation-inducing CXC chemokine, or a fragment thereof, to cells including fibroblasts. This administration results in the expression of the differentiation-inducing CXC chemokine, or fragment thereof, in an amount sufficient to induce differentiation of fibroblasts to myofibroblasts.

In preferred embodiments, the polypeptide (or a nucleic acid molecule encoding it) is administered to a subject having, or at risk for, a condition that can be ameliorated by differentiation of fibroblasts to myofibroblasts, such as for example a condition characterized by a deficiency of myofibroblasts. In a particularly preferred embodiment, the condition is a wound and differentiation of fibroblasts to myofibroblasts promotes wound healing.

The method of inhibiting the differentiation of fibroblasts to myofibroblasts includes contacting fibroblasts with an effective amount of an inhibitor of a differentiation-inducing chemokine during or prior to contact of the fibroblasts with the differentiation inducing chemokine or fragment thereof. This method can be performed in vitro or in vivo. In preferred embodiments, the method is performed by administering the inhibitor to a subject having, or at risk for, a condition that can be ameliorated by inhibiting the differentiation of fibroblasts to myofibroblasts, such as for example a condition characterized by excess myofibroblasts. Examples of conditions amenable to treatment by this method include keloid formation, pulmonary fibrosis, scleroderma, and cancer. In a preferred embodiment, the inhibitor is an antibody that specifically binds the CXC chemokine.

The invention also provides a screening method and two prescreening methods for identifying agents that induce or inhibit the differentiation of fibroblasts to myofibroblasts. The screening method entails contacting a cell including differentiation-inducing chemokine gene with a test agent and detecting the level of the differentiation-inducing chemokine mRNA or protein. An increase in the level of the mRNA or protein, as compared to said level in a cell of the same type contacted with a smaller amount of the test agent, indicates that the test agent induces differentiation. Conversely, a decrease in the level of the mRNA or protein, as compared to said level in a cell of the same type contacted with a smaller amount of the test agent, indicates that the test agent inhibits differentiation.

One prescreening method of the invention involves contacting a differentiation-inducing chemokine nucleic acid or protein with a test agent and detecting specific binding of the test agent to the nucleic acid or protein. A second prescreening method entails contacting a receptor for a differentiation-inducing chemokine with a test agent and detecting specific binding of the test agent to the receptor.

In preferred embodiments, the screening and prescreening methods of the invention additionally entail recording any test agent that specifically binds to the receptor in a database of candidate agents that may induce or inhibit differentiation of fibroblasts to myofibroblasts.

DETAILED DESCRIPTION

I. Definitions

Figure 1:
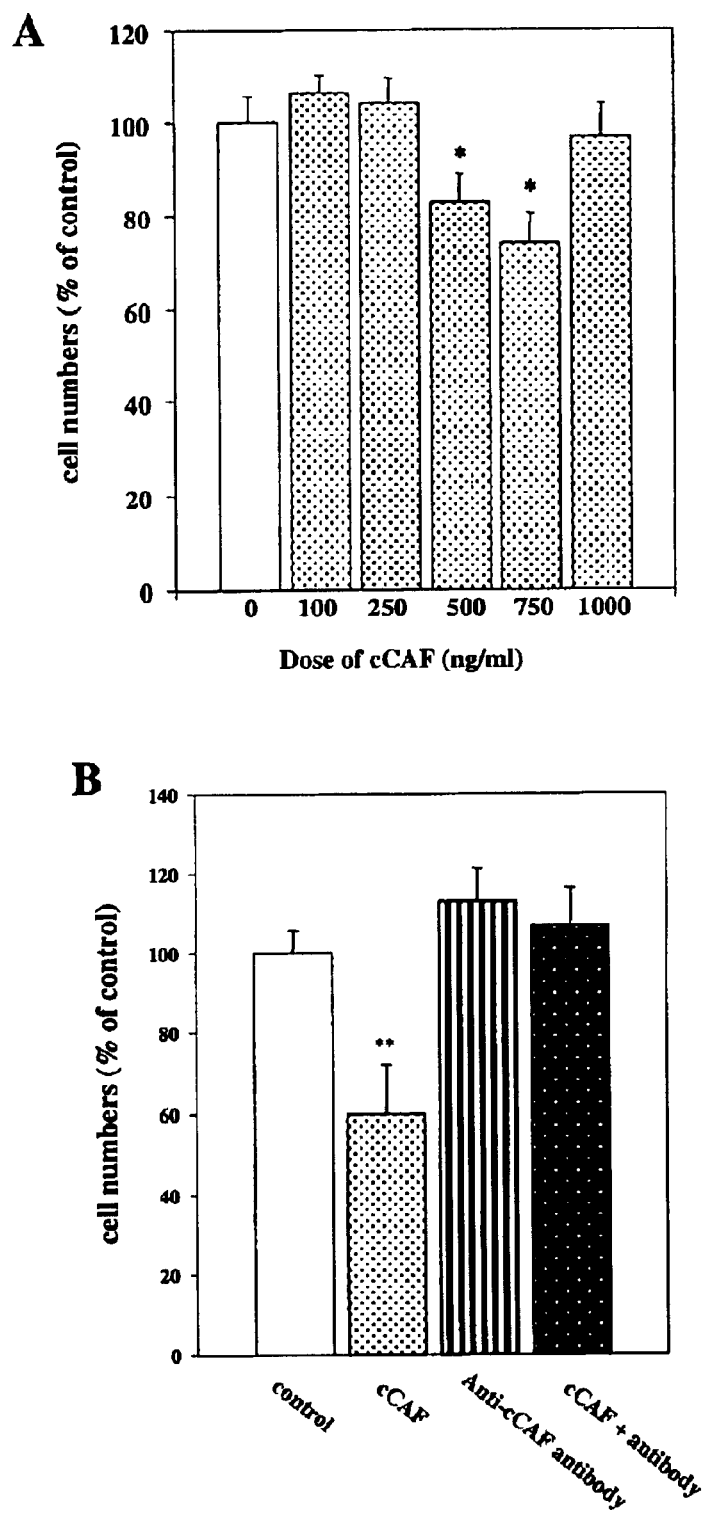
FIG. 1: The effects of cCAF on fibroblast growth. (A) Primary connective tissue embryonic fibroblasts were treated for 3 days with increasing doses of cCAF. Treatment was applied every 24 hrs. cCAF suppresses fibroblast proliferation in a dose-dependent pattern characteristic of most chemokine functions. Maximum suppression was observed at a dose of 750 ng/ml. (B) Inhibition of cCAF function with an antibody specific to this chemokine abrogates this suppression of growth. Results shown are representative of several independent experiments. (**=$p<0.01$; *=$p<0.05$).

Terms used in the claims and specification are defined as set forth below unless otherwise specified.

The term "nucleic acid molecule" refers to a deoxyribonucleotide or ribonucleotide polymer, and unless otherwise limited, includes known analogs of natural nucleotides that can function in a similar manner to naturally occurring nucleotides. The term "nucleic acid molecule" refers any form of DNA or RNA, including, for example, genomic DNA; complementary DNA (cDNA), which is a DNA representation of mRNA, usually obtained by reverse transcription of messenger RNA (mRNA) or amplification; DNA molecules produced synthetically or by amplification; and mRNA. The term "nucleic acid molecule" encompasses double-stranded nucleic acid molecules, as well as single-stranded molecules. In double-stranded nucleic acid molecules, the nucleic acid molecule strands need not be coextensive (i.e, a double-stranded nucleic acid molecule need not be double-stranded along the entire length of both strands).

As used herein, the term "gene" refers to a nucleic acid molecule comprising one or more regulatory sequences that modulate the expression of the linked coding sequences. Thus, a "chemokine gene" refers to a nucleic acid molecule that contains one or more sequences that regulate expression of the chemokine gene in vivo. This term encompasses nucleic acid molecules in which a chemokine promoter, for example, is operably linked to a heterologous nucleic acid molecule encoding a reporter (i.e., readily detected) protein.

The terms "polypeptide" and "protein" are used interchangeably herein to a polymer of amino acids, and unless otherwise limited, includes atypical amino acids that can function in a similar manner to naturally occurring amino acids.

The term "amino acid" or "amino acid residue," as used herein, includes naturally occurring L-amino acids or residues, unless otherwise specifically indicated. The commonly used one- and three-letter abbreviations for amino acids are used herein (Lehninger, A. L. (1975) Biochemistry, 2d ed., pp. 71–92, Worth Publishers, N.Y.). The terms "amino acid" and "amino acid residue" include D-amino acids as well as chemically modified amino acids, such as amino acid analogs, naturally occurring amino acids that are not usually incorporated into proteins, and chemically synthesized compounds having the characteristic properties of amino acids (collectively, "atypical" amino acids). For example, analogs or mimetics of phenylalanine or proline, which allow the same conformational restriction of the peptide compounds as natural Phe or Pro are included within the definition of "amino acid."

Exemplary atypical amino acids, include, for example, those described in International Publication No. WO 90/01940 as well as 2-amino adipic acid (Aad) which can be substituted for Glu and Asp; 2-aminopimelic acid (Apm), for Glu and Asp; 2-aminobutyric acid (Abu), for Met, Leu, and other aliphatic amino acids; 2-aminoheptanoic acid (Ahe), for Met, Leu, and other aliphatic amino acids; 2-aminoisobutyric acid (Aib), for Gly; cyclohexylalanine (Cha), for Val, Leu, and Ile; homoarginine (Har), for Arg and Lys; 2,3-diaminopropionic acid (Dpr), for Lys, Arg, and His; N-ethylglycine (EtGly) for Gly, Pro, and Ala; N-ethylasparagine (EtAsn), for Asn and Gln; hydroxyllysine (Hyl), for Lys; allohydroxyllysine (Ahyl), for Lys; 3- (and 4-) hydoxyproline (3Hyp, 4Hyp), for Pro, Ser, and Thr; allo-isoleucine (Aile), for Ile, Leu, and Val; amidinophenylalanine, for Ala; N-methylglycine (MeGly, sarcosine), for Gly, Pro, and Ala; N-methylisoleucine (MeIle), for Ile; norvaline (Nva), for Met and other aliphatic amino acids; norleucine (Nle), for Met and other aliphatic amino acids; ornithine (Orn), for Lys, Arg, and His; citrulline (Cit) and methionine sulfoxide (MSO) for Thr, Asn, and Gln; N-methylphenylalanine (MePhe), trimethylphenylalanine, halo (F, Cl, Br, and I) phenylalanine, and trifluorylphenylalanine, for Phe.

As used with reference to a polypeptide, the term "full-length" refers to a polypeptide having the same length as the mature wild-type polypeptide.

The term "fragment" is used herein with reference to a polypeptide or a nucleic acid molecule to describe a portion of a larger molecule. Thus, a polypeptide fragment can lack an N-terminal portion of the larger molecule, a C-terminal portion, or both. Polypeptide fragments are also referred to herein as "peptides." A fragment of a nucleic acid molecule can lack a 5' portion of the larger molecule, a 3' portion, or both. Nucleic acid fragments are also referred to herein as "oligonucleotides." Oligonucleotides are relatively short nucleic acid molecules, generally shorter than 200 nucleotides, more particularly, shorter than 100 nucleotides, most particularly, shorter than 50 nucleotides. Typically, oligonucleotides are single-stranded DNA molecules.

An "N-terminal fragment" is a polypeptide fragment that has an amino acid sequence present in the N-terminal half of a larger polypeptide. An "N-terminal peptide" of cCAF described herein is a 15-amino acid peptide shown in Table 3.

A C-terminal angiogenic peptide of cCAF is a 28-amino acid peptide extending from residues 59–86 of cCAF (SEQ ID NO:2), which is shown in Table 2.

As used with reference to polypeptides, the term "wild-type" refers to any polypeptide having an amino acid sequence present in a polypeptide from a naturally occurring organism, regardless of the source of the molecule; i.e., the term "wild-type" refers to sequence characteristics, regardless of whether the molecule is purified from a natural source; expressed recombinantly, followed by purification; or synthesized.

The term "amino acid sequence variant" refers to a polypeptide having an amino acid sequence that differs from a wild-type amino acid sequence by the addition, deletion, or substitution of an amino acid.

The terms "identical" or "percent identity," in the context of two or more amino acid or nucleotide sequences, refer to two or more sequences or subsequences that are the same or have a specified percentage of amino acid residues or nucleotides that are the same, when compared and aligned for maximum correspondence, as measured using one of the following sequence comparison algorithms or by visual inspection.

For sequence comparison, typically one sequence acts as a reference sequence, to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, Adv. Appl. Math. 2:482 (1981), by the homology alignment algorithm of Needleman & Wunsch, J. Mol. Biol. 48:443 (1970), by the search for similarity method of Pearson & Lipman (1988) Proc. Natl. Acad. Sci. USA 85:2444, by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally Ausubel et al., supra).

One example of a useful algorithm is PILEUP. PILEUP creates a multiple sequence alignment from a group of related sequences using progressive, pairwise alignments to show relationship and percent sequence identity. It also plots a tree or dendogram showing the clustering relationships used to create the alignment. PILEUP uses a simplification of the progressive alignment method of Feng & Doolittle (1987) J. Mol. Evol. 35:351–360. The method used is similar to the method described by Higgins & Sharp (1989) CABIOS 5: 151–153. The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of algorithm that is suitable for determining percent sequence identity and sequence similarity is the BLAST algorithm, which is described in Altschul et al. (1990) J. Mol. Biol. 215: 403–410. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=-4, and a comparison of both strands. For amino acid sequences, the BLASTP program uses as defaults a wordlength (W) of 3, an expectation (E) of 10, and the BLOSUM62 scoring matrix (see Henikoff & Henikoff (1989) Proc. Natl. Acad. Sci. USA 89: 10915).

In addition to calculating percent sequence identity, the BLAST algorithm also performs a statistical analysis of the similarity between two sequences (see, e.g., Karlin & Altschul (1993) Proc. Natl. Acad. Sci. USA ,90: 5873–5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

Residues in two or more polypeptides are said to "correspond" if they are either homologous (i.e., occupying similar positions in either primary, secondary, or tertiary structure) or analogous (i.e., having the same or similar functional capacities). As is well known in the art, homologous residues can be determined by aligning the polypeptide sequences for maximum correspondence as described above.

The term "conservative amino acid substitution" is used herein to refer to the replacement of an amino acid with a functionally equivalent amino acid. Functionally equivalent amino acids are generally similar in size and/or character (e.g., charge or hydrophobicity) to the amino acids they replace. Amino acids of similar character can be grouped as follows:

(1) hydrophobic: His, Trp, Tyr, Phe, Met, Leu, Ile, Val, Ala;
(2) neutral hydrophobic: Cys, Ser, Thr;
(3) polar: Ser, Thr, Asn, Gln;
(4) acidic/negatively charged: Asp, Glu;
(5) charged: Asp, Glu, Arg, Lys, His;
(6) basic/positively charged: Arg, Lys, His;
(7) basic: Asn, Gln, His, Lys, Arg;
(8) residues that influence chain orientation: Gly, Pro; and
(9) aromatic: Trp, Tyr, Phe, His.

The following table shows exemplary and preferred conservative amino acid substitutions.

| Original Residue | Exemplary Conservative Substitution | Preferred Conservative Substitution |
|---|---|---|
| Ala | Val, Leu, Ile | Val |
| Arg | Lys, Gln, Asn | Lys |
| Asn | Gln, His, Lys, Arg | Gln |
| Asp | Glu | Glu |
| Cys | Ser | Ser |
| Gln | Asn | Asn |
| Glu | Asp | Asp |
| Gly | Pro | Pro |
| His | Asn, Gln, Lys, Arg | Asn |
| Ile | Leu, Val, Met, Ala, Phe | Leu |
| Leu | Ile, Val, Met, Ala, Phe | Ile |
| Lys | Arg, Gln, Asn | Arg |
| Met | Leu, Phe, Ile | Leu |
| Phe | Leu, Val, Ile, Ala | Leu |
| Pro | Gly | Gly |
| Ser | Thr | Thr |
| Thr | Ser | Ser |
| Trp | Tyr | Tyr |
| Tyr | Trp, Phe, Thr, Ser | Phe |
| Val | Ile, Leu, Met, Phe, Ala | Leu |

As used with reference to a polypeptide or polypeptide fragment, the term "derivative" includes amino acid sequence variants as well as any other molecule that differs from a wild-type amino acid sequence by the addition, deletion, or substitution of one or more chemical groups. As used herein, "derivatives" retain at least one biological or immunological property of a wild-type polypeptide or polypeptide fragment, such as, for example, the biological property of specific binding to a receptor and the immunological property of specific binding to an antibody.

The term "specific binding" is defined herein as the preferential binding of one binding partners to another (e.g., two polypeptides, a polypeptide and nucleic acid molecule, or two nucleic acid molecules) at specific sites. The term "specifically binds" indicates that the binding preference (e.g., affinity) for the target molecule/sequence is at least 2-fold, more preferably at least 5-fold, and most preferably at least 10- or 20-fold over a non-specific target molecule (e.g. a randomly generated molecule lacking the specifically recognized site(s)).

As used herein, the term "receptor" refers to a component of a cell, typically a protein, that specifically binds to one or more particular ligands. The receptor is said to be a receptor for such ligand(s).

As used herein, an "antibody" refers to a protein consisting of one or more polypeptides substantially encoded by immunoglobulin genes or fragments of immunoglobulin genes. The recognized immunoglobulin genes include the kappa, lambda, alpha, gamma, delta, epsilon and mu constant region genes, as well as myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively.

A typical immunoglobulin (antibody) structural unit is known to comprise a tetramer. Each tetramer is composed of two identical pairs of polypeptide chains, each pair having one "light" (about 25 kD) and one "heavy" chain (about 50–70 kD). The N-terminus of each chain defines a variable region of about 100 to 110 or more amino acids primarily responsible for antigen recognition. The terms "variable light chain (VL)" and "variable heavy chain (VH)" refer to these light and heavy chains respectively.

Antibodies exist as intact immunoglobulins or as a number of well-characterized fragments produced by digestion with various peptidases. Thus, for example, pepsin digests an antibody below the disulfide linkages in the hinge region to produce F(ab)'2, a dimer of Fab which itself is a light chain joined to VH-CH1 by a disulfide bond. The F(ab)'2 may be reduced under mild conditions to break the disulfide linkage in the hinge region thereby converting the (Fab')2 dimer into a Fab' monomer. The Fab' monomer is essentially a Fab with part of the hinge region (see, Fundamental Immunology, W. E. Paul, ed., Raven Press, N.Y. (1993), for a more detailed description of other antibody fragments). While various antibody fragments are defined in terms of the digestion of an intact antibody, one of skill will appreciate that such Fab' fragments may be synthesized de novo either chemically or by utilizing recombinant DNA methodology. Thus, the term antibody, as used herein also includes antibody fragments either produced by the modification of whole antibodies or synthesized de novo using recombinant DNA methodologies. Preferred antibodies include single chain antibodies (antibodies that exist as a single polypeptide chain), more preferably single chain Fv antibodies (sFv or scFv) in which a variable heavy and a variable light chain are joined together (directly or through a peptide linker) to form a continuous polypeptide. The single chain Fv antibody is a covalently linked VH-VL heterodimer which may be expressed from a nucleic acid including VH- and VL-encoding sequences either joined directly or joined by a peptide-encoding linker. Huston, et al. (1988) Proc. Nat. Acad. Sci. USA, 85: 5879–5883. While the VH and VL are connected to each as a single polypeptide chain, the VH and VL domains associate non-covalently. The scFv antibodies and a number of other structures converting the naturally aggregated, but chemically separated light and heavy polypeptide chains from an antibody V region into a molecule that folds into a three dimensional structure substantially similar to the structure of an antigen-binding site are known to those of skill in the art (see e.g., U.S. Pat. Nos. 5,091,513, 5,132,405, and 4,956,778).

The term "chemokine" is used herein to refer to any polypeptide, the wild-type form of which is secreted protein that has one or more pairs of conserved cysteines and that is a chemoattractant for leukocytes. The term encompasses "C (γ) chemokines," "CC (β) chemokines," "CXC (α) chemokines," and "CX$_3$C chemokines." The C chemokines contain only one pair of conserved cysteines, whereas the other chemokine types that have been characterized contain two pairs of conserved cysteines that form two disulfide bonds. These chemokines are subdivided based on the positions of the first two cysteines. These cysteines are adjacent in the CC chemokines, separated by a single amino acid in the CXC chemokines, and separated by three amino acids in the CX$_3$C chemokines.

The term "chemokine" includes full-length, wild-type polypeptides, as well as amino acid sequence variants thereof or other derivatives thereof. Similarly, the term "chemokine fragment" includes fragments of wild-type polypeptides, amino acid variants or other derivatives thereof, such as cyclic peptides.

A chemokine fragment or an amino acid sequence variant or other derivative thereof is said to be "derived from" the chemokine with which the chemokine fragment, variant, or derivative shares the greatest sequence homology. In this context, the term "derived from" is not intended to indicate that the fragment was obtained by modification of the chemokine. "Derived from" indicates a sequence relationship, not a source.

An "ELR motif" refers to the amino acid sequence: glutamate-leucine-arginine. A CXC chemokine that contains an ELR motif is referred to as an "ELR-CXC chemokine (ELR-CXC)," whereas a CXC chemokine that does not contain this motif is termed a "non-ELR-CXC chemokine" or referred to as "non-ELR-CXC." Examples of ELR-CXC chemokines include cCAF, IL-8, ENA-78, GCP-2, gro-α, -β, and -γ, CTAP-III, NAP-2 and β-TG. Examples of non-ELR-CXC chemokines include IP-10, MIG and PF4.

The term "angiogenic" is defined herein as the process of new blood vessel growth. An agent is angiogenic if treatment of a tissue with the agent results in an increase in the number of blood vessels present in the tissue, as compared to unteated tissue of the same type. Angiogenesis can be assessed in the chicken chorioallantoic membrane assay.

As used herein, the phrase "inducing the differentiation of fibroblasts to myofibroblasts" refers to the induction of at least one phenotypic characteristic of myofibroblasts. For example, α-smooth muscle actin is a marker of myofibroblasts that is markedly less abundant in fibroblasts than in myofibroblasts. Accordingly, the induction of α-SMA expression is one indicator of the induction of differentiation of fibroblasts to myofibroblasts.

A chemokine that is capable of inducing the differentiation of fibroblasts to myofibroblasts is termed a "differentiation-inducing chemokine."

A portion of a differentiation-inducing chemokine that is capable of inducing the differentiation of fibroblasts to myofibroblasts is termed a "differentiation-inducing domain."

An agent is said to "inhibit the differentiation of fibroblasts to myofibroblasts" if treatment of fibroblasts with the agent, under conditions that would otherwise favor differentiation to myofibroblasts, results in a reduction in the number of cells exhibiting at least one phenotypic characteristic of myofibroblasts, as compared with untreated fibroblasts under the same conditions. Such an agent is referred to herein as "an inhibitor."

The phrases "an effective amount" and "an amount sufficient to" refer to amounts of a biologically active agent to produce an intended biological activity.

A physiological condition is said to be "ameliorated" if there is any improvement in the condition, regardless of whether the improvement stems from an effect on a symptom of the condition or an underlying cause of the conditions.

A physiological condition is "characterized by a deficiency of myofibroblasts" if the presence of fewer than normal myofibroblasts contributes to the condition.

A physiological condition is "characterized by excess myofibroblasts" if the presence of fewer than normal myofibroblasts contributes to the condition.

Wound healing is "promoted" by an agent or event if the extent of wound healing is greater, or if wound healing is accelerated, compared to wound healing in the absence of the agent or event.

As used herein, the term "therapeutic" encompasses prophylaxis; i.e., "therapeutic" treatments include those aimed at preventing a pathological condition, as well as those aimed at ameliorating the condition.

The term "vector" is used herein to describe a DNA construct containing a nucleic acid molecule. Such a vector can be propagated stably or transiently in a host cell. The vector can, for example, be a plasmid, a viral vector, or simply a potential genomic insert. Once introduced into a suitable host, the vector may replicate and function independently of the host genome, or may, in some instances, integrate into the host genome.

As used herein, the term "operably linked" refers to a functional linkage between a control sequence (typically a promoter) and the linked sequence. For example, a promoter is operably linked to a sequence if the promoter can initiate transcription of the linked sequence.

"Expression vector" refers to a DNA construct containing a nucleic acid molecule that is operably linked to a control sequence capable of effecting the expression of the nucleic acid molecule in a suitable host. Exemplary control sequences include a promoter to effect transcription, an optional operator sequence to control transcription, a sequence encoding suitable mRNA ribosome binding sites, and sequences that control termination of transcription and translation.

The term "host cell" refers to a cell capable of maintaining a vector either transiently or stably. Host cells of the invention include, but are not limited to, bacterial cells, yeast cells, insect cells, plant cells and mammalian cells. Other host cells known in the art, or which become known, are also suitable for use in the invention.

As used herein, the term "complementary" refers to the capacity for precise pairing between two nucleotides. I.e., if a nucleotide at a given position of a nucleic acid molecule is capable of hydrogen bonding with a nucleotide of another nucleic acid molecule, then the two nucleic acid molecules are considered to be complementary to one another at that position. The term "substantially complementary" describes sequences that are sufficiently complementary to one another to allow for specific hybridization under stringent hybridization conditions.

The phrase "stringent hybridization conditions" generally refers to a temperature about 5° C. lower than the melting temperature ($T_m$) for a specific sequence at a defined ionic strength and pH. Exemplary stringent conditions suitable for achieving specific hybridization of most sequences are a temperature of at least about 60° C. and a salt concentration of about 0.2 molar at pH7.

"Specific hybridization" refers to the binding of a nucleic acid molecule to a target nucleotide sequence in the absence of substantial binding to other nucleotide sequences present in the hybridization mixture under defined stringency conditions. Those of skill in the art recognize that relaxing the stringency of the hybridization conditions allows sequence mismatches to be tolerated.

The term "array" refers to a collection of elements, wherein each element is uniquely identifiable. For example, the term can refer to a substrate bearing an arrangement of elements, such that each element has a physical location on the surface of the substrate that is distinct from the location of every other element. In such an array, each element can be identifiable simply by virtue of its location. Typical arrays of this type include elements arranged linearly or in a two-dimensional matrix, although the term "array" encompasses any configuration of elements and includes elements arranged on non-planar, as well as planar, surfaces. Non-planar arrays can be made, for example, by arranging beads, pins, or fibers to form an array. The term "array" also encompasses collections of elements that do not have a fixed relationship to one another. For example, a collection of beads in which each bead has an identifying characteristic can constitute an array.

The elements of an array are termed "target elements."

As used herein with reference to target elements, the term "distinct location" means that each element is physically separated from every other target element such that a signal (e.g., a fluorescent signal) from a labeled molecule bound to target element can be uniquely attributed to binding at that target element.

As used herein, an immunoassay is an assay that utilizes an antibody to specifically bind to the analyte. The immunoassay is thus characterized by detection of specific binding of a protein, or protein fragment, to a specific antibody as opposed to the use of other physical or chemical properties to isolate, target, and quantify the analyte.

II. Differentiation-Inducing Chemokine Polypeptides

The invention is based on the discovery that chemokines, and in particular, a domain at the N-terminus of chemokines, can induce the differentiation of fibroblasts to myofibroblasts. This process is important in wound healing and promotes wound contraction. Accordingly the invention provides differentiation-inducing chemokine polypeptides that are useful as research tools for studying the process of differentiation for fibroblasts to myofibroblasts. In addition, such polypeptides also have therapeutic applications, such as for example in conditions characterized by myofibroblast deficiency.

A. Polypeptides

A polypeptide of the invention includes a chemokine fragment that induces the differentiation of fibroblasts to myofibroblasts by virtue of a specific differentiation domain. The differentiation domain is a relatively short domain (on the order of about 8 to about 15 amino acids) that is generally found at the N-terminus of differentiation-inducing chemokines. Accordingly, the chemokine fragment used in the polypeptides of the invention is generally an N-terminal chemokine fragment. In ELR-CXC chemokines, this differentiation domain is located in a sequence of amino acids that includes the ELR motif, and thus chemokine fragments derived from ELR-CXC chemokines preferably include the ELR motif.

In addition to the chemokine fragment, polypeptides of the invention can include other amino acid sequences from the same or different chemokines or from other heterologous proteins. Accordingly, the invention encompasses fusion polypeptides in which a chemokine fragment is fused, at either or both ends, to amino acid sequence(s) from one or more heterologous proteins. Polypeptides of the invention generally do not include the full-length, wild-type chemokine.

The chemokine fragment can be derived from any differentiation-inducing chemokine from any organism having such chemokines. Chemokines useful in the invention are generally those derived from vertebrates, preferably from birds or mammals, more preferably from animals having research or commercial value or value as pets, such as mice, rats, guinea pigs, rabbits, cats, dogs, chickens, pigs, sheep, goats, cows, horses, as well as monkeys and other primates. In most preferred embodiments, the chemokine fragment is derived from a human chemokine.

Chemokines from any chemokine family can be employed, but, in one embodiment the chemokine fragment is preferably derived from a CXC chemokine. Examples of CXC chemokines suitable for used in the invention include chicken chemotactic and angiogenic factor (cCAF)/9E3/CEF4, interleukin-8 (IL-8)/NAP1, melanoma growth stimulatory activity (MGSA)/groα, epithelial-derived neutrophil attractant-78 (ENA-78), granulocyte chemotactic protein-2 (GCP-2), macrophage inflammatory protein-2β (MIP-2β)/gro-γ, connective tissue activating peptide III (CTAP-III), neutrophil activating peptide-2 (NAP-2), β-thromboglobulin (β-TG), interferon-γ-inducible protein-10 (IP-10), monokine induced by interferon-γ (Mig), and platelet factor 4 (PF4). Preferably, the chemokine is a CXC chemokine having an ELR motif (i.e., a member of the "ELR-CXC" chemokine family). Examples of ELR-CXC chemokines include cCAF, IL-8, ENA-78, GCP-2, gro-α, -β, and -γ, CTAP-III, NAP-2, and βTG.

In another preferred embodiment, the chemokine is a CC chemokine, more preferably a monocyte chemoattractant protein (MCP). In a specific preferred embodiment, the chemokine is MCP-1, which, like cCAF, has an N-terminal domain that mediates its chemoattractant effects.

Chemokine polypeptides derived from the CXC chemokines IL-8, cCAF, and MSGA are particularly preferred for use in the invention. The nucleotide sequences of these chemokines are shown in Table 1.

TABLE 1

DEFINITION: Chicken embryo fibroblast protein mRNA, complete cds.
GenBank ACCESSION: M16199 nntcagcaatcctctgacaggagagatcacagctccacaaaacctcagctcagaaaacaagccaaacactcctaaccatgaacggc (SEQ ID NO:1)

aagcttggagctgtcctggccctcctcctggtttcagctgctctgtcgcaaggtaggacgctggtaaagatggggaatgagctgcggt gccagtgcattagcactcattctaagttcatccaccctaaatccattcaagatgtgaagctgacgccaagcggccccccactgcaagaat gttgaaatcatagctactctaaaggatggaagagaggtgtgcttggaccccactgctccctgggtacagctgatcgtaaaggcacttat ggccaaggctcagctcaattctgatgcaccactgtgagaaaattccagacaggaaaaatcctcagaactgctcctgatttctactggga gaaacatccgaagaaggcatcatgaagcattccatcttccaccttccacatcggtgcctcatgttaattgcagatccttgtatctattta atttatttatttaactgcatgtatttaaaaaagtcttttcataatggtcagtgctgtgggattcactgtccagtgaaactgaagacactgaa tagcaaaagggcttgctaggggaaatgaagatcccttggaagccacttcagtcagacacaatcagttaagtgcaatgcacttacagcaca gcttgtttgtattaagccctactgtgttgctattacagcagcaaactggtaattcctcctgctccctggagtgctctagtatgttgtgt caacaacagtttcctagtcagagtcagctcatgccgactgcagactgtgtttaaaacttcagaaatctaacctgcagaatctgtaagact gtgggtttggtatttattatgatttccatggtatttataaatatatttatttactagtttctatacaagatggaaggagatgataacttg tgtaaatttctactggattttctgttcttaatgatgaatacttaagaaacattcacatacccattactctgcataaggacttggttctatg tctaatacgtgagttattcagctaatggaaaaaaaactacagcatgcatacacagaatttgcttgtgagaatgtaattacctcttacaat atattaataaatattttattt DEFINITION: Homo sapiens interleukin 8 (IL8), mRNA.
GenBank ACCESSION: XM_003501 agcagagcacacaagcttctaggacaagagccaggaagaaaccaccggaaggaaccatctcactgtgtgtaaacatgacttccaag (SEQ ID NO:3)

ctggccgtggctctcttggcagccttcctgatttctgcagctctgtgtgaaggtgcagttttgccaaggagtgctaaagaacttagatgt cagtgcataaagacatactccaaaccttccaccccaaatttatcaaagaactgagagtgattgagagtggaccacactgcgccaacac agaaattattgtaaagctttctgatggaagagagctctgtctggaccccaaggaaaactgggtgcagagggttgtggagaagttttga agagggctgagaattcataaaaaaattcattctctgtggtatccaagaatcagtgaagatgccagtgaaacttcaagcaaatctacttca acacttcatgtattgtgtgggtctgttgtagggttgccagatgcaatacaagattcctggttaaatttgaatttcagtaaacaatgaata gttttcattgtaccatgaaatatccagaacatacttatatgtaaagtattatttatttgaatctacaaaaaacaacaaataattttaa atataaggattttcctagatattgcacgggagaatatacaaatagcaaaattgaggccaagggccaagagaatatccgaactttaatttc TABLE 1-continued aggaattgaatgggtttgctagaatgtgatatttgaagcatcacataaaaatgatgggacaataaattttgccataaagtcaatttagc
tggaaatcctggattttttctgttaaatctggcaaccctagtctgctagccaggatccacaagtccttgttccactgtgccttggtttc
tcctttatttctaagtggaaaaagtattagccaccatcttacctcacagtgatgttgtgaggacatgtggaagcactttaagttttttca
tcataacataaattattttcaagtgtaacttattaacctatttattatttatgtatttatttaagcatcaaatatttgtgcaagaatttg
gaaaaatagaagatgaatcattgattgaatagttataaagatgttatagtaaatttattttattttagatattaaatgatgttttattag
ataaatttcaatcagggttttagattaaacaaacaaacaattgggtacccagttaaattttcatttcagataaacaacaaataattttt
tagtataagtacattattgtttatctgaaattttaattgaactaacaatcctagtttgatactcccagtcttgtcattgccagctgtgtt
ggtagtgctgtgttgaattacggaataatgagttagaactattaaaacagccaaaactccacagtcaatattagtaatttcttgctggtt
gaaacttgtttattatgtacaaatagattcttataatattatttaaatgactaaatatgaaacatttaaaatataatttgttgtcaaagt
aatcaagtg DEFINITION: Homo sapiens GRO1 oncogene (melanoma growth stimulating activity,
alpha) (GRO1), mRNA.
Genbank ACCESSION: XM_003504

Acagagcccgggccgcaggcacctcctcgccagctcttccgctcctctcacagccgccagacccgcctgctgagccccatggccc  (SEQ ID NO:6)
gcgctgctctctccgccgccccagcaatccccggctcctgcgagtggcgctgctgctcctgctcctggtagccgctggccggcgc
gcagcaggagcgtccgtggccactgaactgcgctgccagtgcttgcagaccctgcagggaattcaccccaagaacatccaaagtgt
gaacgtgaagtccccggacccactgcgcccaaaccgaagtcatagccacactcaagaatgggcggaaagcttgcctcaatcctg
catccccatagttaagaaaatcatcgaaaagatgctgaacagtgacaaatccaactgaccagaagggaggaggaagctcactggt
ggctgttcctgaaggaggccctgcccttataggaacagaagaggaaagagagacacagctgcagaggccacctggattgtgcctaa
tgtgtttgagcatcgcttaggagaagtcttctatttatttatttattcattagttttgaagattctatgttaatattttaggtgtaaaat
aattaagggtatgattaactctacctgcacactgtcctattatattcattcttttttgaaatgtcaacccccaagttagttcaatctggatt
catatttaatttgaaggtagaatgttttcaaatgttctccagtcattatgttaatatttctgaggagcctgcaacatgccagccactgtg
atagaggctggcggatccaagcaaatggccaatgagatcattgtgaaggcaggggaatgtatgtgcacatctgttttgtaactgtttaga
tgaatgtcagttgttatttattgaaatgatttcacagtgtgtggtcaacatttctcatgttgaaactttaagaactaaaatgttctaaat
atcccttggacattttatgtctttcttgtaaggcatactgccttgtttaatggtagttttacagtgtttctggcttagaacaaaggggct
taattattgatgttttcatagagaatataaaaataaagcacttatag The amino acid sequences of two forms of IL-8 (IL-8-72 and IL-8-77) and of cCAF and MSGA are given in Table 2 (using single-letter amino acid code). The IL-8-77 form is more potent at inducing differentiation of fibroblasts to myofibroblasts and is therefore a preferred source of IL-8-derived polypeptides of the invention.

TABLE 2

IL-8-72:
SAKELRCQCIKTYSKPFHPKFIKELRVIESGPHCAN     (SEQ ID NO:5)
TEIIVKLSDGRELCLDPKENWVQRVVEKFLKRAE
NS

IL-8-77
AVLPRSAKELRCQCIKTYSKPFHPKFIKELRVIESG     (SEQ ID NO:4)
PHCANTEIIVKLSDGRELCLDPKENWVQRVVEKFL
KRAENS cCAF:
LSQGRTLVKMGNELRCQCISTHSKFIHPKSIQDVK      (SEQ ID NO:2)
LTPSGPHCKNVEIIATLKDGREVCLDPTAPWVQLI
VKALMAKAQLNSDAPL

TABLE 2-continued

MGSA:
ASVATELRCQCLQTLQGIHPKNIQSVNVKSPGPHC      (SEQ ID NO:7)
AQTEVIATLKNGRKACLNPASPIVKKIIEKMLNSD
KSN

The chemokine fragment must be large enough to include a functional differentiation domain. Chemokine fragments useful in the invention can, for example, range from about 5 to about 50 amino acids in length, although other lengths are possible. Preferred fragments range from about 8 to about 25 amino acids, and more preferably from about 8 to about 15 amino acid.

The amino acid sequence of the chemokine fragment can be a wild-type amino acid sequence. However, the polypeptide of the invention differs from the wild-type chemokine, for example, in lacking wild-type amino acid sequence(s) N- and/or C-terminal to the chemokine fragment (e.g., one or more amino acid residues has been added, deleted, or substituted with a different amino acid). In particular embodiments, one or more other functional domains present in the wild-type chemokine is deleted or disrupted by the addition, deletion, or substitution of one or more amino acids. The resultant polypeptides have the ability to induce differentiation, but lack one or more other functions of the wild-type chemokine. For example, the CXC chemokine cCAF stimulate angiogenisis via a C-terminal domain, which is found at residues 59–86 of cCAF (SEQ ID NO:2). A preferred polypeptide of the invention lacks this domain and is therefor not angiogenic.

Examples of preferred chemokine fragments that have wild-type amino acid sequences are shown in Table 3 (using single-letter amino acid code).

TABLE 3

| | | |
|---|---|---|
| IL-8-72: | | |
| SAKELR | (SEQ ID NO:8) | |
| IL-8-77: | | |
| AVLPRSAKELR | (SEQ ID NO:9) | |
| cCAF: | | |
| LSQGRTLVKMGNELR | (SEQ ID NO:10) | |
| MGSA: | | |
| ASVATELR | (SEQ ID NO:11) | |

The chemokine fragment can also be an amino acid sequence variant of the corresponding region of a wild-type chemokine. Such fragments preferably share at least about 70% sequence identity, more preferably at least about 80% sequence identity, and most preferably at least about 90% sequence identity with the corresponding region of a wild-type chemokine. For example, preferred variant chemokine fragments are at least about 70%, preferably at least about 80%, more preferably at least about 90%, and most preferably at least about 95%, identical to an N-terminal amino acid sequence of IL-8, cCAF, or MGSA.

In the above embodiment, variant chemokine fragments retain the ability to induce differentiation of fibroblasts to myofibroblasts (agonist variants). Accordingly, preferred polypeptides generally have a wild-type amino acid sequence or conservative changes in the differentiation domain. Preferably, any amino acid substitutions in the differentiation domain are conservative amino acid substitutions, as defined above.

Polypeptides of the invention can be otherwise modified to produce derivatives that retain the ability to induce differentiation fibroblasts to myofibroblasts. In preferred embodiments, the modified polypeptides have an activity that is about 0.1 to about 0.01-fold that of the unmodified forms. In more preferred embodiments, the modified polypeptides have an activity that is about 0.1 to about 1-fold that of the unmodified peptides. In even more preferred embodiments, the derivatized peptides have an activity that is greater than the unmodified peptides.

Those of skill in the art recognize that a variety of techniques are available for constructing so-called "peptide mimetics" with the same or similar desired biological activity as the corresponding peptide compound, but with more favorable activity than the peptide with respect to, e.g., solubility, stability, and susceptibility to hydrolysis and proteolysis. See, for example, Morgan, et al., Ann. Rep. Med. Chem., 24:243–252 (1989). The following describes methods for preparing peptide mimetics modified at the N-terminal amino group, the C-terminal carboxyl group, and/or changing one or more of the amido linkages in the peptide to a non-amido linkage. It being understood that two or more such modifications can be coupled in one peptide mimetic structure (e.g., modification at the C-terminal carboxyl group and inclusion of a —$CH_2$-carbamate linkage between two amino acids in the peptide).

The peptides typically are synthesized as the free acid but could be readily prepared as the amide or ester. One can also modify the amino and/or carboxy terminus of peptides. Amino terminus modifications include alkylation, e.g., methylation (—$NHCH_3$ or —$NH(CH_3)_2$); acetylation, adding a carbobenzoyl group or a benzyloxycarbonyl group; forming a succinimide group ;or blocking the amino terminus with any blocking group containing a carboxylate functionality defined by RCOO—, where R is selected from the group consisting of naphthyl, acridinyl, steroidyl, and similar groups; etc. (See, e.g., Murray, et al., Burger's Medicinal Chemistry and Drug Discovery, 5th ed., Vol. 1, Manfred E. Wolf, ed., John Wiley and Sons, Inc. (1995).)

C-terminal modifications include, for example,replacing the C-terminal carboxyl group with an ester, an amide. In preparing peptide mimetics wherein the C-terminal carboxyl group is replaced by an ester (i.e., —C(O)OR where R is as defined above), the resins used to prepare the peptide acids are employed, and the side chain protected peptide is cleaved with base and the appropriate alcohol, e.g., methanol. Side chain protecting groups are then removed in the usual fashion by treatment with hydrogen fluoride to obtain the desired ester.

To prepare peptide mimetics wherein the C-terminal carboxyl group is replaced by an amide, a benzhydrylamine resin can be used as the solid support for peptide synthesis. Upon completion of the synthesis, hydrogen fluoride treatment to release the peptide from the support results directly in the free peptide amide (i.e., the C-terminus is —C(O) $NH_2$). Alternatively, use of the chloromethylated resin during peptide synthesis coupled with reaction with ammonia to cleave the side chain protected peptide from the support yields the free peptide amide and reaction with an alkylamine or a dialkylamine yields a side chain protected alkylamide or dialkylamide. Side chain protection is then removed in the usual fashion by treatment with hydrogen fluoride to give the free amides, alkylamides, or dialkylamides.

In another alternative embodiment, the C-terminal carboxyl group or a C-terminal ester can be induced to cyclize by internal displacement of the —OH or the ester (—OR) of the carboxyl group or ester respectively with the N-terminal amino group to form a cyclic peptide. For example, after synthesis and cleavage to give the peptide acid, the free acid is converted to an activated ester by an appropriate carboxyl group activator such as dicyclohexylcarbodiimide (DCC) in solution, for example, in methylene chloride ($CH_2Cl_2$), dimethyl formamide (DMF) mixtures. The cyclic peptide is then formed by internal displacement of the activated ester with the N-terminal amine. Internal cyclization as opposed to polymerization can be enhanced by use of very dilute solutions. Such methods are well known in the art.

One can also cyclize the peptides of the invention, or incorporate a desamino or descarboxy residue at the terminii of the peptide, so that there is no terminal amino or carboxyl group, to decrease susceptibility to proteases or to restrict the conformation of the peptide. C-terminal functional groups of the compounds of the present invention include amide, amide lower alkyl, amide di(lower alkyl), lower alkoxy, hydroxy, and carboxy, and the lower ester derivatives thereof, and the pharmaceutically acceptable salts thereof.

In addition to the foregoing N-terminal and C-terminal modifications, the polypeptides of the invention, including peptidomimetics, can advantageously be modified with or covalently coupled to one or more of a variety of hydrophilic polymers. It has been found that when the peptide compounds are derivatized with a hydrophilic polymer, their solubility and circulation half-lives are increased and their immunogenicity is masked. These advantages can be acheived with little, if any, loss of binding activity. Non-proteinaceous polymers suitable for use in accordance with the present invention include, but are not limited to, poly-alkylethers as exemplified by polyethylene glycol and polypropylene glycol, polylactic acid, polyglycolic acid, polyoxyalkenes, polyvinylalcohol, polyvinylpyrrolidone, cellulose and cellulose derivatives, dextran and dextran derivatives, etc. Generally, such hydrophilic polymers have an average molecular weight ranging from about 500 to about 100,000 daltons, more preferably from about 2,000 to about 40,000 daltons and, even more preferably, from about 5,000 to about 20,000 daltons. In preferred embodiments, such hydrophilic polymers have an average molecular weights of about 5,000 daltons, 10,000 daltons and 20,000 daltons.

The polypeptides of the invention can be derivatized with or coupled to such polymers using any of the methods set forth in Zallipsky, S., Bioconjugate Chem., 6:150–165 (1995); Monfardini, C, et al., Bioconjugate Chem., 6:62–69 (1995); U.S. Pat. No. 4,640,835; U.S. Pat. No. 4,496,689; U.S. Pat. No. 4,301,144; U.S. Pat. No. 4,670,417; U.S. Pat. No. 4,791,192; U.S. Pat. No. 4,179,337 or WO 95/34326.

Other methods for making derivatives of the polypeptides of the present invention are described in Hruby, et al., Biochem J., 268(2):249–262 (1990). In particular, the peptide compounds of the invention also serve as structural models for non-peptidic compounds with similar biological activity. Those of skill in the art recognize that a variety of techniques are available for constructing compounds with the same or similar desired biological activity as the lead polypeptide but with more favorable activity than the lead with respect to solubility, stability, and susceptibility to hydrolysis and proteolysis. See Morgan, et al., Ann. Rep. Med. Chem., 24:243–252 (1989), incorporated herein by reference. These techniques include replacing the peptide backbone with a backbone composed of phosphonates, amidates, carbamates, sulfonamides, secondary amines, and N-methylamino acids.

Peptide mimetics wherein one or more of the peptidyl linkages [—C(O)NH—] have been replaced by such linkages as a —$CH_2$-carbamate linkage, a phosphonate linkage, a —$CH_2$-sulfonamide linkage, a urea linkage, a secondary amine (—$CH_2$NH—) linkage, and an alkylated peptidyl linkage [—C(O)NR— where R is lower alkyl] are prepared during conventional peptide synthesis by merely substituting a suitably protected amino acid analogue for the amino acid reagent at the appropriate point during synthesis.

Suitable reagents for use in the invention include, for example, amino acid analogues wherein the carboxyl group of the amino acid has been replaced with a moiety suitable for forming one of the above linkages. For example, if one desires to replace a —C(O)NR— linkage in the peptide with a —$CH_2$-carbamate linkage (—$CH_2$OC(O)NR—), then the carboxyl (—COOH) group of a suitably protected amino acid is first reduced to the —$CH_2$OH group which is then converted by conventional methods to a —OC(O)Cl functionality or a para-nitrocarbonate —OC(O)O—$C_6H_4$-p-$NO_2$ functionality. Reaction of either of such functional groups with the free amine or an alkylated amine on the N-terminus of the partially fabricated peptide found on the solid support leads to the formation of a —$CH_2$OC(O)NR— linkage. For a more detailed description of the formation of such —$CH_2$-carbamate linkages, see Cho, et al., Science, 261:1303–1305 (1993).

Replacement of an amido linkage in the peptide with a —$CH_2$-sulfonamide linkage can be achieved by reducing the carboxyl (—COOH) group of a suitably protected amino acid to the —$CH_2$OH group and then converting the hydroxyl group to a suitable leaving group (such as, e.g., a tosyl group) by conventional methods. Reaction of the tosylated derivative with, for example, thioacetic acid followed by hydrolysis and oxidative chlorination will provide for the —$CH_2$—$S(O)_2$Cl functional group which replaces the carboxyl group of the otherwise suitably protected amino acid. Use of this suitably protected amino acid analogue in peptide synthesis provides for inclusion of an —$CH_2S(O)_2$NR— linkage which replaces the amido linkage in the peptide thereby providing a peptide mimetic. For a more complete description on the conversion of the carboxyl group of the amino acid to a —$CH_2S(O)_2$Cl group, see, for example, Weinstein, B., Chemistry & Biochemistry of Amino Acids, Peptides and Proteins, Vol. 7, pp. 267–357, Marcel Dekker, Inc., New York (1983).

Secondary amine linkages wherein a —$CH_2$NH— linkage replaces the amido linkage in the peptide can be prepared by employing, for example, a suitably protected dipeptide analogue wherein the carbonyl bond of the amido linkage has been reduced to a $CH_2$ group by conventional methods. For example, in the case of diglycine, reduction of the amide to the amine will yield after deprotection $H_2NCH_2CH_2NHCH_2COOH$ which is then used in N-protected form in the next coupling reaction. The preparation of such analogues by reduction of the carbonyl group of the amido linkage in the dipeptide is well known in the art (see, e.g., Michael W. Remington, Meth. in Mol. Bio., 35:241–247 (1994)).

The suitably protected amino acid analogue is employed in the conventional peptide synthesis in the same manner as would the corresponding amino acid. For example, typically about 3 equivalents of the protected amino acid analogue are employed in this reaction. An inert organic diluent such as methylene chloride or DMF is employed and, when an acid is generated as a reaction by-product, the reaction solvent will typically contain an excess amount of a tertiary amine to scavenge the acid generated during the reaction. One particularly preferred tertiary amine is diisopropylethylamine which is typically employed in about 10 fold excess. The reaction results in incorporation into the peptide mimetic of an amino acid analogue having a non-peptidyl linkage. Such substitution can be repeated as desired such that from zero to all of the amido bonds in the peptide have been replaced by non-amido bonds.

One can also cyclize the peptides of the invention so that there is no terminal amino or carboxyl group, to decrease susceptibility to proteases or to restrict the conformation of the peptide.

In one embodiment, disulfide bonds bond between the thiol groups of cysteines are manipulated to produce polypeptides of the desired conformation. Intramolecular disulfide bonds can be used to produce a cyclized form. Alternatively, an intermolecular disulfide bond can be employed to yield a dimeric (or higher oligomeric) compound. One or more of the cysteine residues may also be substituted with a homocysteine. Other embodiments of this invention provide for analogs of these disulfide derivatives in which one of the sulfurs has been replaced by a $CH_2$ group or other isostere for sulfur. These analogs can be made via an intramolecular or intermolecular displacement, using methods known in the art. One of skill in the art will readily appreciate that this displacement can also occur using other homologs of the a-amino-g-butyric acid derivative shown above and homocysteine (see, e.g., Frank A. Robey, Meth. in Mol. Bio., 35(6):73–90 (1990).

Alternatively, the amino-terminus of the peptide can be capped with an alpha-substituted acetic acid, wherein the alpha substituent is a leaving group, such as an a-haloacetic acid, for example, a-chloroacetic acid, a-bromoacetic acid, or a-iodoacetic acid. The compounds of the present invention can be cyclized or dimerized via displacement of the leaving group by the sulfur of the cysteine or homocysteine residue. See, e.g., Andreu, et al., Meth. in Mol. Bio., 35(7):91–169 (1994); Barker, et al., J. Med. Chem., 35:2040–2048 (1992) and Or, et al., J. Org. Chem., 56:3146–3149 (1991).

B. Production of Chemokine Polypeptides

1. Synthetic Techniques

Chemokine polypeptides according to the invention can be synthesized using methods known in the art, such as for example exclusive solid phase synthesis, partial solid phase synthesis methods, fragment condensation, and classical solution synthesis. See, e.g., Merrifield, J. Am. Chem. Soc., 85:2149 (1963). Solid phase techniques are preferred. On solid phase, the synthesis typically begins from the C-terminal end of the peptide using an alpha-amino protected resin. A suitable starting material can be prepared, for instance, by attaching the required alpha-amino acid to a chloromethylated resin, a hydroxymethyl resin, or a benzhydrylamine resin. One such chloromethylated resin is sold under the tradename BIO-BEADS SX-1 by Bio Rad Laboratories, Richmond, Calif., and the preparation of the hydroxymethyl resin is described by Bodonszky, et al., Chem. Ind. (London), 38:1597 (1966). The benzhydrylamine (BHA) resin has been described by Pietta and Marshall, Chem. Commn., 650 (1970) and is commercially available from Beckman Instruments, Inc., Palo Alto, Calif., in the hydrochloride form. Automated peptide synthesizers are commercially available as are services that make peptides to order.

Thus, the compounds of the invention can be prepared by coupling an alpha-amino protected amino acid to the chloromethylated resin with the aid of, for example, cesium bicarbonate catalyst, according to the method described by Gisin, Helv. Chim. Acta., 56:1467 (1973). After the initial coupling, the alpha-amino protecting group is removed by a choice of reagents including trifluoroacetic acid (TFA) or hydrochloric acid (HCl) solutions in organic solvents at room temperature.

The alpha-amino protecting groups are those known to be useful in the art of stepwise synthesis of peptides. Included are acyl type protecting groups (e.g., formyl, trifluoroacetyl, acetyl), aromatic urethane type protecting groups (e.g. benzyloxycarboyl (Cbz) and substituted Cbz), aliphatic urethane protecting groups (e.g., t-butyloxycarbonyl (Boc), isopropyloxycarbonyl, cyclohexyloxycarbonyl) and alkyl type protecting groups (e.g., benzyl, triphenylmethyl). Boc and Fmoc are preferred protecting groups. The side chain protecting group remains intact during coupling and is not split off during the deprotection of the amino-terminus protecting group or during coupling. The side chain protecting group must be removable upon the completion of the synthesis of the final peptide and under reaction conditions that will not alter the target peptide.

After removal of the alpha-amino protecting group, the remaining protected amino acids are coupled stepwise in the desired order. An excess of each protected amino acid is generally used with an appropriate carboxyl group activator such as dicyclohexylcarbodiimide (DCC) in solution, for example, in methylene chloride, dimethyl formamide (DMF) mixtures.

After the desired amino acid sequence has been completed, the desired peptide is decoupled from the resin support by treatment with a reagent such as trifluoroacetic acid or hydrogen fluoride (HF), which not only cleaves the peptide from the resin, but also cleaves all remaining side chain protecting groups. When the chloromethylated resin is used, hydrogen fluoride treatment results in the formation of the free peptide acids. When the benzhydrylamine resin is used, hydrogen fluoride treatment results directly in the free peptide amide. Alternatively, when the chloromethylated resin is employed, the side chain protected peptide can be decoupled by treatment of the peptide resin with ammonia to give the desired side chain protected amide or with an alkylamine to give a side chain protected alkylamide or dialkylamide. Side chain protection is then removed in the usual fashion by treatment with hydrogen fluoride to give the free amides, alkylamides, or dialkylamides.

These solid phase peptide synthesis procedures are well known in the art and further described by John Morrow Stewart and Janis Dillaha Young, Solid Phase Peptide Syntheses (2nd Ed., Pierce Chemical Company, 1984).

2. Recombinant Techniques

Chemokine polypeptides can also produced using recombinant techniques. Precursor chemokine genes or gene sequences can be cloned, for instance, based on homology to known chemokines, such as those described above. With a precursor chemokine gene in hand, a nucleic acid molecule encoding a desired chemokine polypeptide can be generated by any of a variety of mutagenesis techniques. See, e.g., Sambrook, J., Fritsch, E. F., and Maniatis, T. (1989) in Molecular Cloning: A Laboratory Manual, Second Edition, Cold Spring Harbor, N.Y. Examples include site-specific mutagenesis (Kunkel et al., (1991) Methods Enzymol., 204:125–139; Carter, P., et al., (1986) Nucl. Acids Res. 10:6487), cassette mutagenesis (Wells, J. A., et al., (1985) Gene 34:315), and restriction selection mutagenesis (Wells, J. A., et al., (1986) Philos. Trans. R. Soc., London Ser. A, 317:415).

In a preferred embodiment of the invention, the sequence of a chemokine coding region is used as a guide to design a synthetic nucleic acid molecule encoding the chemokine polypeptide that can be incorporated into a vector of the present invention. Methods for constructing synthetic genes are well-known to those of skill in the art. See, e.g., Dennis, M. S., Carter, P. and Lazarus, R. A. (1993) Proteins: Struct. Funct. Genet., 15:312–321. Expression and purification methods are described below in connection with the nucleic acids, vectors and host cells of the invention.

C. Uses of Polypeptides

The polypeptides of the invention are useful in a variety of research and therapeutic applications. The discovery of chemokine polypeptides that induce the differentiation of fibroblasts to myofibroblasts and accelerate wound contraction will facilitate studies aimed at elucidating the series of molecular events underlying these phenomena. In particular, the chemokine polypeptides of the invention can be used to induce differentiation in in vitro systems, which, for example, will allow controlled studies to be performed that investigate the roles of various known potential mediators of these phenomena.

In other research applications, the chemokine polypeptides of the invention can be used as controls in screening assays to identify additional molecules that stimulate or inhibit differentiation of fibroblasts to myofibroblasts or as standards, for example, in chemokine immunoassays.

Chemokine polypeptides can also be used therapeutically to treat a conditions characterized by a deficiency of myofibroblasts. For example, the lack of myofibroblasts after corneal surgery leads to corneal flattening and widening of the wound and also contributes to the non-contractility of fetal wounds.

Pharmaceutical compositions containing the chemokine polypeptides of the invention, as well as methods for inducing or inhibiting chemokine differentiation are described in greater detail below.

III. Nucleic Acids, Vector, and Host Cells

The invention also provides a nucleic acid molecule encoding a chemokine polypeptide of the invention, a vector including this nucleic acid molecule, and a host cell including the vector.

A. Nucleic Acid Molecules

The invention provides nucleic acid molecules encoding a chemokine polypeptide of the invention. Such nucleic acid molecules include a portion that encodes a chemokine fragment that induces differentiation of fibroblasts to myofibroblasts. As noted above, the amino acid sequence of this fragment can be a wild-type chemokine sequence or a variant sequence. Where the sequence of the chemokine fragment is a wild-type sequence, the nucleotide sequence encoding this fragment can be a wild-type nucleotide sequence or one containing "silent" mutations that do not alter the amino acid sequence due to the degeneracy of the genetic code. For example, if the nucleic acid molecule is intended for use in expressing the encoding polypeptide, silent mutations can be introduced by standard mutagenesis techniques to optimize codons to those preferred by the host cell.

In some applications, it is advantageous to stabilize the nucleic acid molecules described herein or to produce nucleic acid molecules that are modified to better adapt them for particular applications. To this end, the nucleic acid molecules of the invention can contain phosphorothioates, phosphotriesters, methyl phosphonates, short chain alkyl or cycloalkyl intersugar linkages or short chain heteroatomic or heterocyclic intersugar ("backbone") linkages. Most preferred are phosphorothioates and those with $CH_2$—NH—O—$CH_2$, $CH_2$—N($CH_3$)—O—$CH_2$ (known as the methylene(methylimino) or MMI backbone) and $CH_2$—O—N($CH_3$)—$CH_2$, $CH_2$—N($CH_3$)—N($CH_3$)—$CH_2$, and O—N($CH_3$)—$CH_2$—CH backbones (where phosphodiester is O—P—O—$CH_2$). Also preferred are nucleic acid molecules having morpholino backbone structures. Summerton, J. E. and Weller, D. D., U.S. Pat. No. 5,034,506. Other preferred embodiments use a protein-nucleic acid or peptide-nucleic acid (PNA) backbone, wherein the phosphodiester backbone of the nucleic acid molecule is replaced with a polyamide backbone, the bases being bound directly or indirectly to the aza nitrogen atoms of the polyamide backbone. P. E. Nielsen, M. Egholm, R. H. Berg, O. Buchardt, Science 1991, 254, 1497. Nucleic acid molecules of the invention can contain alkyl and halogen-substituted sugar moieties and/or can have sugar mimetics such as cyclobutyls in place of the pentofuranosyl group. In other preferred embodiments, the nucleic acid molecules can include at least one modified base form or "universal base" such as inosine. Nucleic acid molecules can, if desired, include an RNA cleaving group, a cholesteryl group, a reporter group, an intercalator, a group for improving the pharmacokinetic properties of the nucleic acid molecule, and/or a group for improving the pharmacodynamic properties of the nucleic acid molecule.

Those of skill in the art understand that nucleic acid molecules complementary to the coding strand of nucleic acid molecules of the invention can be employed to inhibit expression of the polypeptides of the invention, which may be of interest for research or therapeutic purposes. Accordingly, the nucleic acids of the invention include such "antisense nucleic acid molecules," and the phrase "nucleic acid molecule encoding a polypeptide of the invention" is intended to include such antisense molecules.

B. Vectors

A nucleic acid molecule of the present invention can be incorporated into a vector for propagation and/or expression in a host cell. Such vectors typically contain a replication sequence capable of effecting replication of the vector in a suitable host cell (i.e., an origin of replication) as well as sequences encoding a selectable marker, such as an antibiotic resistance gene. Upon transformation of a suitable host, the vector can replicate and function independently of the host genome or integrate into the host genome. Vector design depends, among other things, on the intended use and host cell for the vector, and the design of a vector of the invention for a particular use and host cell is within the level of skill in the art.

If the vector is intended for expression of a chemokine polypeptide, the vector includes one or more control sequences capable of effecting and/or enhancing the expression of an operably linked chemokine polypeptide coding sequence. Control sequences that are suitable for expression in prokaryotes, for example, include a promoter sequence, an operator sequence, and a ribosome binding site. Control sequences for expression in eukaryotic cells include a promoter, an enhancer, and a transcription termination sequence (i.e., a polyadenylation signal).

A chemokine expression vector can also include other sequences, such as, for example, nucleic acid sequences encoding a signal sequence or an amplifiable gene. A signal sequence directs the secretion of a polypeptide fused thereto from a cell expressing the protein. In the expression vector, nucleic acid encoding a signal sequence is linked to a chemokine polypeptide coding sequence so as to preserve the reading frame of the chemokine polypeptide coding sequence. The inclusion in a vector of a gene complementing an auxotrophic deficiency in the chosen host cell allows for the selection of host cells transformed with the vector.

A vector of the present invention is produced by linking desired elements by ligation at convenient restriction sites. If such sites do not exist, suitable sites can be introduced by standard mutagenesis (e.g., site-directed or cassette mutagenesis) or synthetic oligonucleotide adaptors or linkers can be used in accordance with conventional practice.

Viral vectors are of particular interest for use in delivering nucleic acid molecules of the invention to a cell or organism, followed by expression of the encoded protein, i.e., "gene therapy" when performed to ameliorate a pathological condition. For a review of gene therapy procedures, see, e.g., Anderson, *Science* (1992) 256: 808–813; Nabel and Felgner (1993) *TIBTECH* 11: 211–217; Mitani and Caskey (1993) *TIBTECH* 11: 162–166; Mulligan (1993) *Science,* 926–932; Dillon (1993) *TIBTECH* 11: 167–175; Miller (1992) *Nature* 357: 455–460; Van Brunt (1988) *Biotechnology* 6(10): 1149–1154; Vigne (1995) Restorative Neurology and Neuroscience 8: 35–36; Kremer and Perricaudet (1995) *British Medical Bulletin* 51(1) 31–44; Haddada et al. (1995) in *Current Topics in Microbiology and Immunology*, Doerfler and Böhm (eds) Springer-Verlag, Heidelberg Germany; and Yu et al., (1994) *Gene Therapy,* 1:13–26.

Widely used vector systems include, but are not limited to adenovirus, adeno associated virus, and various retroviral expression systems. The use of adenoviral vectors is well known to those of skill and is described in detail, e.g., in WO 96/25507. Particularly preferred adenoviral vectors are described by Wills et al. (1994) *Hum. Gene Therap.* 5: 1079–1088. Adenoviral vectors suitable for use in the invention are also commercially available. For example, the Adeno-X™ Tet-Off™ gene expression system, sold by Clontech, provides an efficient means of introducing inducible heterologous genes into most mammalian cells.

Adeno-associated virus (AAV)-based vectors used to transduce cells with target nucleic acids, e.g., in the in vitro production of nucleic acids and peptides, and in in vivo and ex vivo gene therapy procedures are describe, for example, by West et al. (1987) *Virology* 160:38–47; Carter et al. (1989) U.S. Pat. No. 4,797,368; Carter et al. WO 93/24641 (1993); Kotin (1994) *Human Gene Therapy* 5:793–801; Muzyczka (1994) *J. Clin. Invst.* 94:1351 for an overview of AAV vectors. Lebkowski, U.S. Pat. No. 5,173,414; Tratschin et al. (1985) *Mol. Cell. Biol.* 5(11):3251–3260; Tratschin, et al. (1984) *Mol. Cell. Biol.,* 4: 2072–2081; Hermonat and Muzyczka (1984) *Proc. Natl. Acad. Sci. USA,* 81: 6466–6470; McLaughlin et al. (1988) and Samulski et al. (1989) *J. Virol.,* 63:03822–3828. Cell lines that can be transformed by rAAV include those described in Lebkowski et al. (1988) *Mol. Cell. Biol.,* 8:3988–3996.

Widely used retroviral vectors include those based upon murine leukemia virus (MuLV), gibbon ape leukemia virus (GaLV), Simian Immunodeficiency virus (SIV), human immunodeficiency virus (HIV), alphavirus, and combinations thereof (see, e.g., Buchscher et al. (1992) *J. Virol.* 66(5) 2731–2739; Johann et al. (1992) *J. Virol.* 66 (5):1635–1640 (1992); Sommerfelt et al., (1990) *Virol.* 176:58–59; Wilson et al. (1989) *J. Virol.* 63:2374–2378; Miller et al., *J. Virol.* 65:2220–2224 (1991); Wong-Staal et al., PCT/US94/05700, and Rosenburg and Fauci (1993) in *Fundamental Immunology,* Third Edition Paul (ed) Raven Press, Ltd., New York and the references therein, and Yu et al. (1994) *Gene Therapy,* supra; U.S. Pat. No. 6,008,535, and the like). Other suitable viral vectors include, but are not limited to herpes virus, lentivirus, and vaccinia virus.

C. Host Cells

The present invention also provides a host cell containing a vector of this invention. A wide variety of host cells are available for propagation and/or expression of vectors. Examples include prokaryotic cells (such as *E. coli* and strains of *Bacillus, Pseudomonas,* and other bacteria), yeast or other fungal cells (including *S. cerevesiae* and *P. pastoris*), insect cells, plant cells, and phage, as well as higher eukaryotic cells (such as human embryonic kidney cells and other mammalian cells). Host cells according to the invention include cells in culture and cells present in live organisms, such as transgenic plants or animals or cells into which a gene therapy vector has been introduced.

A vector of the present invention is introduced into a host cell by any convenient method, which will vary depending on the vector-host system employed. Generally, a vector is introduced into a host cell by transformation (also known as "transfection") or infection with a virus (e.g., phage) bearing the vector. If the host cell is a prokaryotic cell (or other cell having a cell wall), convenient transformation methods include the calcium treatment method described by Cohen, et al. (1972) Proc. Natl. Acad. Sci., USA, 69:2110–14. If a prokaryotic cell is used as the host and the vector is a phagemid vector, the vector can be introduced into the host cell by infection. Yeast cells can be transformed using polyethylene glycol, for example, as taught by Hinnen (1978) Proc. Natl. Acad. Sci, USA, 75:1929–33. Mammalian cells are conveniently transformed using the calcium phosphate precipitation method described by Graham, et al. (1978) Virology, 52:546 and by Gorman, et al. (1990) DNA and Prot. Eng. Tech., 2:3–10. However, other known methods for introducing DNA into host cells, such as nuclear injection, electroporation, and protoplast fusion also are acceptable for use in the invention.

D. Expression and Purification of Chemokine Polypeptides

Host cells transformed with expression vectors can be used to express the chemokine polypeptides encoded by the nucleic acid molecules of the invention. Expression entails culturing the host cells under conditions suitable for cell growth and expression and recovering the expressed polypeptides from a cell lysate or, if the polypeptides are secreted, from the culture medium. In particular, the culture medium contains appropriate nutrients and growth factors for the host cell employed. The nutrients and growth factors are, in many cases, well known or can be readily determined empirically by those skilled in the art. Suitable culture conditions for mammalian host cells, for instance, are described in Mammalian Cell Culture (Mather ed., Plenum Press 1984) and in Barnes and Sato (1980) Cell 22:649.

In addition, the culture conditions should allow transcription, translation, and protein transport between cellular compartments. Factors that affect these processes are well-known and include, for example, DNA/RNA copy number; factors that stabilize DNA; nutrients, supplements, and transcriptional inducers or repressors present in the culture medium; temperature, pH and osmolality of the culture; and cell density. The adjustment of these factors to promote expression in a particular vector-host cell system is within the level of skill in the art. Principles and practical techniques for maximizing the productivity of in vitro mammalian cell cultures, for example, can be found in Mammalian Cell Biotechnology: a Practical Approach (Butler ed., IRL Press (1991).

Any of a number of well-known techniques for large- or small-scale production of proteins can be employed in expressing the polypeptides of the invention. These include, but are not limited to, the use of a shaken flask, a fluidized bed bioreactor, a roller bottle culture system, and a stirred tank bioreactor system. Cell culture can be carried out in a batch, fed-batch, or continuous mode.

Methods for recovery of recombinant proteins produced as described above are well-known and vary depending on the expression system employed. A polypeptide including a signal sequence can be recovered from the culture medium or the periplasm. Polypeptides can also be expressed intracellularly and recovered from cell lysates.

The expressed polypeptides can be purified from culture medium or a cell lysate by any method capable of separating the polypeptide from one or more components of the host cell or culture medium. Typically, the polypeptide is separated from host cell and/or culture medium components that would interfere with the intended use of the polypeptide. As a first step, the culture medium or cell lysate is usually centrifuged or filtered to remove cellular debris. The supernatant is then typically concentrated or diluted to a desired volume or diafiltered into a suitable buffer to condition the preparation for further purification.

The polypeptide can then be further purified using well-known techniques. The technique chosen will vary depending on the properties of the expressed polypeptide. If, for example, the polypeptide is expressed as a fusion protein containing an affinity domain, purification typically includes the use of an affinity column containing the cognate binding partner. For instance, polypeptides fused with hexahistidine or similar metal affinity tags can be purified by fractionation on an immobilized metal affinity column.

IV. Compositions

For research and therapeutic applications, the chemokine polypeptides of the invention or nucleic acid molecules encoding them are preferably formulated for administration to cells, tissues, or organisms.

1. Chemokine Polypeptides

The invention provides compositions, including pharmaceutical compositions, containing a chemokine polypeptide of the invention. The compositions optionally include other components, as for example, a storage solution, such as a suitable buffer, e.g., a physiological buffer. In a preferred embodiment, the composition is a pharmaceutical composition and the other component is a pharmaceutically acceptable carrier, such as are described in Remington's Pharmaceutical Sciences (1980) 16th editions, Osol, ed., 1980.

A pharmaceutically acceptable carrier suitable for use in the invention is non-toxic to recipients at the dosages employed, and can include a buffer (such as a phosphate buffer, citrate buffer, and buffers made from other organic acids), an antioxidant (e.g., ascorbic acid), low-molecular weight (less than about 10 residues) polypeptide, a protein (such as serum albumin, gelatin, and an immunoglobulin), a hydrophilic polymer (such as polyvinylpyrrolidone), an amino acid (such as glycine, glutamine, asparagine, arginine, and lysine), a monosaccharide, a disaccharide, and other carbohydrates (including glucose, mannose, and dextrins), a chelating agent (e.g., ethylenediaminetetratacetic acid [EDTA]), a sugar alcohol (such as mannitol and sorbitol), a salt-forming counterion (e.g., sodium), and/or an anionic surfactant (such as Tween™, Pluronics™, and PEG). In one embodiment, the pharmaceutically acceptable carrier is an aqueous pH-buffered solution.

Preferred embodiments include sustained-release pharmaceutical compositions. An exemplary sustained-release composition has a semipermeable matrix of a solid hydrophobic polymer to which the chemokine polypeptide is attached or in which the chemokine polypeptide is encapsulated. Examples of suitable polymers include a polyester, a hydrogel, a polylactide, a copolymer of L-glutamic acid and T-ethyl-L-glutamase, non-degradable ethylene-vinylacetate, a degradable lactic acid-glycolic acid copolymer, and poly-D-(-)-3-hydroxybutyric acid. Such matrices are in the form of shaped articles, such as films, or microcapsules.

Exemplary sustained release compositions include chemokine polypeptides attached, typically via ε-amino groups, to a polyalkylene glycol (e.g., polyethylene glycol [PEG]). Attachment of PEG to proteins is a well-known means of reducing immunogenicity and extending in vivo half-life (see, e.g., Abuchowski, J., et al. (1977) J. Biol. Chem. 252:3582–86. Any conventional "pegylation" method can be employed, provided the "pegylated" variant is capable of inducing differentiation of fibroblasts to myofibroblasts.

In another embodiment, a sustained-release composition includes a liposomally entrapped chemokine polypeptide. Liposomes are small vesicles composed of various types of lipids, phospholipids, and/or surfactants. These components are typically arranged in a bilayer formation, similar to the lipid arrangement of biological membranes. Liposomes containing chemokine polypeptides are prepared by known methods, such as, for example, those described in Epstein, et al. (1985) PNAS USA 82:3688–92, and Hwang, et al., (1980) PNAS USA, 77:4030–34. Ordinarily the liposomes in such preparations are of the small (about 200–800 Angstroms) unilamellar type in which the lipid content is greater than about 30 mol. percent cholesterol, the specific percentage being adjusted to provide the optimal therapy. Useful liposomes can be generated by the reverse-phase evaporation method, using a lipid composition including, for example, phosphatidylcholine, cholesterol, and PEG-derivatized phosphatidylethanolamine (PEG-PE). If desired, liposomes are extruded through filters of defined pore size to yield liposomes of a particular diameter.

Pharmaceutical compositions can also include a chemokine polypeptide adsorbed onto a membrane, such as a silastic membrane, which can be implanted, as described in International Publication No. WO 91/04014.

Because the chemokine polypeptides of the invention can accelerate wound healing, the invention provides a poultice or bandage bearing a chemokine polypeptide on a surface designed to be applied to a wound.

Pharmaceutical compositions of the invention can be stored in any standard form, including, e.g., an aqueous solution or a lyophilized cake. Such compositions are typically sterile when administered to recipients. Sterilization of an aqueous solution is readily accomplished by filtration through a sterile filtration membrane. If the composition is stored in lyophilized form, the composition can be filtered before or after lyophilization and reconstitution.

2. Nucleic Acid Molecules Encoding Chemokine Polypeptides

The invention provides compositions, including pharmaceutical compositions, containing a nucleic acid molecule encoding the chemokine polypeptide of the invention. In one embodiment, the invention provides a pharmaceutical composition containing a nucleic acid molecule encoding a differentiation-inducing CXC chemokine, or a fragment thereof, wherein the administration of this composition to cells including fibroblasts results in the expression of the differentiation-inducing CXC chemokine, or fragment thereof, in an amount sufficient to induce differentiation of fibroblasts to myofibroblasts.

Compositions including nucleic acid molecules described herein optionally include other components, as for example, a storage solution, such as a suitable buffer, e.g., a physiological buffer. In a preferred embodiment, the composition is a pharmaceutical composition and the other component is a pharmaceutically acceptable carrier as described above.

In preferred embodiments, compositions containing nucleic acids of the invention also include a component that facilitates entry of the nucleic acid molecule into a cell. Components that facilitate intracellular delivery of nucleic acid molecules are well-known and include, for example, lipids, liposomes, water-oil emulsions, polyethylene imines and dendrimers, any of which can be used in compositions according to the invention. Lipids are among the most widely used components of this type, and any of the available lipids or lipid formulations can be employed with the nucleic acid molecules of the invention. Typically, cationic lipids are preferred. Preferred cationic lipids include N-[1-(2,3-dioleyloxy)propyl]-n,n,n-trimethylammonium chloride (DOTMA), dioleoyl phosphotidylethanolamine (DOPE), and/or dioleoyl phosphatidylcholine (DOPC). Nucleic acid molecules can also be entrapped in liposomes, as described above for polypeptides.

In another embodiment, nucleic acid molecules are complexed to dendrimers, which can be used to transfect cells. Dendrimer polycations are three dimensional, highly ordered oligomeric and/or polymeric compounds typically formed on a core molecule or designated initiator by reiterative reaction sequences adding the oligomers and/or polymers and providing an outer surface that is positively changed. Suitable dendrimers include, but are not limited to, "starburst" dendrimes and various dendrimer polycations.

Dendrimer polycations are preferably non-covalently associated with the nucleic acid molecules of the invention. This permits an easy disassociation or disassembling of the composition once it is delivered into the cell. Typical dendrimer polycations suitable for use herein have a molecular weight ranging from about 2,000 to 1,000,000 Da, and more preferably about 5,000 to 500,000 Da. However, other molecular weights can also be employed. Preferred dendrimer polycations have a hydrodynamic radius of about 11 to 60 Å., and more preferably about 15 to 55 Å. Other sizes, however, are also suitable for use in the invention. Methods for the preparation and use of dendrimers to introduce nucleic acid molecules into cells in vivo are well known to those of skill in the art and described in detail, for example, in PCT/US83/02052 and U.S. Pat. Nos. 4,507,466; 4,558,120; 4,568,737; 4,587,329; 4,631,337; 4,694,064; 4,713,975; 4,737,550; 4,871,779; 4,857,599; and 5,661,025.

For therapeutic use, nucleic acid molecules of the invention are formulated in a manner appropriate for the particular indication. U.S. Pat. No. 6,001,651 to Bennett et al. describes a number of pharmaceutical compositions and formulations suitable for use with an oligonucleotide therapeutic as well as methods of administering such oligonucleotides. In a preferred embodiment, therapeutic compositions of the invention include nucleic acid molecules combined with lipids, as described above.

Compositions containing nucleic acid molecules can be stored in any standard form, including, e.g., an aqueous solution or a lyophilized cake. Such compositions are typically sterile when administered to cells or recipients. Sterilization of an aqueous solution is readily accomplished by filtration through a sterile filtration membrane. If the composition is stored in lyophilized form, the composition can be filtered before or after lyophilization and reconstitution.

V. Methods of Inducing or Inhibiting Differentiation of Fibroblasts to Myofibroblasts The invention also provides methods of inducing or inhibiting differentiation of fibroblasts to myofibroblasts that make use of the polypeptides, nucleic acid molecules, and or compositions described here.

A. Method of Inducing Differentiation

1. In General

The method of inducing differentiation of fibroblasts to myofibroblasts entails contacting fibroblasts with an effective amount of a chemokine polypeptide of the invention to induce differentiation. Fibroblasts useful in this regard are those that are generally capable of responding to chemokines, such as for example embryonic fibroblasts or wound fibroblasts.

The fibroblasts are contacted with the chemokine polypeptide under conditions suitable for differentiation, typically physiological conditions. The duration of contact can vary, depending on the particular application of the method, but is, at least, sufficient to induce differentiation (as defined above) of fibroblasts to myofibroblasts. The duration of contact can range from minutes to days or longer. For research applications, chemokine polypeptides are typically contacted with fibroblasts for, e.g., about 30 mins.; or about 1, about 3, about 6, or about 12 hours; or about 1, about 2, about 5, about 10, or about 15 days.

Contact of chemokine polypeptides with fibroblasts can be achieved directly, i.e., by administering a composition containing the polypeptide to the cells, or indirectly, i.e., by administering a composition containing a nucleic acid molecule encoding the polypeptide to the cells. In the latter embodiment, this administration results in the introduction of the nucleic acid molecule into one or more cells and the subsequent expression of the polypeptide in an amount sufficient to induce differentiation of fibroblasts to myofibroblasts. In one embodiment, a composition containing a nucleic acid molecule encoding a differentiation-inducing CXC chemokine, or a fragment thereof, is administered to cells including fibroblasts to induce differentiation of fibroblasts to myofibroblasts.

This method can be carried out in vitro, i.e., in cells or tissues that are not part of an organism or in vivo, in cells that are part of an organism. In one embodiment, fibroblasts are contacted in vitro in with an effective amount of a differentiation-inducing CXC chemokine, or fragment thereof, which induces the differentiation of fibroblasts to myofibroblasts. Fibroblasts that are contacted with a chemokine polypeptide in vitro can be maintained in vitro (e.g., for research applications) or administered to a subject having, or at risk for, a condition that can be ameliorated by the differentiation of fibroblasts to myofibroblasts. In the latter embodiment, the fibroblasts are preferably obtained from the subject to which they are administered after chemokine treatment.

Alternatively, fibroblasts can be contacted in vivo with a chemokine polypeptide by administering a composition containing the chemokine polypeptide (or a nucleic acid molecule encoding the chemokine polypeptide) directly to a subject having, or at risk for, a condition that can be ameliorated by the differentiation of fibroblasts to myofibroblasts. Conditions that are particularly amenable to treatment using this method include those that are characterized by a deficiency of myofibroblasts, as in the case of corneal surgery. In a preferred embodiment, the condition is wound and the differentiation of fibroblasts to myofibroblasts promotes wound healing. As described in the Example below, this differentiation is accompanied by more rapid healing, an in particular, more rapid wound contraction and closure.

2. Administration

For in vitro applications, fibroblasts are contacted with a chemokine polypeptide of the invention simply by adding the chemokine polypeptide or the related nucleic acid molecule or composition directly to the medium of cultured cells (as described for cCAF in the Example) or directly to tissues.

Methods for in vivo administration do not differ from known methods for administering therapeutic polypeptides, peptides, or nucleic acid molecules encoding them. Suitable routes of administration include, for example, topical, intravenous, intraperitoneal, intracerebral, intramuscular, intraocular, intraarterial, or intralesional routes. Pharmaceutical compositions of the invention can be administered continuously by infusion, by bolus injection, or, where the compositions are sustained-release preparations, by methods appropriate for the particular preparation. For promoting wound healing, topical preparations are preferred and suitable formulations include lotions, ointments, gels, and the like, as well as preparations in which the chemokine polypeptide is contained on a surface of a poultice or bandage that is designed to contact and cover a wound.

3. Dose

The dose of chemokine polypeptide is sufficient to induce differentiation of fibroblasts to myofibroblasts without significant toxicity. For in vitro use, these criteria are met by administering the chemokine polypeptide at a concentration of between about 10 nM and about 10 $\mu$M. Preferred concentrations are in the range of about 100 nM to about 1 µM, more preferably about 200 nM to about 800 nM, and most preferably about 300 nM to about 600 nM.

For in vivo applications, the dose of chemokine polypeptide depends, for example, upon the therapeutic objectives, the route of administration, and the condition of the subjected. Accordingly, it is necessary for the clinician to titer the dosage and modify the route of administration as required to obtain the optimal therapeutic effect. Generally, the clinician begins with a low dose and increases the dosage until the desired therapeutic effect is achieved. Starting doses for a given chemokine polypeptide can be extrapolated from in vitro data, such as that described in the Example. Starting doses for topical administration can be extrapolated from the in vivo wounding data presented in the Example.

B. Method of Inhibiting Differentiation

The method of inhibiting differentiation of fibroblasts to myofibroblasts entails contacting fibroblasts with an effective amount of an inhibitor of a differentiation-inducing chemokine to inhibit differentiation. In preferred embodiments, such inhibitors disrupt the normal function of the differentiation-inducing domain, for example, by binding to the domain; binding near the domain and sterically hindering access to the domain; binding the chemokine and inducing a conformational change in the domain; and binding to the relevant chemokine receptor without activating the receptor. Preferred inhibitors include antibodies, such as that described in the Example.

Either polyclonal or monoclonal antibodies can be used in the methods of the invention. Polyclonal antibodies are preferably raised by multiple injections (e.g. subcutaneous or intramuscular injections) of substantially pure polypeptides or antigenic polypeptides into a suitable non-human mammal. The antigenicity of the target peptides can be determined by conventional techniques to determine the magnitude of the antibody response of an animal that has been immunized with the peptide. Generally, the peptides that are used to raise antibodies for use in the methods of this invention should generally be those which induce production of high titers of antibody with relatively high affinity for differentiation-inducing chemokines of the invention, and, in particular, for the differentiation domain of such chemokines.

If desired, the immunizing peptide may be coupled to a carrier protein by conjugation using techniques that are well known in the art. Such commonly used carriers that are chemically coupled to the peptide include keyhole limpet hemocyanin (KLH), thyroglobulin, bovine serum albumin (BSA), and tetanus toxoid. The coupled peptide is then used to immunize the animal (e.g. a mouse or a rabbit).

The antibodies are then obtained from blood samples taken from the mammal. The techniques used to develop polyclonal antibodies are extensively described in the literature (see, e.g., Methods of Enzymology, "Production of Antisera With Small Doses of Immunogen: Multiple Intradermal Injections", Langone, et al. eds. (Acad. Press, 1981)). Polyclonal antibodies produced by the animals can be further purified, for example, by binding to and elution from a matrix to which the peptide to which the antibodies were raised is bound. Those of skill in the art will know of various techniques common in the immunology arts for purification and/or concentration of polyclonal, as well as monoclonal, antibodies see, for example, Coligan, et al. (1991) Unit 9, Current Protocols in Immunology, Wiley Interscience).

Preferably, however, the antibodies produced will be monoclonal antibodies ("mAb's"). For preparation of monoclonal antibodies, immunization of a mouse or rat is preferred. The general method used for production of hybridomas secreting mAbs is well known (Kohler and Milstein (1975) Nature, 256:495). Briefly, as described by Kohler and Milstein, the technique entailed isolating lymphocytes from regional draining lymph nodes of five separate cancer patients with either melanoma, teratocarcinoma or cancer of the cervix, glioma or lung, (where samples were obtained from surgical specimens), pooling the cells, and fusing the cells with SHFP-1. Hybridomas were screened for production of antibody which bound to cancer cell lines. Confirmation of specificity among mAb's can be accomplished using relatively routine screening techniques (such as the enzyme-linked immunosorbent assay, or "ELISA") to determine the elementary reaction pattern of the mAb of interest.

It is also possible to evaluate a mAb to determine whether it has the same specificity as a mAb described herein without undue experimentation by determining whether the mAb being tested prevents the described mAb from binding a target chemokine polypeptide. If the mAb being tested competes with the mAb described herein, it is likely that the two monoclonal antibodies bind to the same or a closely related epitope. Still another way to determine whether a mAb has the specificity of a mAb of the invention is to preincubate the mAb described herein with an antigen with which it is normally reactive, and determine if the mAb being tested is inhibited in its ability to bind the antigen. Such inhibition indicates that the mAb being tested has the same, or a closely related, epitopic specificity as the mAb described herein.

Antibodies fragments, e.g. single chain antibodies (scFv or others), can also be produced/selected using phage display technology. The ability to express antibody fragments on the surface of viruses that infect bacteria (bacteriophage or phage) makes it possible to isolate a single binding antibody fragment, e.g., from a library of greater than $10^{10}$ nonbinding clones. To express antibody fragments on the surface of phage (phage display), an antibody fragment gene is inserted into the gene encoding a phage surface protein (e.g., pIII) and the antibody fragment-pIII fusion protein is displayed on the phage surface (McCafferty et al. (1990) Nature, 348: 552–554; Hoogenboom et al. (1991) Nucleic Acids Res. 19: 4133–4137).

Since the antibody fragments on the surface of the phage are functional, phage bearing antigen binding antibody fragments can be separated from non-binding phage by antigen affinity chromatography (McCafferty et al. (1990) Nature, 348: 552–554). Depending on the affinity of the antibody fragment, enrichment factors of 20 fold–1,000,000 fold are obtained for a single round of affinity selection. By infecting bacteria with the eluted phage, however, more phage can be grown and subjected to another round of selection. In this way, an enrichment of 1000 fold in one round can become 1,000,000 fold in two rounds of selection (McCafferty et al. (1990) Nature, 348: 552–554). Thus even when enrichments are low (Marks et al. (1991) J. Mol. Biol. 222: 581–597), multiple rounds of affinity selection can lead to the isolation of rare phage. Since selection of the phage antibody library on antigen results in enrichment, the majority of clones bind antigen after as few as three to four rounds of selection. Thus only a relatively small number of clones (several hundred) need to be analyzed for binding to antigen.

Human antibodies can be produced without prior immunization by displaying very large and diverse V-gene repertoires on phage (Marks et al. (1991) J. Mol. Biol. 222: 581–597). In one embodiment natural $V_H$ and $V_L$ repertoires present in human peripheral blood lymphocytes are isolated from unimmunized donors by PCR. The V-gene repertoires were spliced together at random using PCR to create a scFv gene repertoire which is was cloned into a phage vector to create a library of 30 million phage antibodies (Id.). From this single "naive" phage antibody library, binding antibody fragments have been isolated against more than 17 different antigens, including haptens, polysaccharides and proteins (Marks et al. (1991) *J. Mol. Biol.* 222: 581–597; Marks et al. (1993). *Bio/Technology.* 10: 779–783; Griffiths et al. (1993) *EMBO J.* 12: 725–734; Clackson et al. (1991) *Nature.* 352: 624–628). Antibodies have been produced against self proteins, including human thyroglobulin, immunoglobulin, tumor necrosis factor and CEA (Griffiths et al. (1993) *EMBO J.* 12: 725–734). It is also possible to isolate antibodies against cell surface antigens by selecting directly on intact cells. The antibody fragments are highly specific for the antigen used for selection and have affinities in the 1 nM to 100 nM range (Marks et al. (1991) *J. Mol. Biol.* 222: 581–597; Griffiths et al. (1993) *EMBO J.* 12: 725–734). Larger phage antibody libraries result in the isolation of more antibodies of higher binding affinity to a greater proportion of antigens.

It will also be recognized that antibodies can be prepared by any of a number of commercial services (e.g., Berkeley antibody laboratories, Bethyl Laboratories, Anawa, Eurogenetec, etc.).

In addition to antibody inhibitors, the identification of the chemokine domain responsible for induction of differentiation makes it possible to design other types of inhibitors, including peptide and small molecule inhibitors, using standard methodologies. In a preferred embodiment, the inhibitor is an inhibitor of a differentiation-inducing CXC chemokine.

The inhibitor is added to the fibroblasts during or preferably before contact of the fibroblasts with a differentiation-inducing chemokine or fragment thereof, i.e., before appreciable differentiation has occurred. This step is carried out under conditions that would otherwise be suitable for differentiation, typically physiological conditions. The duration of contact with the inhibitor can vary, depending on the particular application of the method, but typically lasts as long as the chemokine or chemokine fragment is present.

This method can be carried out in vitro, i.e., in cells or tissues, or in vivo. In either case, the method can be employed to investigate the role of chemokine-induced differentiation of fibroblasts to myofibroblasts in physiological processes such as wound healing and in various fibrotic and other diseases.

In vivo applications include the treatment of subjects having, or at risk for, a condition that can be ameliorated by inhibiting the differentiation of fibroblasts to myofibroblasts. Conditions that are particularly amenable to treatment by inhibition of myofibroblast differentiation include those that are characterized by excess myofibroblasts. Examples of pathological conditions in which myofibroblasts are known to play a role including keloid formation, pulmonary fibrosis, scleroderma, and cancers.

Methods for administering chemokine inhibitors useful in the method will vary, depending on the particular inhibitor, as will dose. In vitro treatment with antibody inhibitors can be carried out as described in the examples. Antibody inhibitors can be administered in vivo, as has been demonstrated, for example, with herceptin. The determination of suitable routes of administration and doses is within the level of skill in the art.

VI. Screening Methods

A. Screening for Increase in the Level of Differentiation-Inducing Chemokine Nucleic Acid or Protein 1. In General As indicated above, in one aspect, this invention is premised on the discovery that chemokines induce the differentiation of fibroblasts to myofibroblasts. Thus, in one embodiment, this invention provides a method of screening for an agent that induces or inhibits this differentiation. The method involves contacting a cell containing differentiation-inducing chemokine gene, preferably a CXC chemokine, with a test agent and then detecting the level of differentiation-inducing chemokine mRNA or protein. A dose-dependent increase in the level of the chemokine mRNA or protein indicates that the test agent induces differentiation of fibroblasts to myofibroblasts. Conversely, a dose-dependent decrease in the level of the chemokine mRNA or protein indicates that the test agent inhibits differentiation of fibroblasts to myofibroblasts. In preferred embodiments, the method entails assaying the levels of mRNA or protein for IL-8-, cCAF-, and MGSA. The level of chemokine mRNA or protein can be measured by a variety of different techniques, examples of which are described below.

2. Sample Collection and Processing

The screening method of the invention is generally (although not necessarily) carried out in vitro. Accordingly, the chemokine nucleic acid and/or protein is preferably quantified in a cell line or a biological sample derived from a mammal (e.g., whole blood, plasma, serum, synovial fluid, cerebrospinal fluid, bronchial lavage, ascites fluid, bone marrow aspirate, pleural effusion, urine, or tumor tissue), and more preferably from a human. For ease of description, cell lines and biological samples are referred to as "samples" below.

The sample may be pretreated as necessary by dilution in an appropriate buffer solution or concentrated, if desired. Any of a number of standard aqueous buffer solutions, employing one of a variety of buffers, such as phosphate, Tris, or the like, at physiological pH can be used.

3. Nucleic-Acid Based Assays a. Nucleic Acid Sample

Changes in chemokine expression level can be detected by measuring changes in mRNA and/or a nucleic acid derived from the mRNA (e.g. reverse-transcribed cDNA, etc.). The nucleic acid is, in certain preferred embodiments, isolated from the sample according to any of a number of methods well known to those of skill in the art. Methods of isolating total mRNA are well known to those of skill in the art. For example, methods of isolation and purification of nucleic acids are described in detail in by Tijssen ed., (1993) Chapter 3 of *Laboratory Techniques in Biochemistry and Molecular Biology: Hybridization With Nucleic Acid Probes, Part I. Theory and Nucleic Acid Preparation,* Elsevier, N.Y. and Tijssen ed.

In a preferred embodiment, the "total" nucleic acid is isolated from a given sample using, for example, an acid guanidinium-phenol-chloroform extraction method and polyA+mRNA is isolated by oligo dT column chromatography or by using (dT)n magnetic beads (see, e.g., Sambrook et al., *Molecular Cloning: A Laboratory Manual* (2nd ed.), Vols. 1–3, Cold Spring Harbor Laboratory, (1989), or *Current Protocols in Molecular Biology*, F. Ausubel et al., ed. Greene Publishing and Wiley-Interscience, New York (1987)).

Frequently, it is desirable to amplify the nucleic acid sample prior to assaying for chemokine expression level.

One of skill in the art will appreciate that whatever amplification method is used, if a quantitative result is desired, care must be taken to use a method that maintains or controls for the relative frequencies of the amplified nucleic acids.

Methods of "quantitative" amplification are well known to those of skill in the art. For example, quantitative PCR involves simultaneously co-amplifying a known quantity of a control sequence using the same primers. This provides an internal standard that may be used to calibrate the PCR reaction.

One preferred internal standard is a synthetic AW106 cRNA. The AW106 cRNA is combined with RNA isolated from the sample according to standard techniques known to those of skill in the art. The RNA is then reverse transcribed using a reverse transcriptase to provide complementary DNA. The cDNA sequences are then amplified (e.g., by PCR) using radioactively labeled primers. The amplification products are separated, typically by electrophoresis, and the amount of radioactivity (proportional to the amount of amplified product) is determined. The amount of mRNA in the sample is then calculated by comparison with the signal produced by the known AW106 RNA standard. Detailed protocols for quantitative PCR are provided in PCR Protocols, A Guide to Methods and Applications, Innis et al., Academic Press, Inc. N.Y., (1990).

In a particularly preferred embodiment, where it is desired to quantify the transcription level (and thereby expression) of a one or more genes in a sample, the nucleic acid sample is one in which the concentration of the mRNA transcript(s) of the gene or genes, or the concentration of the nucleic acids derived from the mRNA transcript(s), is proportional to the transcription level (and therefore expression level) of that gene. Similarly, it is preferred that the hybridization signal intensity be proportional to the amount of hybridized nucleic acid. While it is preferred that the proportionality be relatively strict (e.g., a doubling in transcription rate results in a doubling in mRNA transcript in the sample nucleic acid pool and a doubling in hybridization signal), one of skill will appreciate that the proportionality can be more relaxed and even non-linear. Thus, for example, an assay where a 5-fold difference in concentration of the target mRNA results in a 3- to 6-fold difference in hybridization intensity is sufficient for most purposes. Where more precise quantification is required appropriate controls can be run to correct for variations introduced in sample preparation and hybridization as described herein. In addition, serial dilutions of "standard" target nucleic acids (e.g., mRNAs) can be used to prepare calibration curves according to methods well known to those of skill in the art. Of course, where simple detection of the presence or absence of a transcript or large differences of changes in nucleic acid concentration is desired, no elaborate control or calibration is required.

In the simplest embodiment, such a nucleic acid sample is the total mRNA or a total cDNA isolated and/or otherwise derived from a biological sample.

b. Hybridization-Based Assays (i) Detection of Gene Transcripts

Methods of detecting and/or quantifying the transcript(s) of one or more chemokine gene(s) (e.g. mRNA or cDNA made therefrom) using nucleic acid hybridization techniques are known to those of skill in the art (see Sambrook et al. supra). For example, the presence, absence, or quantity of a reverse-transcribed cDNA can be measured by Southern blot. Alternatively, in a Northern blot, mRNA is directly quantitated. In both cases, labeled probes are used to identify and/or quantify the target mRNA.

The probes used herein for detection of the chemokine nucleic acids can be full-length or less than the full-length of these nucleic acids. Shorter probes are empirically tested for specificity. Preferably nucleic acid probes are 20 bases or longer in length. (see Sambrook et al. for methods of selecting nucleic acid probe sequences for use in nucleic acid hybridization.) Visualization of the hybridized probes allows the qualitative determination of the presence or absence of the chemokine nucleic acid, and standard methods (such as, e.g., densitometry) can be used to quantify the level of the chemokine nucleic acid.

c. Amplification-Based Assays

In still another embodiment, amplification-based assays can be used to measure chemokine expression level. In such amplification-based assays, the target nucleic acid sequences act as template(s) in amplification reaction(s) (e.g. Polymerase Chain Reaction (PCR) or reverse-transcription PCR (RT-PCR)). As discussed above, in a quantitative amplification, the amount of amplification product is proportional to the amount of template in the original sample. Detailed protocols for quantitative PCR are provided in Innis et al. (1990) PCR Protocols, A Guide to Methods and Applications, Academic Press, Inc. N.Y.).

Other suitable amplification methods include, but are not limited to ligase chain reaction (LCR) (see Wu and Wallace (1989) Genomics 4: 560, Landegren et al. (1988) Science 241: 1077, and Barringer et al. (1990) Gene 89: 117, transcription amplification (Kwoh et al. (1989) Proc. Natl. Acad. Sci. USA 86: 1173), self-sustained sequence replication (Guatelli et al. (1990) Proc. Nat. Acad. Sci. USA 87: 1874), dot PCR, and linker adapter PCR, etc.

d. Hybridization Formats and Optimization of Hybridization Conditions (i) Array-Based Hybridization Formats In one embodiment, the methods of this invention can be utilized in array-based hybridization formats. In an array format a large number of different hybridization reactions can be run essentially "in parallel." This provides rapid, essentially simultaneous, evaluation of a number of hybridizations in a single experiment. Methods of performing hybridization reactions in array based formats are well known to those of skill in the art (see, e.g., Pastinen (1997) Genome Res. 7: 606–614; Jackson (1996) Nature Biotechnology 14:1685; Chee (1995) Science 274: 610; WO 96/17958, Pinkel et al. (1998) Nature Genetics 20: 207–211).

Arrays, particularly nucleic acid arrays can be produced according to a wide variety of methods well known to those of skill in the art. For example, in a simple embodiment, "low density" arrays can simply be produced by spotting (e.g. by hand using a pipette) different nucleic acids at different locations on a solid support (e.g. a glass surface, a membrane, etc.).

This simple spotting, approach has been automated to produce high density spotted microarrays. For example, U.S. Pat. No: 5,807,522 describes the use of an automated system that taps a microcapillary against a surface to deposit a small volume of a biological sample. The process is repeated to generate high density arrays.

Arrays can also be produced using oligonucleotide synthesis technology. Thus, for example, U.S. Pat. No. 5,143, 854 and PCT Patent Publication Nos. WO 90/15070 and 92/10092 teach the use of light-directed combinatorial synthesis of high density oligonucleotide microarrays. Synthesis of high density arrays is also described in U.S. Pat. Nos. 5,744,305; 5,800,992; and 5,445,934.

In a preferred embodiment, the arrays used in this invention comprise "probe" nucleic acids. These probes are then hybridized respectively with their "target" nucleic acids (e.g., mRNA derived from a biological sample). The arrays can be hybridized with a single population of sample nucleic acid or can be used with two differentially labeled collections (as with a test sample and a reference sample). Alternatively, the format can be reversed, such that nucleic acids from different samples (i.e., the target nucleic acds) are arrayed and this array is then probed with one or more probes, which can be differentially labeled.

Many methods for immobilizing nucleic acids on a variety of solid surfaces are known in the art. A wide variety of organic and inorganic polymers, as well as other materials, both natural and synthetic, can be employed as the material for the solid surface. Illustrative solid surfaces include, e.g., nitrocellulose, nylon, glass, quartz, diazotized membranes (paper or nylon), silicones, polyformaldehyde, cellulose, and cellulose acetate. In addition, plastics such as polyethylene, polypropylene, polystyrene, and the like can be used. Other materials which may be employed include paper, ceramics, metals, metalloids, semiconductive materials, cermets or the like. In addition, substances that form gels can be used. Such materials include, e.g., proteins (e.g., gelatins), lipopolysaccharides, silicates, agarose and polyacrylamides. Where the solid surface is porous, various pore sizes may be employed depending upon the nature of the system.

In preparing the surface, a plurality of different materials may be employed, particularly as laminates, to obtain various properties. For example, proteins (e.g., bovine serum albumin) or mixtures of macromolecules (e.g., Denhardt's solution) can be employed to avoid non-specific binding, simplify covalent conjugation, enhance signal detection or the like. If covalent bonding between a compound and the surface is desired, the surface will usually be polyfunctional or be capable of being polyfunctionalized. Functional groups which may be present on the surface and used for linking can include carboxylic acids, aldehydes, amino groups, cyano groups, ethylenic groups, hydroxyl groups, mercapto groups and the like. The manner of linking a wide variety of compounds to various surfaces is well known and is amply illustrated in the literature.

For example, methods for immobilizing nucleic acids by introduction of various functional groups to the molecules is known (see, e.g., Bischoff (1987) *Anal. Biochem.,* 164: 336–344; Kremsky (1987) *Nucl. Acids Res.* 15: 2891–2910). Modified nucleotides can be incorporated into nucleic acids using PCR primers containing the modified nucleotide, or by enzymatic end labeling with modified nucleotides. Use of glass or membrane supports (e.g., nitrocellulose, nylon, polypropylene) for the nucleic acid arrays of the invention is advantageous because of well-developed technology employing manual and robotic methods of arraying targets at relatively high element densities. Such membranes are generally available, and protocols and equipment for hybridization to membranes are well known.

Arrays on solid surface substrates with much lower fluorescence than membranes, such as glass, quartz, or small beads, can achieve much better sensitivity in assays employing fluorescently labeled probes. Substrates such as glass or fused silica are advantageous in that they provide a very low fluorescence substrate, and a highly efficient hybridization environment. Nucleic acids can be conveniently coupled to glass using commercially available reagents. For instance, materials for preparation of silanized glass with a number of functional groups are commercially available or can be prepared using standard techniques (see, e.g., Gait (1984) *Oligonucleotide Synthesis: A Practical Approach*, IRL Press, Wash., D.C.). Quartz cover slips, which have at least 10-fold lower autofluorescence than glass, can also be silanized.

Alternatively, probes can also be immobilized on commercially available coated beads or other surfaces. For instance, biotin end-labeled nucleic acids can be bound to commercially available avidin-coated beads. Streptavidin or anti-digoxigenin antibody can also be attached to silanized glass slides by protein-mediated coupling using e.g., protein A following standard protocols (see, e.g., Smith (1992) *Science* 258: 1122–1126). Biotin or digoxigenin end-labeled nucleic acids can be prepared according to standard techniques. Alternatively, paramagnetic particles, such as ferric oxide particles, with or without avidin coating, can be used.

Arrays can be made up of target elements of various sizes, ranging from 1 mm diameter down to 1 µm can be used. Relatively simple approaches capable of quantitative fluorescent imaging of 1 cm$^2$ areas have been described that permit acquisition of data from a large number of target elements in a single image (see, e.g., Wittrup (1994) *Cytometry* 16:206–213, Pinkel et al. (1998) *Nature Genetics* 20: 207–211).

(ii) Other Hybridization Formats

A variety of nucleic acid hybridization formats are known to those skilled in the art. For example, common formats include sandwich assays and competition or displacement assays. Hybridization techniques are generally described in Hames and Higgins (1985) *Nucleic Acid Hybridization, A Practical Approach*, IRL Press; Gall and Pardue (1969) *Proc. Natl. Acad. Sci. USA* 63: 378–383; and John et al. (1969) *Nature* 223: 582–587.

Sandwich assays are commercially useful hybridization assays for detecting or isolating nucleic acid sequences. Such assays utilize a "capture" nucleic acid covalently immobilized to a solid support and a labeled "signal" nucleic acid in solution. The sample provides the target nucleic acid. The capture nucleic acid and signal nucleic acid each hybridize with the target nucleic acid to form a "sandwich" hybridization complex. To be most effective, the signal nucleic acid should not hybridize with the capture nucleic acid.

Typically, labeled signal nucleic acids are used to detect hybridization. Complementary nucleic acids or signal nucleic acids may be labeled by any one of several methods typically used to detect the presence of hybridized polynucleotides. The most common method of detection is the use of autoradiography with $^3$H, $^{125}$I, $^{35}$S, $^{14}$C, or $^{32}$P-labelled probes or the like. Other labels include ligands that bind to labeled antibodies, fluorophores, chemi-luminescent agents, enzymes, and antibodies which can serve as specific binding pair members for a labeled ligand.

Detection of a hybridization complex may require the binding of a signal-generating complex to a duplex of target and probe nucleic acids. Typically, such binding occurs through ligand and anti-ligand interactions as between a ligand-conjugated probe and an anti-ligand conjugated with a signal.

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBAO, Cangene, Mississauga, Ontario) and Q Beta Replicase systems.

(iii) Optimization of Hybridization Conditions

Nucleic acid hybridization simply involves providing a denatured probe and target nucleic acid under conditions where the probe and its complementary target can form stable hybrid duplexes through complementary base pairing. The nucleic acids that do not form hybrid duplexes are then washed away leaving the hybridized nucleic acids to be detected, typically through detection of an attached detectable label. It is generally recognized that nucleic acids are denatured by increasing the temperature or decreasing the salt concentration of the buffer containing the nucleic acids, or in the addition of chemical agents, or the raising of the pH. Under low stringency conditions (e.g., low temperature and/or high salt and/or high target concentration) hybrid duplexes (e.g., DNA:DNA, RNA:RNA, or RNA:DNA) will form even where the annealed sequences are not perfectly complementary. Thus specificity of hybridization is reduced at lower stringency. Conversely, at higher stringency (e.g., higher temperature or lower salt) successful hybridization requires fewer mismatches.

One of skill in the art will appreciate that hybridization conditions may be selected to provide any degree of stringency. In general, there is a tradeoff between hybridization specificity (stringency) and signal intensity. In a preferred embodiment, the wash is performed at the highest stringency that produces consistent results and that provides a signal intensity greater than approximately 10% of the background intensity. Hybridization can performed at low stringency to ensure hybridization and then subsequent washes are performed to eliminate mismatched hybrid duplexes. Successive washes may be performed at increasingly higher stringency (e.g., down to as low as 0.25×SSPE at 37° C. to 70° C.) until a desired level of hybridization specificity is obtained. Stringency can also be increased by addition of agents such as formamide. Hybridization specificity may be evaluated by comparison of hybridization to the test probes with hybridization to the various controls that can be included in the reaction mixture.

In a preferred embodiment, background signal is reduced by the use of a blocking reagent (e.g., tRNA, sperm DNA, cot-1 DNA, etc.) during the hybridization to reduce non-specific binding. The use of blocking agents in hybridization is well known to those of skill in the art (see, e.g., Chapter 8 in P. Tijssen, supra.)

Methods of optimizing hybridization conditions are well known to those of skill in the art (see, e.g., Tijssen (1993) *Laboratory Techniques in Biochemistry and Molecular Biology, Vol. 24: Hybridization With Nucleic Acid Probes*, Elsevier, N.Y.).

Optimal conditions are also a function of the sensitivity of label detection. In the case of fluorescence detection, for example, optimal conditions will vary with different combinations of substrate type, fluorochrome, excitation and emission bands, spot size and the like. As discussed above, low fluorescence background surfaces can be used (see, e.g., Chu (1992) *Electrophoresis* 13:105–114). The sensitivity for detection of spots ("target elements") of various diameters on the candidate surfaces can be readily determined by, e.g., spotting a dilution series of fluorescently end labeled DNA fragments. These spots are then imaged using conventional fluorescence microscopy. The sensitivity, linearity, and dynamic range achievable from the various combinations of fluorochrome and solid surfaces (e.g., glass, fused silica, etc.) can thus be determined. Serial dilutions of pairs of fluorochrome in known relative proportions can also be analyzed. This determines the accuracy with which fluorescence ratio measurements reflect actual fluorochrome ratios over the dynamic range permitted by the detectors and fluorescence of the substrate upon which the probe has been fixed.

(iv) Labeling and Detection of Nucleic Acids

In a preferred embodiment, the hybridized nucleic acids are detected by detecting one or more labels attached to the sample nucleic acids. Detectable labels suitable for use in the present invention include any composition detectable by spectroscopic, photochemical, biochemical, immunochemical, electrical, optical or chemical means. Useful labels in the present invention include biotin for staining with labeled streptavidin conjugate, magnetic beads (e.g., Dynabeads™), fluorescent dyes (e.g., fluorescein, texas red, rhodamine, green fluorescent protein, and the like, see, e.g., Molecular Probes, Eugene, Oregon, USA), radio-labels (e.g., $^{3}H$, $^{125}I$, $^{35}S$, $^{14}C$, or $^{32}P$), enzymes (e.g., horse radish peroxidase, alkaline phosphatase and others commonly used in an ELISA), and colorimetric labels such as colloidal gold (e.g., gold particles in the 40–80 nm diameter size range scatter green light with high efficiency) or colored glass or plastic (e.g., polystyrene, polypropylene, latex, etc.) beads. Patents teaching the use of such labels include U.S. Pat. Nos. 3,817,837; 3,850,752; 3,939,350; 3,996,345; 4,277,437; 4,275,149; and 4,366,241.

The label may be added to the target (sample) nucleic acid(s) prior to, or after the hybridization. So called "direct labels" are detectable labels that are directly attached to or incorporated into the target (sample) nucleic acid prior to hybridization. In contrast, so called "indirect labels" are joined to the hybrid duplex after hybridization. Often, the indirect label is attached to a binding moiety that has been attached to the target nucleic acid prior to the hybridization. Thus, for example, the target nucleic acid may be biotinylated before the hybridization. After hybridization, an avidin-conjugated fluorophore will bind the biotin bearing hybrid duplexes providing a label that is easily detected. For a detailed review of methods of labeling nucleic acids and detecting labeled hybridized nucleic acids see *Laboratory Techniques in Biochemistry and Molecular Biology, Vol. 24: Hybridization With Nucleic Acid Probes*, P. Tijssen, ed. Elsevier, N.Y., (1993)).

The labels may be incorporated by any of a number of means well known to those of skill in the art. Means of attaching labels to nucleic acids include, for example nick translation, or end-labeling by kinasing of the nucleic acid and subsequent attachment (ligation) of a linker joining the sample nucleic acid to a label (e.g., a fluorophore).

The labels can be attached directly or through a linker moiety. In general, the site of label or linker-label attachment is not limited to any specific position. Thus, a label may be attached to a nucleoside, nucleotide, or analogue thereof at any position that does not interfere with detection or hybridization as desired. For example, certain Label-ON Reagents from Clontech (Palo Alto, Calif.) provide for labeling interspersed throughout the phosphate backbone of an oligonucleotide and for terminal labeling at the 3' and 5' ends. Labels can be attached at positions on the ribose ring or the ribose can be modified and even eliminated as desired. The base moieties of useful labeling reagents can include those that are naturally occurring or modified in a manner that does not interfere with the purpose to which they are put. Modified bases include but are not limited to 7-deaza A and G, 7-deaza-8-aza A and G, and other heterocyclic moieties.

4. Protein-based Assays

In addition to, or as an alternative to, the detection of chemokine mRNA level(s) after treatment with a test agent, the screening method of the invention can detect alterations in chemokine protein level(s) in response to the test agent.

a. Detection of Chemokine Proteins

Chemokine protein(s) can be detected and quantified by any of a number of methods well known to those of skill in the art. These may include analytic biochemical methods such as electrophoresis, capillary electrophoresis, high performance liquid chromatography (HPLC), thin layer chromatography (TLC), hyperdiffusion chromatography, and the like, or various immunological methods such as fluid or gel precipitin reactions, immunodiffusion (single or double), immunohistochemistry, affinity chromatography, immunoelectrophoresis, radioimmunoassay (RIA), enzyme-linked immunosorbent assays (ELISAs), immunofluorescent assays, Western blotting, and the like.

In a preferred embodiment, the chemokine protein(s) are detected/quantified in an electrophoretic protein separation (e.g. a 1- or 2-dimensional electrophoresis). Means of detecting proteins using electrophoretic techniques are well known to those of skill in the art (see generally, R. Scopes (1982) *Protein Purification*, Springer-Verlag, N.Y.; Deutscher, (1990) *Methods in Enzymology Vol. 182: Guide to Protein Purification*, Academic Press, Inc., N.Y.).

Another preferred embodiment utilizes a Western blot (immunoblot) analysis to detect and quantify the presence of chemokine protein(s) in the sample. This technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind the target protein(s).

The antibodies specifically bind to the target protein(s) and may be directly labeled or alternatively may be subsequently detected using labeled antibodies (e.g., labeled sheep anti-mouse antibodies) that specifically bind to the a domain of the antibody.

Other suitable assay formats include, but are not limited to, liposome immunoassays (LIA), which use liposomes designed to bind specific molecules (e.g., antibodies) and release encapsulated reagents or markers. The released chemicals are then detected according to standard techniques (see, Monroe et al. (1986) *Amer. Clin. Prod. Rev.* 5: 34–41).

In a preferred embodiment, the chemokine protein(s) are detected and/or quantified in the biological sample using any of a number of well recognized immunological binding assays (immunoassays) (see, e.g., U.S. Pat. Nos. 4,366,241; 4,376,110; 4,517,288; and 4,837,168). For a review of the general immunoassays, see also *Methods in Cell Biology Volume 37. Antibodies in Cell Biology*, Asai, ed. Academic Press, Inc. New York (1993); *Basic and Clinical Immunology* 7th Edition, Stites & Terr, eds. (1991).

Immunoassays) may utilize a "capture agent" to specifically bind to and often immobilize the analyte (in this case a chemokine protein). In preferred embodiments, the capture agent is an antibody.

Immunoassays also typically utilize a labeling agent to specifically bind to and label the binding complex formed by the capture agent and the analyte. The labeling agent may itself be one of the moieties comprising the antibody/analyte complex. Thus, the labeling agent may be a labeled protein or a labeled antibody that specifically recognizes the already bound target protein. Alternatively, the labeling agent may be a third moiety, such as another antibody, that specifically binds to the capture agent/protein complex.

Other proteins capable of specifically binding immunoglobulin constant regions, such as protein A or protein G may also be used as the label agent. These proteins are normal constituents of the cell walls of streptococcal bacteria. They exhibit a strong non-immunogenic reactivity with immunoglobulin constant regions from a variety of species (see, generally Kronval, et al. (1973) *J. Immunol.*, 111: 1401–1406, and Akerstrom (1985) *J. Immunol.*, 135: 2589–2542).

As indicated above, immunoassays for the detection and/or quantification of the chemokine protein(s) of this invention can take a wide variety of formats well known to those of skill in the art. Preferred immunoassays for detecting the target protein(s) are either competitive or noncompetitive. Noncompetitive immunoassays are assays in which the amount of captured analyte is directly measured. In competitive assays, the amount of analyte (chemokine protein) present in the sample is measured indirectly by measuring the amount of an added (exogenous) analyte displaced (or competed away) from a capture agent (antibody) by the analyte present in the sample. In one competitive assay, a known amount of, in this case, labeled protein is added to the sample and the sample is then contacted with a capture agent. The amount of labeled protein bound to the antibody is inversely proportional to the concentration of target protein present in the sample.

The assays of this invention are scored (as positive or negative or quantity of target protein) according to standard methods well known to those of skill in the art. The particular method of scoring will depend on the assay format and choice of label. For example, a Western Blot assay can be scored by visualizing the colored product produced by the enzymatic label. A clearly visible colored band or spot at the correct molecular weight is scored as a positive result, while the absence of a clearly visible spot or band is scored as a negative. The intensity of the band or spot can provide a quantitative measure of target protein concentration.

Antibodies useful in these immunoassays include polyclonal and monoclonal antibodies, which can be produced, for example, as described above.

5. Test Agent Databases

In a preferred embodiment, generally involving the screening of a large number of test agents, the screening method includes the recordation of any test agents that induces a difference in the level of chemokine mRNA or protein in a database of agents that induce or inhibit differentiation of fibroblasts to myofibroblasts.

The term "database" refers to a means for recording and retrieving information. In preferred embodiments the database also provides means for sorting and/or searching the stored information. The database can comprise any convenient media including, but not limited to, paper systems, card systems, mechanical systems, electronic systems, optical systems, magnetic systems or combinations thereof. Preferred databases include electronic (e.g. computer-based) databases. Computer systems for use in storage and manipulation of databases are well known to those of skill in the art and include, but are not limited to "personal computer systems", mainframe systems, distributed nodes on an inter- or intra-net, data or databases stored in specialized hardware (e.g. in microchips), and the like.

B. Prescreening for Specific Binding to Differentiation-Inducing Chemokine Nucleic Acid or Protein In certain embodiments, it is advantageous to prescreen test agents for the ability to interact with (e.g. specifically bind to) a differentiation-inducing chemokine nucleic acid or protein. Specifically binding test agents are more likely to interact with and thereby modulate chemokine expression and/or activity. As test agents that interact with the chemokine differentiation domain are particularly likely to modulate the activity of this domain, the prescreening method is preferably designed to detect specific binding of test agents to this domain.

Although the method can be used to screen for test agents that bind to any differentiation-inducing chemokine, the use of CXC chemokines is preferred. Exemplary preferred embodiments employ IL-8-, cCAF-, and MGSA or fragments thereof.

In one embodiment, such prescreening is accomplished with a simple in vitro binding assay, in which a differentiation-inducing chemokine nucleic acid or protein is contacted with a test agent and specific binding is detected. Means of assaying for specific binding or the binding affinity of a particular ligand for a nucleic acid or for a protein are well known to those of skill in the art. In preferred binding assays, the chemokine protein or nucleic acid is immobilized and exposed to a test agent (which can be labeled), or alternatively, the test agent(s) are immobilized and exposed to an chemokine or to a chemokine nucleic acid (which can be labeled). The immobilized moiety is then washed to remove any unbound material and the bound test agent or bound chemokine protein or nucleic acid is then detected.

As described above for the screening assay, test agents that specifically bind to a chemokine nucleic acid or protein can be recorded in a database of candidate agents that may induce or inhibit differentiation of fibroblasts to myofibroblasts.

C. Prescreening for Specific Binding to Receptor for Differentiation-Inducing Chemokine In additional embodiments, it is advantageous to prescreen test agents for the ability to interact with (e.g. specifically bind to) a receptor for a differentiation-inducing chemokine, preferably a receptor that interacts with the differentiation domain. Such test agents are candidates for agonists that mimic the differentiation-inducing activity of the chemokines described herein or antagonists that inhibit this activity.

Although the method can be used to screen for test agents that bind to a receptor for any differentiation-inducing chemokine, the use of receptors for CXC chemokines is preferred. Exemplary preferred embodiment employ receptors for IL-8-, cCAF-, and MGSA. Use of the method to prescreen for agents that bind to CXCR1 is particularly preferred, as IL-8 binds to the human form of this receptor and cCAF bind to the chicken form. Moreover, as shown in the Example, a cCAF N-terminal peptide including the differentiation domain binds to and activates this receptor. In another preferred embodiment, the method is used to prescreen for agents that bind to CXCR2, which is the primary chemokine receptor for MGSA, although IL-8 also binds to this receptor (but with lower affinity than to CXCR1).

In one embodiment, such prescreening is accomplished with a simple in vitro binding assay, in which the receptor is contacted with a test agent and specific binding is detected. Means of assaying for specific binding or the binding affinity of a particular ligand for a receptor are well known to those of skill in the art. In preferred binding assays, the chemokine receptor is immobilized and exposed to a test agent (which can be labeled), or alternatively, the test agent(s) are immobilized and exposed to a receptor (which can be labeled). The immobilized moiety is then washed to remove any unbound material and the bound test agent or bound chemokine receptor is then detected.

As described above, test agents that specifically bind to a receptor for a differentiation-inducing chemokinecan be recorded in a database of candidate agents that may induce or inhibit differentiation of fibroblasts to myofibroblasts.

All publications cited herein are explictly incorporated by reference.

VII. Example

The following example is offered to illustrate, but not to limit the claimed invention.

A. Introduction

Chemokines are small cytokines primarily known for their roles in inflammation. However, recently they have been implicated in processes involved in development of the granulation tissue of wounds but little is known about their functions during this process. Fibroblasts play key roles in this phase of healing: some fibroblasts differentiate into myofibroblasts, α-smooth muscle actin (α-SMA)-producing cells that are important in wound closure and contraction.

The following studies show that the CXC chemokine cCAF (chicken Chemotactic and Angiogenic Factor) stimulates fibroblasts to produce high levels of α-SMA and to contract collagen gels more effectively than do normal fibroblasts, both characteristic properties of myofibroblasts. Furthermore, application of cCAF to wounds in vivo increases the number of myofibroblasts present in the granulation tissue and accelerates wound closure and contraction. These effects in culture and in vivo can be achieved by a peptide containing the N-terminal 15 amino acids of the cCAF protein and that both the full protein and the N-peptide stimulate α-SMA expression independently of TGFβ. These studies demonstrate that chemokines play a major role in the differentiation of fibroblasts into myofibroblasts during formation of the repair tissue.

B. Materials and Methods

1. Materials

All tissue culture media and materials were purchased from Gibco-BRL. cCAF was either purified as described in Martins-Green and Feugate (1998) or synthesized by Gryphon Sciences (San Francisco, Calif.). The 15-amino acid N-terminal peptide was also synthesized by Gryphon Sciences. The 28-amino acid C-terminal peptide was synthesized by Milligen Biosearch (San Rafael, Calif.). Antibodies used: anti-α-SMA (Sigma: St. Louis, Mo.), anti-TGFβ1,2,3 (R&D Labs: Minneapolis, Minn.), anti-mouse horseradish peroxidase, anti-mouse Texas Red (Amersham: Piscataway, N.J.), anti-mouse Alexa (Molecular Probes: Eugene, Oreg.) and anti-mouse FITC (DAKO: Carpinteria, Calif.). The anti-cCAF rabbit serum was prepared by Robert Sargeant (Ramona, Calif.). Other materials used include: ECL reagents (Amersham); Vectashield mounting medium (Vector Laboratories, Burlingame, Calif.); DC protein assay kit (Bio-Rad, Hercules, Calif.); TRIzol reagent (Gibco-BRL, Rockville, Md.); Vitrogen 100 collagen (Cohesion Technologies, Palo Alto, Calif.); Biocclusive bandage (Johnson&Johnson Medical, Arlington, Tex.); and Classic 18S rRNA primers (Ambion, Austin, Tex.). TGFβ1 was a gift from A. Roberts (NIH).

2. Cell Cultures

Primary chicken embryonic connective tissue fibroblasts (CEFs) were cultured as previously described in Martins-Green and Feugate (1998). Briefly, these fibroblasts were isolated from 10-day-old chicken embryo body walls, plated at $6 \times 10^6$ cells/100 mm plate and cultured for 4 days in 199 medium with 5% donor calf serum, 1% chick serum and 0.3% tryptose phosphate broth. These cultures were passaged once (secondary cultures); the cells were plated at $0.4 \times 10^6$ cells/35 mm plate in 199/tryptose phosphate broth and 2% donor calf serum.

3. Fibroblast Growth Assay

Secondary fibroblasts were plated at $0.4 \times 10^6$ cells/35 mm plate and cCAF was added to experimental plates. For each experiment, plating efficiency was determined by trypsinizing plates four hours after plating. Cells were counted with a Coulter particle counter to confirm even plating of cells. The media was replaced approximately every 16 hr with 1 ml of serum free 199 medium containing 0.3% tryptose phosphate broth and 2% donor calf serum, and 100–1000 ng cCAF [9–90 nM] or C- or N-peptide [64–640 nM] was added to the experimental plates, whereas, control plates contained media only. On day 3, plates were trypsinized to remove all cells and cells were counted using a Coulter counter. To test for specificity, anti-cCAF rabbit serum was pre-incubated with cCAF (3 μl serum/750 ng cCAF [68 nM] or N-peptide [480 nM]) for 1 hr at room temperature before being added to cells.

4. Trypan Blue Staining

The supernatant of treated and untreated CEFs was collected, the cells centrifuged to a pellet and resuspended in a small volume of medium. 1% trypan blue was added to a final concentration of 0.5% trypan blue. Cells were stained for 5min and then counted in a hemocytometer. Necrotic cells stained blue.

5. Acridine Orange/Ethidium Bromide Staining

Plates of fibroblasts treated with cCAF as described above were rinsed twice with PBS and incubated in 0.1 mg/ml acridine orange/ethidium bromide in PBS for 1 min. After rinsing twice with PBS and adding a cover slip, the cells were immediately viewed by epifluorescence microscopy and random fields were photographed. The number of cells with blebbing cytoplasm and fragmented nuclei were counted from the entire field of each photograph. As a positive control, human umbilical vein endothelial cells were counted at 6 hr after serum withdrawal, which causes these cells to exhibit the classical morphological features of apoptosis.

6. Immunostaining

Plates of fibroblasts were treated with cCAF as described previously. After 4 days, the cells were rinsed with PBS, fixed in 4% paraformaldehyde, permeabilized with 0.15% Triton X-100 and incubated with PBS containing 0.1M glycine for 10 min. Cells were blocked for 30 min with 10% goat serum in PBS, incubated with mouse anti-α-SMA, to a final IgG concentration of 20 μg/ml, in 1% BSA/PBS for 1hr at room temperature (RT), and washed three times with 0.1% BSA/PBS for 10 min each. The cells were then incubated in goat anti-mouse FITC or sheep anti-mouse Texas Red (1:100) in 1% BSA/PBS for 1 hr at RT, washed three times for 10 min with 0.1% BSA in PBS and mounted with Vectashield. Collagen gels were rinsed with PBS, fixed in 4% paraformaldehyde for 2 hr, washed three times 30 min each with PBS, and incubated for an additional 30 min in PBS containing 0.1M glycine. This treatment was followed by incubation at 4° C. overnight in 15% sucrose and then incubated under the same conditions in 30% sucrose. After a brief rinse with PBS, the gels were frozen in OCT, sections prepared and collected on gelatin-coated slides, rinsed with PBS, fixed in 4% paraformaldehyde for 10 min, and then incubated again in PBS containing 0.1M glycine for 10 min. This was followed by blocking for 30 min with 10% goat serum in PBS, incubation in primary and secondary antibody as described above, and mounting with Vectashield.

7. Immunoblotting

Plates of fibroblasts were treated as described previously, with 750 ng/ml cCAF or 2.5 ng/ml TGFβ. To block TGFβ, or cCAF activity, anti-cCAF (3 μl) or anti-TGFβ (1 μl) antibody was pre-incubated in 1 ml media for 1 hr at room temperature before being added to cells. After 4 days of treatment, protein extracts were prepared in 1 ml 150 mM RIPA buffer containing protease inhibitors. Protein concentrations were determined using the DC protein assay kit and samples were adjusted to contain equal amounts of protein. SDS-PAGE was performed on 7.5% separating Doucet gels (Doucet and Trifaro, 1988). Protein transfer to nitrocellulose was performed using a wet-transfer apparatus (Bio-Rad) at 100V for 45 min. The membranes were blocked for 1 hr in 5% milk in TTBS and then incubated overnight at 4° C. in mouse anti-α-SMA, to a final IgG concentration of 5 μg/ml, in 1% milk in TTBS. The membranes were washed 3 times for 20 min each with TTBS, incubated in anti-mouse HRP at 1:10,000 in 1% milk for 1hr and washed as above, and the bands visualized using the ECL.

8. Collagen Gel Contraction 1.5 ml Vitrogen 100 collagen gels were made in 35 mm plates. Secondary fibroblasts were plated at $0.4 \times 10^6$ cells/35 mm plate on top of the gels. After the cells had adhered to the collagen, cCAF was added to experimental plates. The medium was replaced approximately every 16 hr with 1 ml of 199 supplemented with 0.3% tryptose phosphate broth and 2% donor calf serum, and 750 ng cCAF [68 nM] or N-peptide [480 nM] was added to the experimental plates. Control plates contained media only. After 4 days, gels were released. Treatment was continued for 2 more days and gels were photographed every 12 hours. The photographs were used for evaluation of gel contraction by determining the area of the gel using NIH image analysis.

9. RT-PCR

Total RNA for α-SMA was extracted using TRIzol reagent from untreated fibroblasts, fibroblasts treated with 750 ng/ml cCAF or fibroblasts treated for varying periods of time with cCAF. The RT-PCR procedure was performed using the Promega Access RT-PCR System, which is designed to finish reverse transcription (RT) and polymerase chain reaction (PCR) in one tube, and following the protocol recommended by Promega, except that 1.5 times the recommended amount of dNTP, reverse transcriptase and Tfl DNA polymerase were used to ensure strong synthesis of 18S ribosomal RNA. The reaction conditions included: 1 μg total RNA, first strand synthesis at 48° C. for 45 min, then 95° C. for 5 min to inactivate the reverse transcriptase, followed by DNA amplification at 95° C. for 45 sec, 58° C. for 60 sec, 68° C. for 90 sec for 40 cycles. Finally, 68° C. for 7 min to extent the strands. 2 μl of Quantum mRNA classic 18S primers (Ambion) were added to reaction to produce the control band. The followin primers used for the amplification of α-SMA:

```
sense primer: 5'GGAGCACCTGAGGACATTGAC   SEQ ID NO:12 antisense     5'GCTTCAGTCAGCAGAGTTGGG   SEQ ID NO:13
primer:
```

RT-PCR products were analyzed by electrophoresis in 1.5% agarose and the density of the bands was measured by densitometry using Glyko BandScan.

10. Wounding Experiment

Full-thickness excision wounds (approximately 0.5×0.5 cm) were made, using a scalpel blade, on the underside of the wings of 2-week-old chicks. The left wing was treated with vehicle alone (water), and the right wing with 1 μl cCAF [90 nM]. The wounds were photographed immediately after wounding and then covered with Biocclusive bandage. 50 μl vehicle (water) or cCAF was deposited through the bandage onto the wound using a 30-gauge needle. This procedure was repeated the next day and every other day thereafter. On days 3, 5 and 7, the bandages were removed and the wounds were photographed before replacing the bandages and applying the treatment again.

11. Preparation and Staining of Wing Sections

At the specified time points, chickens were euthanized with sodium pentobarbitol. The wounded wings were collected and fixed for 18 hrs in 4% paraformaldehyde and decalcified for 3 days in 5% formic acid, 2.5% formaldehyde at 4° C. The tissue was embedded in paraffin and sectioned. Sections were stained with Masson Trichrome to visualize interstitial collagen. Other sections were immunolabeled for α-SMA. Sections were deparaffinized with 3×15 min washes in Hemo-De and rehydrated in 5 min washes of ethanol (100%, 95%, 70%, 50%, 30%). After rinsing with PBS, sections were fixed in 2% paraformaldehyde 1 hr. General autofluoresence and non-specific staining were blocked by 30 min in 0.1M glycine in PBS, followed by 30 min in 1% Evans Blue in PBS to quench red blood cell autofluorescence. Sections were incubated with α-SMA antibody in 1% BSA in PBS (1:50) for 2 hr at room temperature. After 3×10 min washes in 0.1% BSA in PBS, the sections were incubated for 40 min with anti-mouse Alexa antibody in 1% BSA in PBS (1:200). They were then washed and mounted with Vectashield.

12. Assay of Chicken cCXCR1-mediated Calcium Release

NIH #373 cells overexpressing the chicken CXC receptor 1 (CXCR1) were exposed to the full-length cCAF molecule, the 15-amino N-terminal peptide of cCAF, or the 28-amino acid C-terminal peptide and calcium release was then measured.

13. Statistical Methods

Significance was determined using Student's t-test for comparison between 2 means and ANOVA for comparison between more than 2 means. All data were examined to assure homogeneity of variance. Means were considered significantly different when $p<0.05$.

C. Results

1. Effects of cCAF on Fibroblast Growth

To determine the effects of cCAF on fibroblast growth, primary chicken embryonic connective tissue fibroblasts were cultured in the presence of 2% donor calf serum. Embryonic fibroblasts behave much like wound fibroblasts (Brown et al., 1993) and the presence of a small amount of serum in the medium mimics the conditions of the wound, where serum factors are abundant. Because these are primary fibroblasts rather than cell lines, there are variations in the levels of responses in cells isolated from different embryos. As a consequence, internal controls were always included and results from different batches of cells were not averaged. Therefore, all figures depict a representative experiment out of several performed for each type of experiment.

When fibroblasts are cultured in the presence of serum, cCAF suppresses proliferation of these cells by 25% compared to untreated cells (FIG. 1, $p<0.01$). This effect is dose-dependent, with the greatest suppression occurring at 500–750 ng of cCAF/ml of medium (FIG. 1A) and at 2 days after plating (not shown). Although chemokine concentrations of $10^{-2}$–10 ng/ml can chemoattract and activate leukocytes, chemokines acting on other cell types such as endothelial cells, smooth muscle cells and fibroblasts require concentrations in the range of $10^2$ ng/ml (Gupta et al., 1994; Gharaee-Kermani et al., 1996; Luo et al., 1996). This is within physiological range; wound fluid from burn patients has MGSA concentrations of $10^2$–$10^3$ ng/ml at 6–7 days after injury (Rennekampff et al., 1997). To further test whether the cCAF effect on fibroblast growth is specific, we performed experiments using an antibody specific for cCAF and showed that this antibody abrogates the effects of this chemokine on proliferation (FIG. 1B).

Figure 2:
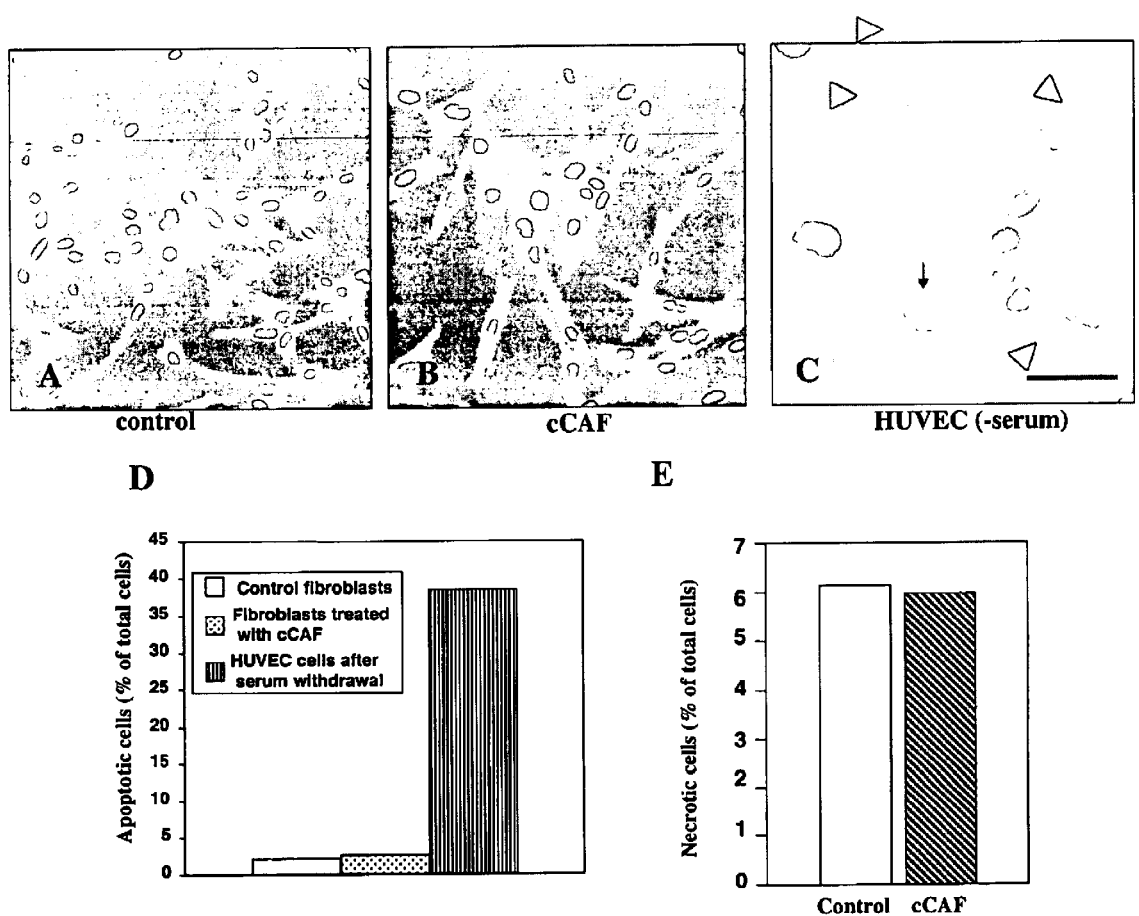
FIG. 2: The effects of cCAF on cell death. cCAF-treated fibroblasts were stained with acridine orange/ethidium bromide to determine whether this chemokine induces the nuclei fragmentation and blebbing of the cytoplasm that are characteristic of apoptotic cells. Control fibroblasts (A) and fibroblasts treated with cCAF (B) do not show the characteristics of apoptotic cells. (C) HUVEC cultured in the absence of serum served as the positive control; these cells undergo the classical apoptotic cell death after serum withdrawal and show cytoplasmic blebbing (arrowheads) and nuclear fragmentation (arrow). Scale bar=150 $\mu$m (D)) Quantification of the observations made in A–C (performed as described in Materials and Methods). (E) Cells incubated with trypan blue, which stains necrotic cells blue, showed that cCAF does not stimulate cell necrosis. The results shown represent one of three experiments.

Although the decrease in growth induced by cCAF is significant, it is not large. Therefore, we examined the possibility that this reduction in cell numbers was due to increased cell death. Cells grown under the same conditions as above were stained to detect apoptotic and necrotic cell death. Acridine orange/ethidium bromide staining was used to detect morphological features of apoptotic cells and trypan blue to detect necrotic cells. Staining of both untreated fibroblasts, and those treated with cCAF, with orange/ethidium bromide showed that these cells have a compact cytoplasm and an intact nucleus characteristic of healthy cells (FIG. 2A&B). In contrast, human umbilical vein endothelial cells (HUVEC) induced to apoptose by serum withdrawal showed characteristic blebbing of the cytoplasm and fragmentation of the nuclei typical of cells that are undergoing apoptosis (FIG. 2C&D). Similar studies performed to detect whether cCAF induced necrotic cell death showed that this chemokine does not cause cells to undergo necrosis (FIG. 2E).

Figure 3:
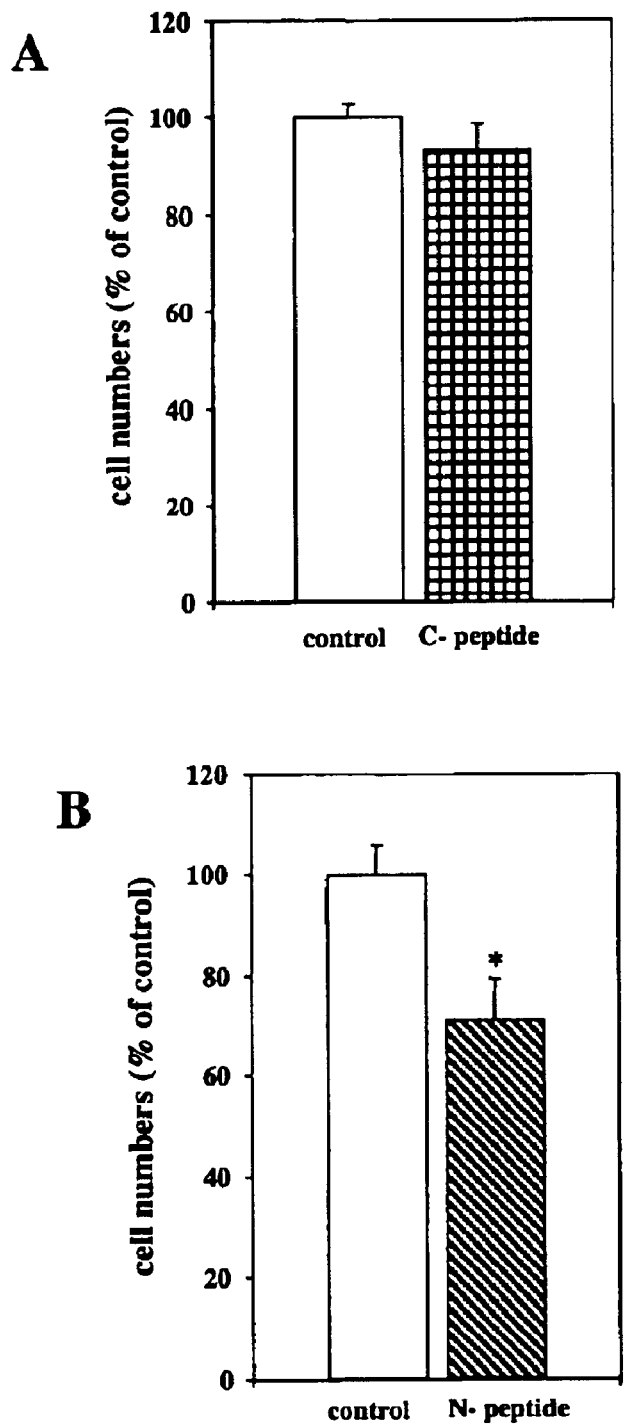
FIG. 3: Effects of the C- and N-peptides of the cCAF protein on fibroblast growth. Treatment with the angiogenic C-peptide (28 amino acids) did not suppress the growth of connective tissue fibroblasts (A) whereas treatment with the N-peptide (16 amino acids) shown in Table 3 suppresses the growth of fibroblasts to a level similar to that caused by the whole cCAF molecule (B). Results shown are representative of three independent experiments. (*=$p<0.05$).

We have previously shown that the C-terminal peptide (28 amino acids) of cCAF is by itself angiogenic in vivo (Martins-Green and Feugate, 1998; Martins-Green and Kelly, 1998). Therefore, we tested the possibility that these effects of cCAF on fibroblast growth are also mediated by the C-terminus of the molecule. Cells were treated with the C-terminal peptide following the same regimen of treatment as for cCAF itself. We found that this peptide did not cause a decrease in cell numbers (FIG. 3A). It has been shown for several chemokines that their chemotactic properties for leukocytes require the N-terminus of the protein (Strieter et al., 1995; Clark-Lewis et al., 1995; Weber et al., 1996; Baggiolini et al., 1997, Martins-Green and Feugate, 1998). Treatment of fibroblasts with the first 16 amino acids of the N-terminus (N-peptide) resulted in a decrease in growth similar to that induced by cCAF (FIG. 3B). Furthermore, the dose- and time-dependent pattern of suppression of growth induced by the N-peptide was the same as that of the whole cCAF molecule, albeit at a higher molar concentration (not shown).

2. cCAF Stimulates α-SMA Expression

Figure 4:
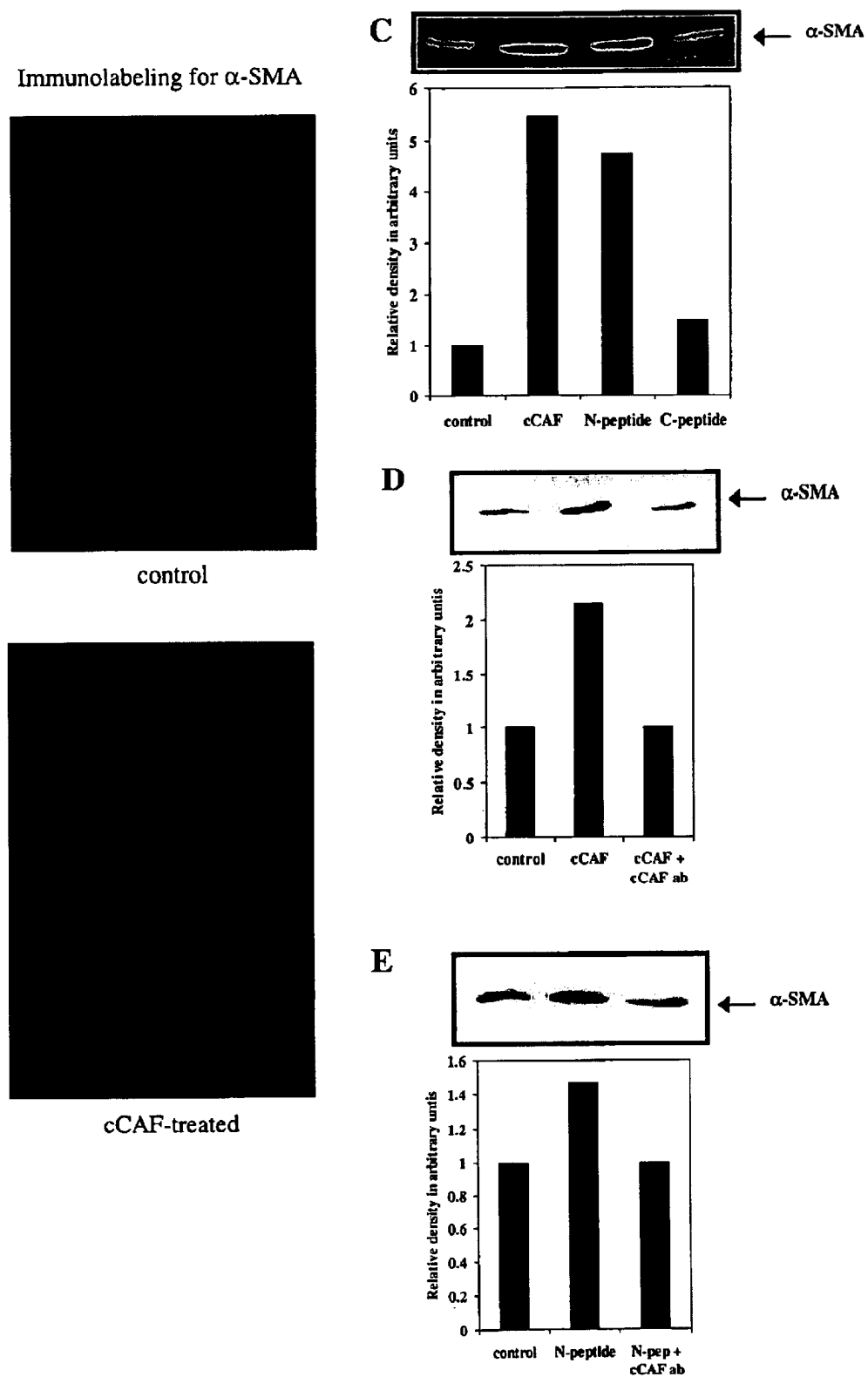
FIG. 4: Effect of cCAF and the N-peptide on myofibroblast differentiation. (A) Untreated embryonic connective tissue fibroblasts were immunolabeled for α-SMA, a marker for myofibroblast differentiation. Some fibroblasts show a small amount of staining for this protein, which is characteristic of fibroblasts in culture. (B) Cultures treated with cCAF for 3 days show that more fibroblasts are stained for α-SMA, that more fibrils are present in the cells, and that the staining is more intense than for untreated cells. Scale bar=100 μm (C) Immunoblot analysis for α-SMA to quantify the results observed in (A) and (B). All lanes contain equal amounts of total protein, as measured by the DC protein assay (BioRad). Cells treated with 750 ng/ml of cCAF or of the N-peptide show much higher levels of α-SMA when compared with untreated or C-peptide treated cells. Inhibition of cCAF (D) or N-peptide (E) with an anti-cCAF antibody blocks the increase in α-SMA expression.

The results described above show that the decrease in cell numbers induced by cCAF is specific and not due to cell death but that the effect is small and requires 2–3 days to be detected. This suggests that cCAF may play a role in triggering fibroblasts to slow down growth and develop a differentiated phenotype with a consequent decrease in cell division. Therefore, we investigated the possibility that cCAF stimulates differentiation of fibroblasts into myofibroblasts, cells that play an important role in wound closure and proliferate at a slower rate than normal fibroblasts (Masur et al., 1996; Nedelec et al., 1998; Dmitrijevic-Bussod et al., 1999: Khouw et al., 1999). Immunolabeling of fibroblasts treated with cCAF with an antibody specific for α-SMA, a marker for myofibroblasts, revealed the presence of many more cells showing intense staining for fiber bundles whereas control cells showed fewer and less brightly stained fibers (FIG. 4A&B). Immunoblot analysis of cell extracts using this antibody showed increased levels of α-SMA in cells treated with cCAF or the N-peptide compared to cells treated with the C-peptide and control cells (FIG. 4C). Inhibition of cCAF or N-peptide function by treatment of the cells in the presence of the cCAF antibody abrogated the increase in α-SMA expression (FIG. 4D&E).

Figure 5:
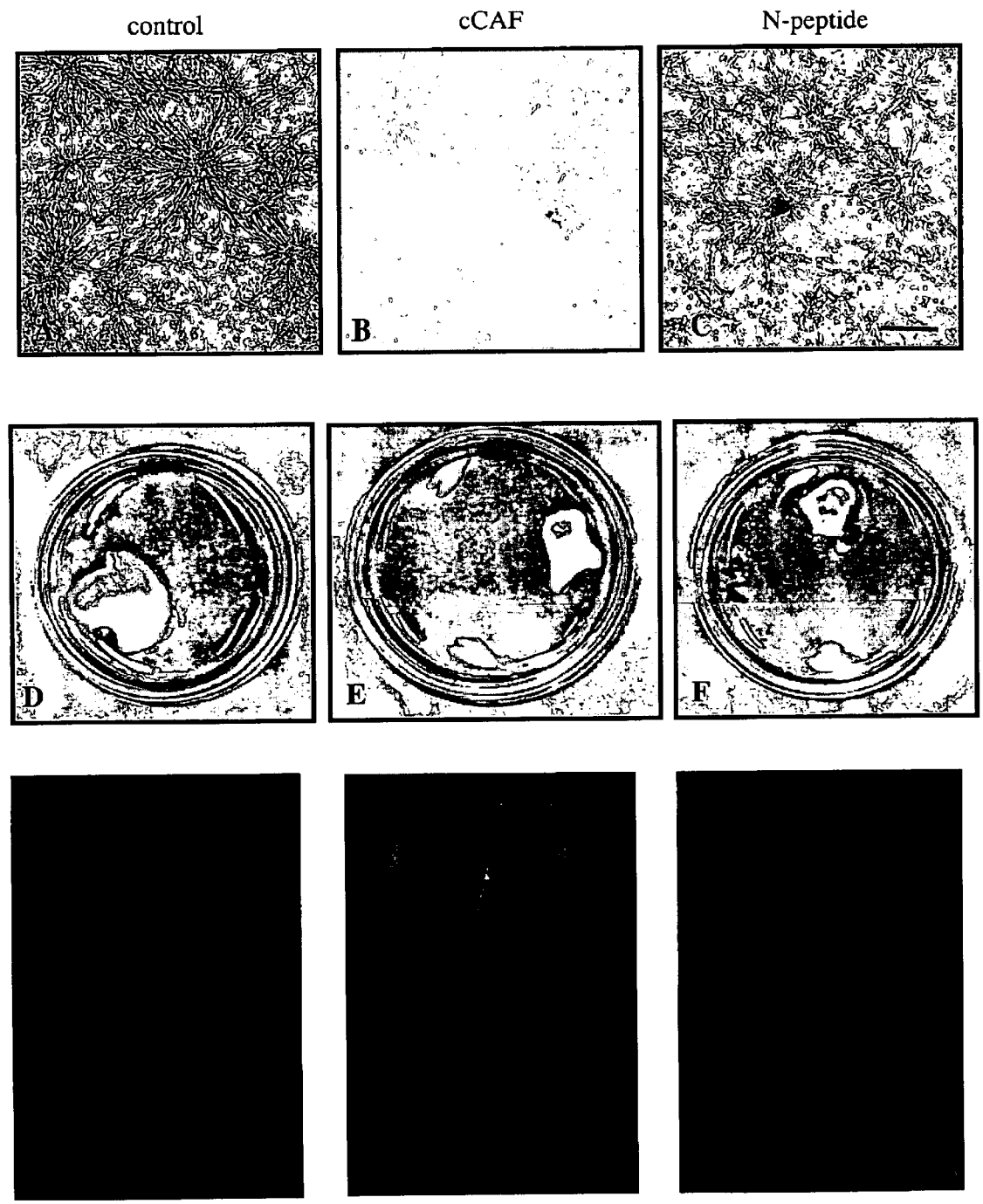
FIG. 5: Increase in collagen gel contraction by fibroblasts treated with cCAF. (A–C) Untreated fibroblasts plated on collagen gels form loose clusters (A) whereas fibroblasts treated with cCAF (B) or N-peptide (C) form clusters that are much tighter and generally pull away from the collagen. Scale bar=100 μm. (D–F) Collagen gels, 2 days after release from the edge of the culture dish show moderate contraction for untreated cells (D) but much greater contraction for cells treated with cCAF (E) or N-peptide (F). (G–I) Sections through the gels depicted in (D–F) were immunolabeled for α-SMA to show the presence of cells containing α-SMA. The staining is much less intense in untreated cells (G) than in cells treated with cCAF (H) or N-peptide (I). Scale bar=100 μm.
Figure 6:
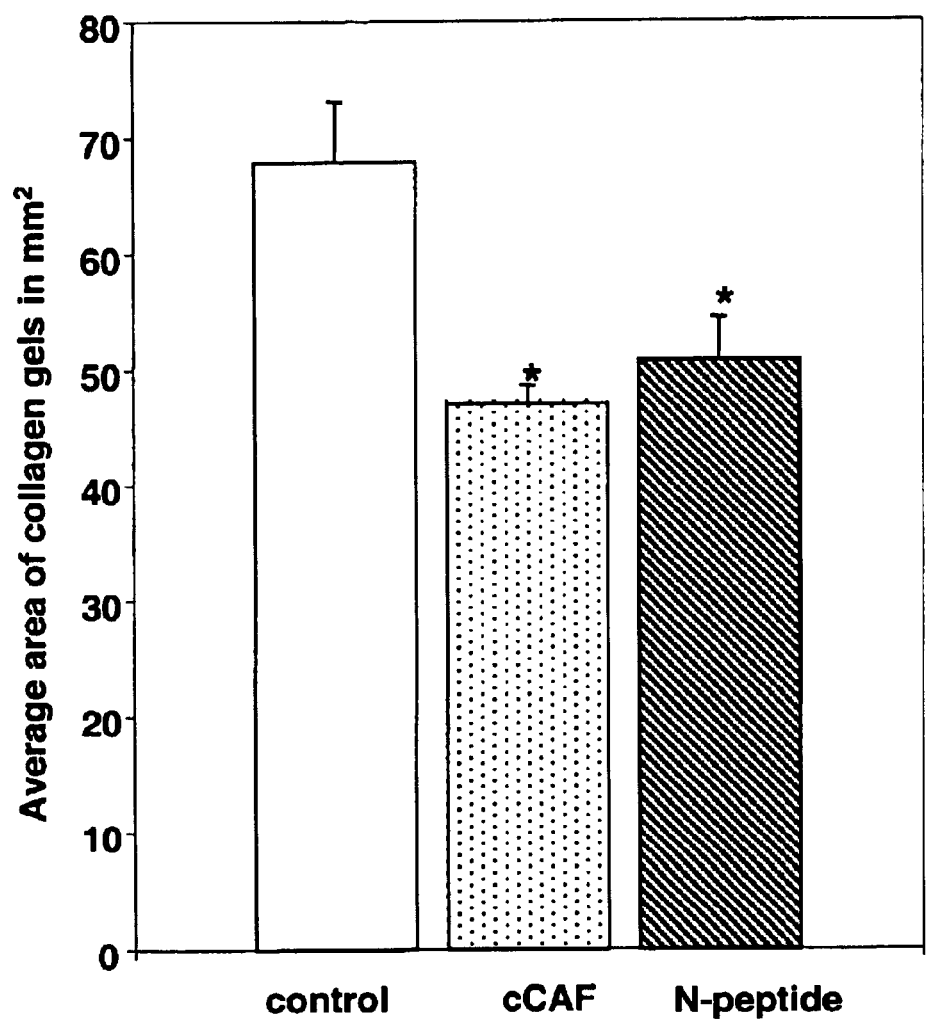
FIG. 6: Quantitation of cCAF- and N-peptide-induced contraction of collagen gels by fibroblasts. Fibroblasts were seeded on collagen gels, treated with 750 ng/ml cCAF or N-peptide for 4 days and then allowed to contract by releasing the gels from the dish. Contracting gels were photographed every day and areas of contracted gels were measured and analyzed using NIH Image software. Both treatments stimulated fibroblasts to contract collagen gels more efficiently than untreated cells. (*=p<0.05).

To determine whether this increase in α-SMA results in a functional phenotype, we examined the effect of cCAF on contraction of fibroblast-seeded collagen gels. Fibroblasts plated on collagen often grow in clusters but cellular clusters in plates treated with cCAF or N-peptide were more contracted than clusters in control cells (FIG. 5A–C). When collagen gels were released after 4–5 days of treatment, cCAF or N-peptide-treated cells contracted the gels more tightly than did untreated cells (FIG. 5D–F). Immunolabeling of sections prepared from collagen gels with the antibody to α-SMA showed that treated gels contain more cells with fibers staining for α-SMA than control gels (FIGS. 5G–I). FIG. 6 shows a quantitative analysis of cCAF- and of N-peptide-induced collagen gel contraction.

Figure 7:
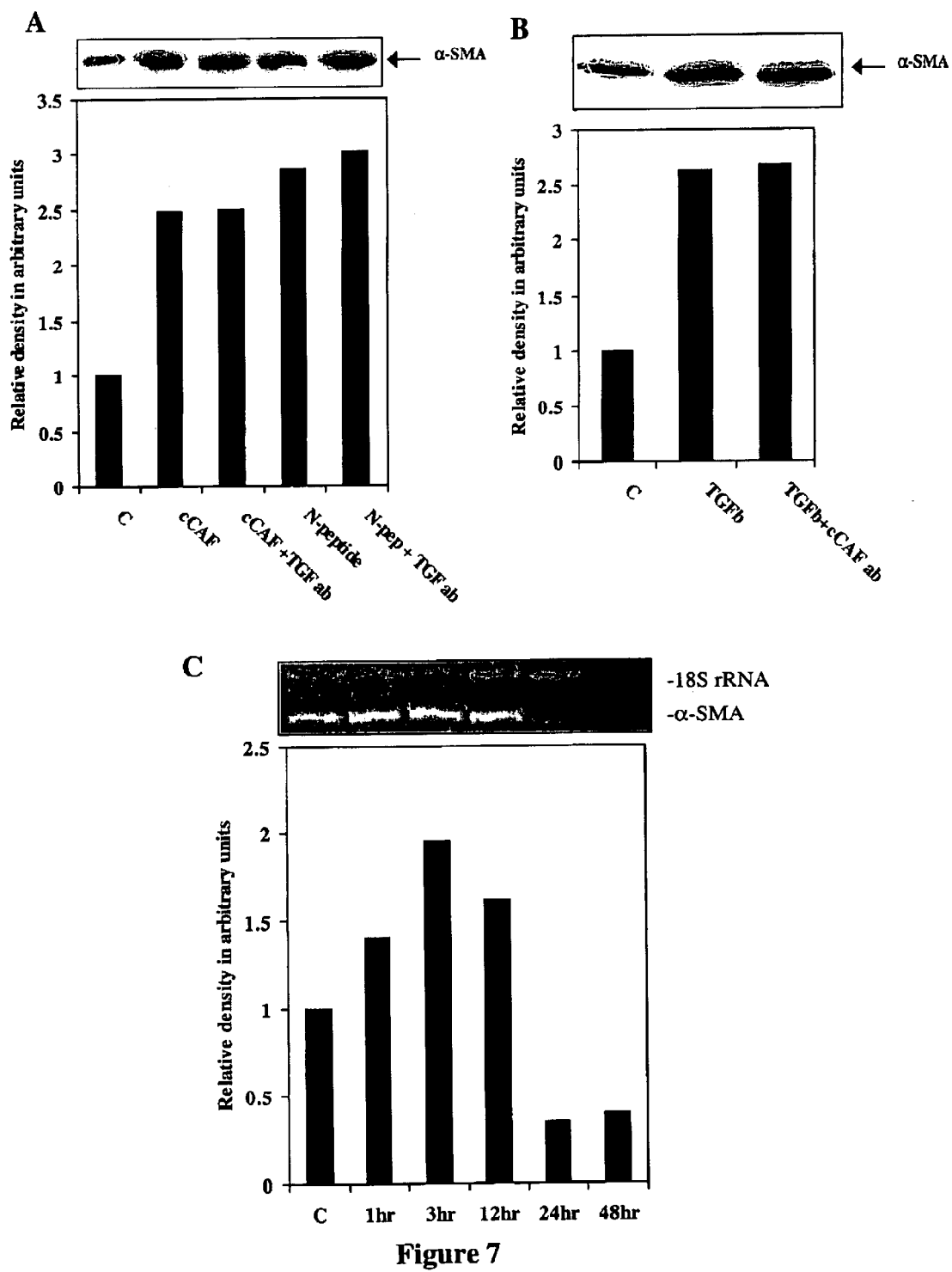
FIG. 7: Stimulation of α-SMA expression in cells treated with cCAF or TGFβ. (A) Cells treated with 750 ng/ml of cCAF or of the N-peptide in the presence or absence of a function-blocking antibody against TGFβ. Controls consisted of cells treated with the antibody alone. α-SMA production by cells treated with the chemokine or N-peptide alone was not affected by inhibition of TGFβ. (B) Treatment with the anti-cCAF antibody does not block the increase in α-SMA expression stimulated by treatment with 2.5 ng/ml TGF. Controls consisted of cells treated with just the antibody. (C) Fibroblasts were treated with cCAF for 1–48 hr, total RNA extracted using TRIzol reagent and RT-PCR was performed as described in the Materials and Methods. RT-PCR reveals increasing amounts of α-SMA mRNA relative to control from 1–12 hr after initiation of treatment. A fragment of the 18S rRNA was used as control to normalize the data.

Because TGFβ is a well-known stimulator of myofibroblast differentiation and because other molecules that stimulate α-SMA expression appear to do it via this growth factor (Desmouliere et al., 1993; Serini and Gabbiani, 1999), we investigated whether cCAF acts indirectly to induce α-SMA through the stimulation of TGFβ activity. Blocking TGFβ function by using an antibody against TGFβ1,2,3 did not affect the increase in α-SMA levels stimulated by cCAF (FIG. 7A). In addition, TGFβ stimulation of α-SMA is not affected by an antibody against cCAF (FIG. 7B). To confirm that cCAF directly stimulates α-SMA mRNA expression, we used RT-PCR with specific primers to the chicken molecule to examine the effects of cCAF on mRNA levels. This chemokine causes an increase in α-SMA mRNA levels within 1 hr of treatment and mRNA levels remain elevated for up to 12 hr after treatment before dropping below control levels by 24 hours (FIG. 7C).

3. cCAF-induced Effects on Wound Closure

Figure 8:
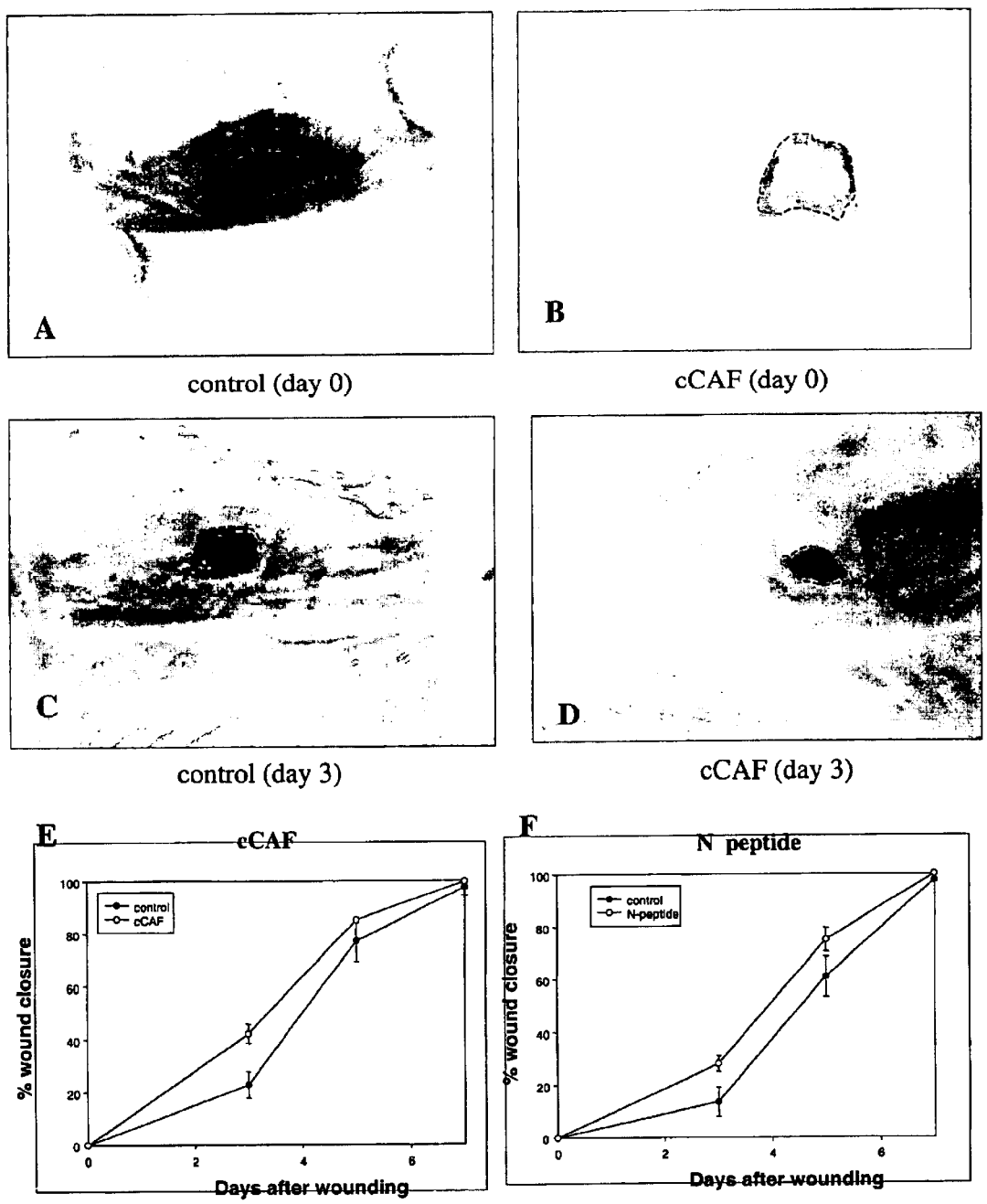
FIG. 8: Accelerated closure of wounds treated with cCAF or with N-peptide. Excision wounds were made on the underside of chick wings and then treated every other day with vehicle ($H_2O$) or 1 μg cCAF. The dashed lines trace the edges of the wounds. The underlying muscle can be seen within the wounds. Control wings (A&C) show less wound closure at day 3 than cCAF-treated wounds (B&D). (E) Average percent wound closure in 8 birds for cCAF or vehicle treatment. (F) Average percent wound closure of 8 birds/treatment with N-peptide or vehicle. Areas of the wounds were determined from digital photographs using NIH Image software. Percent wound closure was calculated by comparing the area of the closing wound to the area of the same wound on day 0. At day 3, p<0.05 for both treatments.

In wounded tissue, myofibroblast differentiation contributes to closing of wounds (Nedelec et al., 1998). Our finding that cCAF stimulates fibroblasts to acquire myofibroblastic phenotype and function in culture led us to determine whether cCAF affects wound closure in vivo. Full thickness and same size excision wounds were made on the underside of wings of 2 week-old chicks and for each bird one wing was treated with vehicle (H$_2$O) and the other with 1 μg of cCAF every other day. The bandages were removed at days 3, 5, and 7, and the wounds were photographed, dressed with clean bandages and treatments applied. For each wound, rate of wound closure was examined by taking digital photographs of the same wound through time and then determining the areas of the wounds from the photographs using NIH Image. FIGS. 8A&C show a wounded wing before and after 3 days of treatment with vehicle, whereas FIGS. 8B&D show the contralateral wing of the same bird, treated with cCAF at the same times. FIG. 8E shows the results of analyzes and comparison of the wound areas of several birds over time. On day 3, the cCAF-treated wounds had closed to a significantly greater degree than the vehicle-treated wounds. At day 5, the closure of the control wounds was still less than that of the experimental wounds but closure in the controls may have accelerated during this period. Although cCAF-treated wounds close faster, by day 7 both control and treated wounds were completely closed. Wounds treated with the N-peptide also showed accelerated wound closure during days 0–3, albeit less strongly than with the whole cCAF molecule (FIG. 8F).

Figure 9:
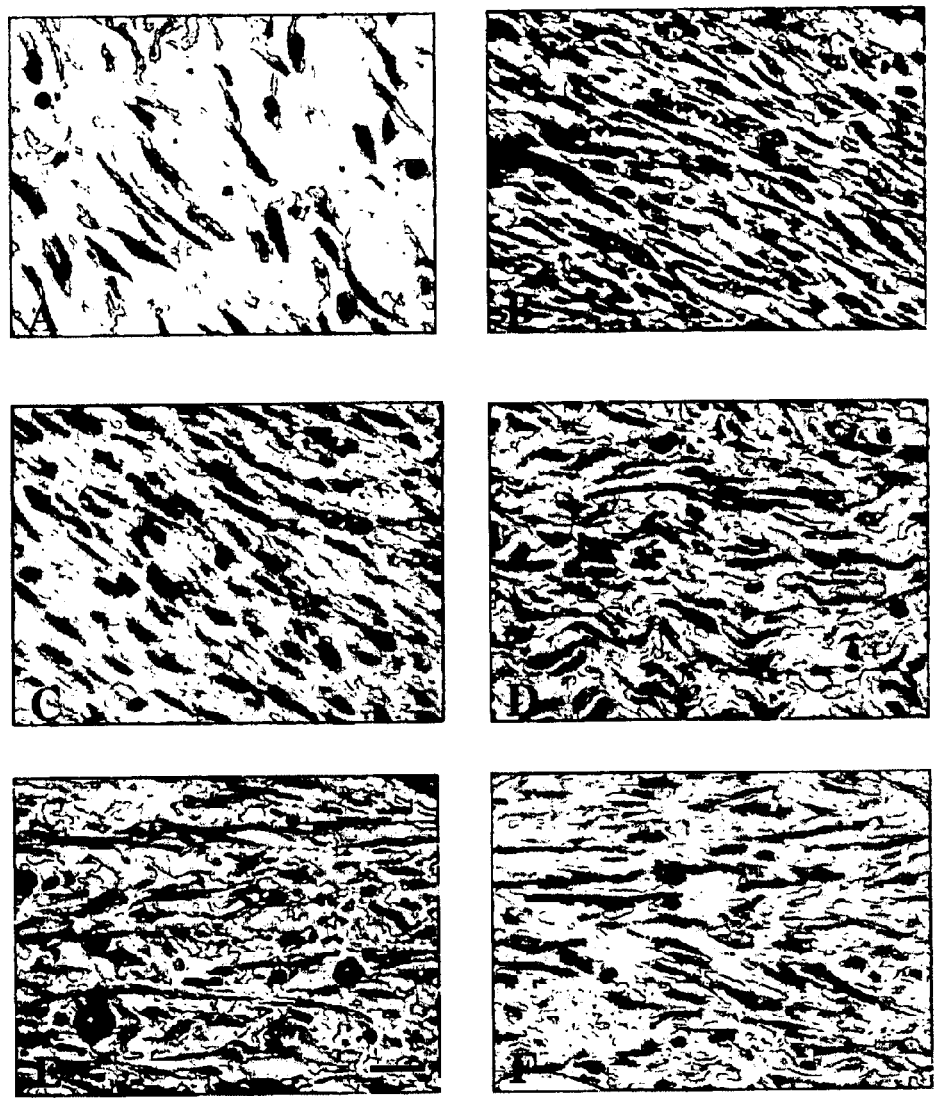
FIG. 9: Histology of excision wounds treated with cCAF. Paraffin-embedded sections of excision wounds, stained with Masson Trichrome. At 3 days after wounding, control wounds (A) have much less dense granulation tissue than those treated with cCAF (B). By day 5, the granulation tissue of the control wounds (D) resembles the tissue of the treated wounds at day 3(B). The cCAF-treated wounds continue to have denser repair tissue than the control wounds on day 5 (C). By day 7, the difference between the control wounds (E) and cCAF-treated wounds (F) is minimal. Scale bar=25 μm.

Sections through the wounds show that the granulation tissue of cCAF-treated wounds appears more dense earlier in wound healing (days 3&5) than the tissue of the wounds treated with vehicle (FIG. 9A–D). In particular, the granulation tissue of the control wounds at day 5 (FIG. 9C) resembles that of the cCAF-treated on day 3 (FIG. 9B). By day 7, the cCAF-treated wounds appear to be already remodeling whereas those treated with vehicle looked much like the granulation tissue of cCAF-treated wounds at 5 days (FIG. 9E–F). It is known that wound contraction causes the healing tissue to become more dense and compact, therefore our findings strongly suggest that cCAF stimulates early wound contraction and closure.

Figure 10:
FIG. 10: Immunostaining for α-SMA in the granulation tissue of excision wounds treated with cCAF. Paraffin-embedded sections of excision wounds treated every other day with vehicle ($H_2O$) or 1 μg cCAF were immunostained with an antibody against α-SMA. At 3 days after wounding, control wounds (A) show almost no cells labeling for α-SMA whereas those treated with cCAF show already numerous cells labeling for α-SMA (B). At day 5, cCAF-treated wounds (D) continue to show many more myofibroblasts than the control wounds (C). By day 7, cCAF-treated wounds (F) continue to have more labeled cells than do control wounds (E), but the difference is greatly diminished. Scale bar=88 μm.
Figure 10:
Figure 10:
Figure 10:
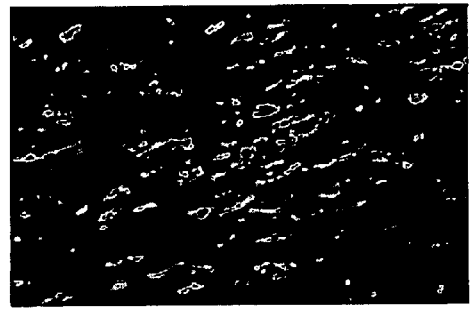
Figure 10:
Figure 10:

In order to test whether this acceleration in wound contraction and closure was due to an increase in the number of myofibroblasts in the granulation tissue, we immunostained vehicle-treated and cCAF-treated wounds for α-SMA (FIG. 10). At day 3, the granulation tissue of the cCAF-treated wounds has many more cells that label for α-SMA (FIG. 10B) than does the tissue of vehicle-treated wounds (FIG. 10A). On day 5, there continue to be many more cells staining for α-SMA in the cCAF-treated wounds (FIG. 10D) than in the control tissue (FIG. 10C). By day 7, this effect is no longer seen; the treated and untreated wounds have similar staining for myofibroblasts (FIGS. 10E&F). The earlier appearance of α-SMA-staining cells in wounds treated with cCAF suggests that the acceleration of wound contraction by cCAF is due to an increase in myofibroblasts at the early stages of wound repair.

Figure 11:
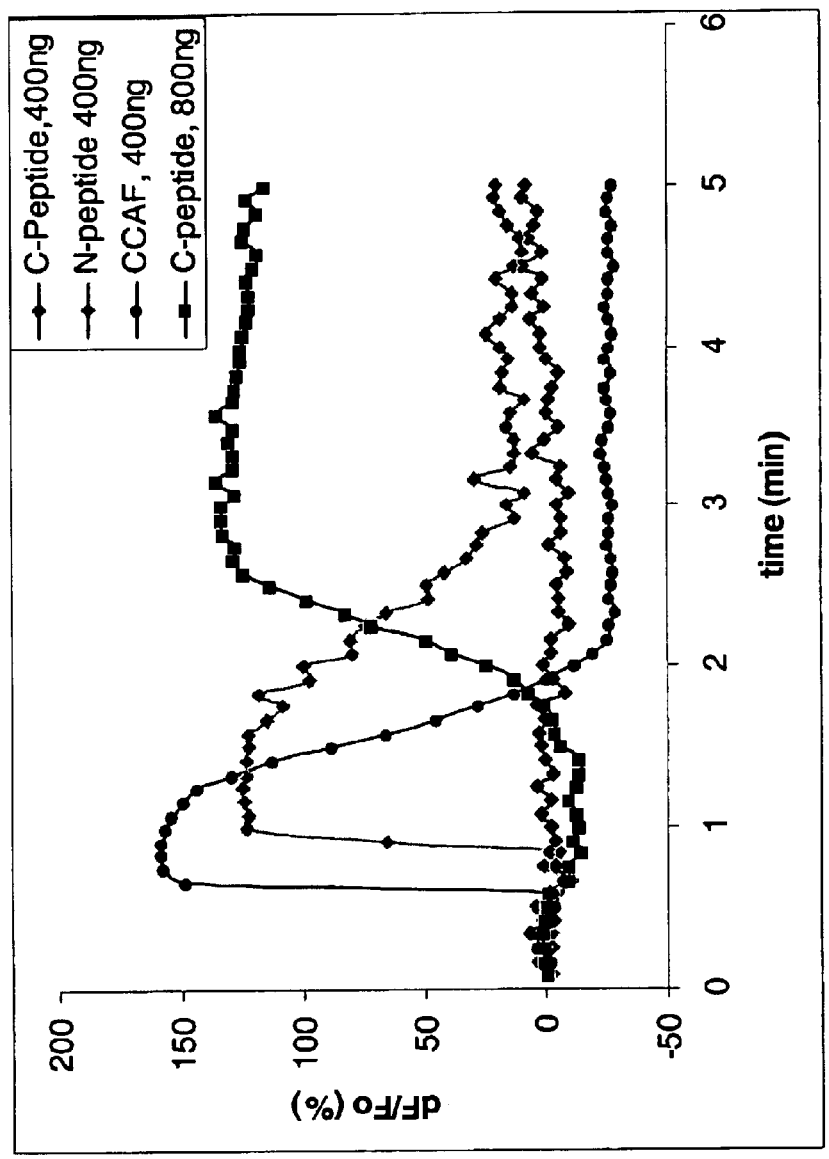
FIG. 11: Summary of cCAF and N-peptide effects on cCXCR1. NIH #373 cells overexpressing the chicken CXC receptor 1 (CXCR1) were exposed to the full-length cCAF molecule, the 15-amino N-terminal peptide of cCAF, or the 28-amino acid C-terminal peptide. Treatment with 400 ng cCAF induced a rapid (within 1 min.) release of calcium, which declined equally rapidly. Treatment with the same amount of N-peptide induced a similar, albeit somewhat slower, release. The C-peptide, in contrast, failed to induce calcium release at 400 ng. Increasing the C-peptide dose to 800 ng resulted in a release of calcium that was similar in magnitude, but differed in time course from the N-peptide-induced release.

4. Effects of cCAF and cCAF N- and C-terminal Peptides on Chicken CXCR1-mediated Calcium Release As shown in FIG. 11, treatment with 400 ng cCAF induced a rapid (within 1 min.) release of calcium, which declined equally rapidly. Treatment with the same amount of N-peptide induced a similar, albeit somewhat slower, release. The C-peptide, in contrast, failed to induce calcium release at 400 ng. Increasing the C-peptide dose to 800 ng resulted in a release of calcium that was similar in magnitude, but differed in time course from the N-peptide-induced release.

D. Discussion

The work presented here shows that the CXC chemokine, cCAF, suppresses fibroblast growth to about 75% of untreated cells, in a time- and dose-dependent manner. This decrease in growth is not due to cell death but rather it correlates with cCAF-induced expression of the myofibroblast marker, α-SMA. The expression of α-SMA in cCAF-treated cells results in an increase in the ability of the fibroblasts to contract collagen gels. All of these effects are specific and can be accomplished by the N-terminal peptide of the cCAF molecule by itself. Furthermore, in vivo, when applied to excision wounds, this chemokine accelerates wound closure and the granulation tissue becomes more dense early in wound healing. This correlates with an increase in the number of myofibroblasts in the tissue. These results indicate that cCAF stimulates fibroblasts to differentiate into myofibroblasts and strongly suggest that this function may be responsible for the more effective wound closure induced by this chemokine.

Although little is known about chemokines and wound closure, expression of cCAF, IL-8 and MGSA is elevated until wound closure and then decreases to low but still elevated levels during granulation tissue formation (Martins-Green and Bissell, 1990; Engelhardt et al., 1998). In addition, knockout mice for CXCR2, a receptor for IL-8 and MGSA, exhibit delayed wound closure (Devalaraja et al., 2000). The results presented here shine light into these findings in vivo. Our observations that cCAF stimulates α-SMA expression directly, that this elevation in expression leads to increased contraction of collagen gels and to more rapid wound contraction and closure indicates that chemokines play significant roles in the formation of the granulation tissue of wounds. Furthermore, the small (15-amino acid) N-terminal peptide of the cCAF molecule has the same effects and is a promising target in designing drugs that affect the differentiation of myofibroblasts.

It has been shown that myofibroblasts can differentiate from fibroblasts when the latter cells are exposed to TGFβ in culture (Desmouliere et al., 1993) and that in vivo this growth factor directly stimulates myofibroblast differentiation (Serini and Gabbiani, 1999). Furthermore, most previously known stimulators of myofibroblast differentiation appear to act indirectly through TGFβ (Serini and Gabbiani, 1999). Therefore, our results identify the CXC chemokine, cCAF, as a new stimulator of myofibroblast differentiation in culture and in vivo. Unlike the receptors for TGFβ, chemokine receptors are G-protein linked and therefore the signal transduction pathways elicited to stimulate a-SMA production could be different. We are currently investigating the molecular mechanisms of cCAF-induced α-SMA production.

α-SMA-containing cells (myofibroblasts, smooth muscle cells and pericytes) play important functions in a variety of processes involved in wound healing, vasculogenesis/angiogenesis, and pathological conditions, especially in diseases that are characterized by excess scarring. In wound healing, myofibroblasts are particularly important in wound closure and contraction. For example, lack of myofibroblasts after corneal surgery leads to corneal flattening and widening of the wound and stimulation of myofibroblast differentiation in noncontractile fetal wounds leads to contraction of the wounds (Jester et al., 1999; Lanning et al., 2000). In disease states characterized by an accumulation of myofibroblasts, such as pulmonary fibrosis and scleroderma, myofibroblasts are thought to contribute significantly to the pathology of the disease, primarily because myofibroblasts tend to be highly fibrogenic (Powell et al., 1999). In addition, myofibroblasts are present in the stroma of many tumors and appear to be important for the survival of these tumors (Coffin et al., 1998; Schurch et al., 1998).

In addition to stimulating wound closure through the differentiation of myofibroblasts, cCAF may also be acting to increase the stability of new blood vessels in the granulation tissue. Smooth muscle cells of the new vasculature are known to differentiate from mesenchymal cells in response to signals from the endothelial cells (e.g., Carmeliet, 2000). These smooth muscle cells are essential for vascular maturation in connective tissue (Carmeliet, 2000). CXC chemokines are produced by the endothelial cells and fibroblasts of the connective tissue and promote angiogenesis (Martins-Green and Bissell, 1990; Martins-Green et al., 1991; Martins-Green et al., 1992; Martins-Green and Feugate, 1998; Belperio et al., 2000). These chemokines are known to affect endothelial cell migration, but part of their role in the formation of new blood vessels may be in stimulating fibroblasts to acquire α-SMA and become the smooth muscle cells of the vasculature.

Myofibroblast accumulation is prominent and high levels of chemokines are present in conditions characterized by excessive scarring, such as keloids, scleroderma and pulmonary fibrosis (Zhang et al., 1996; Nedelec et al, 2000), which indicates that chemokines participate in such diseases by stimulating myofibroblast differentiation. For example, levels of MCP-1, IL-8, and MIP-1α are high in pulmonary fibrosis (Keane et al., 1997; Hasegawa et al., 1999). These chemokines are also elevated in sclerotic tissue (Kadono et al., 1998; Hasegawa et al., 1999). Myofibroblasts in keloids express MGSA, while the cells of normal scars do not (Nirodi et al., 2000). Our results indicate that some of the problems in these conditions are due to the high levels of chemokines, leading to an increase in myofibroblast numbers, excess deposition of matrix molecules, and contraction of the tissue.

Controlling the differentiation of myofibroblasts can reasonably be expected mitigate the effects of fibrotic and other diseases. CXC chemokines could be well-suited for this purpose because they are not constitutively expressed and do not have the broad-ranging effects that TGFβ does. In addition, chemokines are very small molecules with no modification other than disulfide bonds and can therefore be produced recombinantly without much difficulty. In addition, chemokines bind to 7-transmembrane receptors, which are highly amenable to pharmacological manipulations. As a consequence, these proteins or their antagonists could be used to modulate the presence of myofibroblasts in both disease states and in abnormal wound healing. Furthermore, the ability of the 15-amino acid N-terminal peptide to stimulate effects similar to those stimulated by the whole cCAF molecule demonstrates that the peptide itself or peptide mimetics could be used for treatment of wounds with impaired closure.

In conclusion, a major role of cCAF in the granulation tissue is the stimulation of proper wound closure through the stimulation of myofibroblast differentiation. This is a previously unknown function for chemokines and it may represent a novel mechanism for the induction of myofibroblast differentiation, one not involving TGFβ. The results of these studies explain why chemokines contribute to the pathology of fibrotic diseases in which myofibroblasts play a significant part.

E. Abbreviations

| | |
|---|---|
| α-SMA | α-smooth muscle actin |
| cCAF | chicken Chemotactic and Angiogenic Factor |
| MGSA | Melanocyte Growth Stimulating Activity |
| IL-8 | Interleukin-8 |
| TGFβ1 | Transforming Growth Factorβ-1 |
| SDF-1 | Stromal-Derived Factor-1 |
| MCP-1 | Monocyte Chemotactic Protein-1 |
| RANTES | Regulated upon Activation, Normal T-cell Expressed, presumed Secreted |

F. References

Baggiolini, M., Dewald, B., and B. Moser. 1997. Human chemokines: an update. *Annu. Rev. Immunol.* 15:675–705.

Bazan, J. F., Bacon, K. B., Hardiman, G., Wang, W., Soo, K., Rossi, D., Greaves, D. R., Zlotnik, A., and T. J. Schall. 1997. A new class of membrane-bound chemokine with a CX3C motif. *Nature(Lond.)* 385: 640–644.

Belperio, J. A., Keane, M., Arenberg, D., Addison, C., Ehlert, J., Burdick, M. D., and R. Strieter. 2000. CXC chemokines in angiogenesis. *J. Leukoc. Biol.* 68:1–8.

Brown, L., Dubin, D., Lavigne, L., Logan, B., Dvorak, H., and L. Van de Water. 1993. Macrophages and fibroblasts express embryonic fibronectins during cutaneous wound healing. *Am. J. Pathol.* 142:793–801.

Carmeliet, P. 2000. Mechanisms of angiogenesis and arteriogenesis. *Nature Med.* 6:389–95. Clark, R. 1993. Basics of cutaneous wound repair. *J. Dermatol. Surg. Oncol.* 19:693–706.

Clark-Lewis, I., Kim K., Rajarathnam, K., Gong, J., Dewald, B., Moser, B., et al. 1995. Structure-activity relationships of chemokines. *J Leukoc. Biol.* 57:703–711.

Coffin, C., Dehner, L., and J. Meis-Kindblom. 1998 Inflammatory myofibroblastic tumor, inflammatory fibrosarcoma, and related lesions: an historical review with differential diagnostic considerations. *Seminars in Diagnostic Pathology* 15:102–10.

Desmouliere, A., Geinoz, A., Gabbiani, F., and G. Gabbiani. 1993. Transforming growth factor-beta 1 induces alpha-smooth muscle actin expression in granulation tissue myofibroblasts and in quiescent and growing cultured fibroblasts. *J. Cell Biol.* 122:103–111.

Devalaraja, R., Nanney, L., Qian, Q., Du, J., Yu, Y., Devalaraja, M. N., and A. Richmond. 2000. Delayed wound healing in CXCR2 knockout mice. *J. Investig. Dermatol.* 115:234–44.

Dimitrijevic-Bussod, M., Balzaretti-Maggi, V., and D. Gadbois. 1999. Extracellular matrix and radiation G1 cell cycle arrest in human fibroblasts. *Cancer Res.* 59:4843–4847.

Doucet, J., and J. Trifaro. 1988. A discontinous and highly porous sodium dodecyl sulfate-polyacrylamide slab gel system of high resolution. *Anal. Biochem.* 168:265–271.

Dunleavy, J., and J. Couchman. 1995. Interleukin-8 induces motile behavior and loss of focal adhesions in primary fibroblasts. *J. Cell Sci.* 108:311–321.

Engelhardt, E., Toksoy, A., Goebeler, M., Debus, S., Brocker, E., and R. Gillitzer. 1998. Chemokines IL-8, GROalpha, MCP-1, IP-10, and Mig are sequentially and differentially expressed during phase-specific infiltration of leukocyte subsets in human wound healing. *Amer. J. Pathol.* 153:1849–60.

Gabbiani, G. 1996. The cellular derivation and the life span of the myofibroblast. *Pathol. Res. Pract.* 192:708–711.

Germain, L., Jean, A., Auger, F., and D. Garrel. 1994. Human wound healing fibroblasts have greater contractile properties than dermal fibroblasts. *J. Surg. Res.* 57:268–273.

Gharaee-Kermani, M., Denholm, E., and S. Phan. 1996. Costimulation of fibroblast collagen and transforming growth factor b1 gene expression by monocyte chemoattractant protein-1 via specific receptors. *J. Biol. Chem.* 271:17779–17784.

Gupta, S. and J. Singh. 1994. Inhibition of endothelial cell proliferation by platelet factor-4 involves a unique action on S phase progression. *J. Cell Biol.* 127:1121–1127.

Hasegawa, M., Sato, S., and K. Takehara. 1999. Augmented production of chemokines (monocyte chemotactic protein-1 (MCP-1), macrophage inflammatory protein-1alpha (MIP-1alpha) and MIP-1beta) in patients with systemic sclerosis: MCP-1 and MIP-1alpha may be involved in the development of pulmonary fibrosis. *Clin. Exp. Immunol.* 117:159–65.

Jester, J., Huang, J., Barry-Lane, P., Kao, W., Petroll, W., and H. Cavanagh. 1999. Transforming growth factor(beta)-mediated corneal myofibroblast differentiation requires actin and fibronectin assembly. *Invest. Ophthalmol. Vis. Sci.* 40:1959–67.

Kadono, T., Kikuchi, K., Ihn, H., Takehara, K., and K. Tamaki. 1998. Increased production of interleukin 6 and interleukin 8 in scleroderma fibroblasts. *J. Rheumatol.* 25:296–301.

Keane, M., Arenberg, D., Lynch, J., Whyte, R., Iannettoni, M., Burdick, M., Wilke, C., Morris, S., Glass, M., DiGiovine, B., Kunkel, S., and R. Strieter. 1997. The CXC chemokines, IL-8 and IP-10, regulate angiogenic activity in idiopathic pulmonary fibrosis. *J. Immunol.* 159:1437–43.

Khouw, I., van Wachem, P., Plantinga, J., Vujaskovic, Z., Wissink, M., de Leij, L., and M. van Luyn. 1999. TGF-beta and bFGF affect the differentiation of proliferating porcine fibroblasts into myofibroblasts in vitro. *Biomaterials* 20:1815–1822.

Lanning, D., Diegelmann, R., Yager, D., Wallace, M., Bagwell, C., and J. Haynes. 2000. Myofibroblast induction with transforming growth factor-beta1 and -beta3 in cutaneous fetal excisional wounds. *J. Pediatr. Surg.* 35:183–187.

Luo, Y., D,Amore, P., and M. Dorf. 1996. b-chemokine TCA3 binds to and activates rat vascular smooth muscle cells. *J. Immunol.* 157:2143–2148.

Luster, A., Cardiff, R., MacLean, J., Crowe, K., and R. Granstein. 1998. Delayed wound healing and disorganized neovascularization in transgenic mice expressing the IP-10 chemokine. *Proceedings of the Association of American Physicians* 110:183–196.

Mackie, E., Halfter, W., and D. Liverani. 1988. Induction of tenascin in healing wounds. *J. Cell Biol.* 107:2757–2767.

Martins-Green, M., and M. Bissell. 1990. Localization of 9E3/CEF-4 in avian tissues: expression is absent in Rous sarcoma virus-induced tumors but is stimulated by injury. *J. Cell. Biol.* 110:581–595.

Martins-Green, M., Tilley, C., Schwarz, R., Hatier, C., and M. Bissell. 1991. Wound-factor-induced and cell cycle phase-dependent expression of 9E3/CEF4, the avian gro gene. *Cell Regul.* 2:739–52.

Martins-Green, M., Aotaki-Keen, A., Hjelmeland, L., and M. Bissell. 1992. The 9E3 protein: immunolocalization in vivo and evidence for multiple forms in culture. *J. Cell Sci.* 101:701–707.

Martins-Green, M., Stoeckle, M., Hampe, A., Wimberly, S., and H. Hanafusa. 1996. The 9E3/CEF4 cytokine: kinetics of secretion, processing by plasmin, and interaction with extracellular matrix. *Cytokine* 8:448–459.

Martins-Green, M., and H. Hanafusa. 1997. The 9E3/CEF4 gene and its product the chicken chemotactic and angiogenic factor (cCAF): potential roles in wound healing and tumor development. *Cytokine Growth Factor Rev.* 8:221–232.

Martins-Green, M., and J. E. Feugate. 1998. The 9E3/CEF4 gene product is a chemotactic and angiogenic factor that can initiate the wound healing cascade in vivo. *Cytokine* 10:522–535.

Martins-Green, M., and T. Kelly. 1998. The chicken chemotactic and angiogenic factor (9E3 gene product): Its angiogenic properties residue in the C-terminus of the molecule. *Cytokine* 10:819–830.

Masur, S., Dewal, H., Dinh, T., Erenburg, I., and S. Petridou. 1996. Myofibroblasts differentiate from fibroblasts when plated at low density. *Proc. Natl. Acad. Sci. USA* 93:4219–4223.

Nanney, L., Muellaer, S., Bueno, R., Pieper, S., and A. Richmond. 1995. Distribution of melanoma growth stimulatory activity or growth-regulated gene and the interleukin-8 receptor in human wound repair. *Am. J. Pathol.* 147:1248–1260.

Nedelec, B., Dodd, C., Scott, P., Ghahary, A., and E. Tredget. 1998. Effect of interferon-a2b on guinea pig wound closure and the expression of cytoskeletal proteins in vivo. *Wound Repair. Reg.* 6:202–212.

Nirodi, C., Devalaraja, R., Nanney, L., Arrindell, S., Russell, S., Trupin, J., and A. Richmond. 2000. Chemokine and chemokine receptor expression in keloid and normal fibroblasts. *Wound Repair Regen.* 8:371–382.

Powell, D., Mifflin, R., Valentich, J., Crowe, S., Saada, J., and A. West. 1999. Myofibroblasts. I. Paracrine cells important in health and disease. *Am. J Physiol.* 277:C1–9.

Prieschl, E. E., Kulmburg, P. A., and T. Baumruker. 1995. The nomenclature of chemokines. *Int. Arch. Allergy Immunol.* 107: 475–483.

Rennekampff, H., Hansbrough, J., Woods, V., Dore, C., Kiessig, V., and J. Schroder. 1997. Role of melanoma growth stimulatory activity (MGSA/gro) on keratinocyte function in wound healing. *Arch. Dermatol. Res.* 289:204–212.

Serini, G., and G. Gabbiani. 1999. Mechanisms of myofibroblast activity and phenotypic modulation. *Exp. Cell Res.* 250:273–283.

Stoeckle, M., and K. Barker. 1990. Two burgeoning families of platelet factor 4-related proteins: mediators of the inflammatory response. *New Biol.* 2:313–323.

Strieter, R., Polverini, P., Arenberg, D., and S. Kunkel. 1995. Role of CXC chemokines as regulators of angiogenesis. *Shock* 4:155–160.

Weber, M., Uguccioni, M., Baggiolini, M., Clark-Lewis, I., and C. Dahinden. 1996. Deletion of the NH2-terminal residue converts monocyte chemotactic protein 1 from an activator of basophil release to an eosinophil chemoattractant. *J. Exp. Med.* 183:681–685.

Youngs, S., Ali, S., Taub, D., and R. Rees. 1997. Chemokines induce migrational responses in human breast carcinoma cell lines. *Int. J. Cancer* 71:257–266.

Zhang, Y., Zhang, Y., Ogata, M., Chen, P., Harada, A., Hashimoto S., and K. Matsushima. 1999. Transforming growth factor-b1 polarizes murine hematopoietic progenitor cells to generate Langerhans cell-like dendritic cells through a monocyte/macrophage differentiation pathway. *Blood* 93:1208–1220.

Zlotnik, A., Morales, J., and J. Hedrick. 1999. Recent advances in chemokines and chemokine receptors. *Crit Rev. Immol.* 19:1–47.

---

What is claimed is:

1. A polypeptide comprising a single interleukin-8 (IL-8) fragment, wherein said IL-8 fragment consists of amino acid sequence SAKELR (SEQ ID NO.: 8), wherein said polypeptide is not cyclized.

2. A polypeptide comprising a single interleukin-8 (IL-8) fragment, wherein said IL-8 fragment consists of amino acid sequence AVLPRSAKELR (SEQ ID NO.: 9), wherein said polypeptide is not cyclized.

3. A composition comprising the polypeptide of claim 1, or 2 and a pharmaceutically acceptable carrier.

* * * * *